(12) United States Patent
Huang et al.

(10) Patent No.: US 9,314,464 B2
(45) Date of Patent: Apr. 19, 2016

(54) COMPOUNDS AND COMPOSITIONS AS PROTEIN KINASE INHIBITORS

(71) Applicant: Novartis AG, Basel (CH)

(72) Inventors: Shenlin Huang, San Diego, CA (US); Xianming Jin, San Ramon, CA (US); Zuosheng Liu, San Diego, CA (US); Daniel Poon, Piedmont, CA (US); John Tellew, La Jolla, CA (US); Yongqin Wan, Irvine, CA (US); Xing Wang, San Diego, CA (US); Yongping Xie, San Diego, CA (US)

(73) Assignee: Novartis AG, Basel (CH)

( * ) Notice: Subject to any disclaimer, the term of this patent is extended or adjusted under 35 U.S.C. 154(b) by 311 days.

(21) Appl. No.: 13/931,111

(22) Filed: Jun. 28, 2013

(65) Prior Publication Data

US 2013/0296318 A1    Nov. 7, 2013

Related U.S. Application Data

(62) Division of application No. 12/870,130, filed on Aug. 27, 2010, now Pat. No. 8,501,758.

(60) Provisional application No. 61/238,073, filed on Aug. 28, 2009, provisional application No. 61/313,039, filed on Mar. 11, 2010.

(51) Int. Cl.
| | |
|---|---|
| *A61K 31/535* | (2006.01) |
| *A61K 31/506* | (2006.01) |
| *C07D 401/14* | (2006.01) |
| *C07D 403/04* | (2006.01) |
| *A61K 45/06* | (2006.01) |
| *C07D 405/14* | (2006.01) |

(52) U.S. Cl.
CPC ............... *A61K 31/506* (2013.01); *A61K 45/06* (2013.01); *C07D 401/14* (2013.01); *C07D 403/04* (2013.01); *C07D 405/14* (2013.01)

(58) Field of Classification Search
CPC ... A61K 31/506; A61K 45/06; C07D 405/14; C07D 403/04; C07D 401/14
USPC .......................... 514/234.2, 264, 275, 210.18
See application file for complete search history.

(56) References Cited

U.S. PATENT DOCUMENTS

| | | | |
|---|---|---|---|
| 9,114,137 B2 | 9/1991 | Pulici et al. | |
| 5,717,100 A | 2/1998 | Selnick et al. | |
| 6,037,136 A | 3/2000 | Beach et al. | |
| 6,204,467 B1 | 3/2001 | Greenholtz, Jr. et al. | |
| 6,268,391 B1 | 7/2001 | Dickerson et al. | |
| 6,358,932 B1 | 3/2002 | Monia et al. | |
| 6,391,636 B1 | 5/2002 | Monia et al. | |
| 6,458,813 B1 | 10/2002 | Mantlo et al. | |
| 6,911,446 B2 | 6/2005 | Tang et al. | |
| 7,482,367 B2 | 1/2009 | Aikawa et al. | |
| 8,501,758 B2 | 8/2013 | Huang et al. | |
| 8,541,575 B2 | 9/2013 | Pulici et al. | |
| 8,791,265 B2 | 7/2014 | Pulici et al. | |
| 8,946,250 B2 | 2/2015 | Pulici et al. | |
| 2001/0006974 A1 | 7/2001 | Byrd et al. | |
| 2002/0137774 A1 | 9/2002 | Riedl et al. | |
| 2010/0022543 A1 | 1/2010 | Melvin | |
| 2010/0098763 A1 | 4/2010 | Bechtold | |
| 2010/0311751 A1 | 12/2010 | Schmitt | |
| 2011/0046370 A1 | 2/2011 | Sim et al. | |
| 2013/0053419 A1 | 2/2013 | Pulici et al. | |
| 2013/0217715 A1 | 8/2013 | Pulici et al. | |
| 2014/0005150 A1 | 1/2014 | Pulici et al. | |
| 2014/0309250 A1 | 10/2014 | Verma et al. | |

FOREIGN PATENT DOCUMENTS

| | | |
|---|---|---|
| JP | A 2011-515371 | 5/2011 |
| JP | A 2011-528698 | 11/2011 |
| JP | A 2012-512837 | 6/2012 |
| JP | A 2012-530099 | 11/2012 |
| JP | A 2013-503139 | 1/2013 |
| JP | 5475888 | 4/2014 |
| WO | WO 98/52940 | 11/1998 |
| WO | WO 00/31063 | 6/2000 |
| WO | WO 02/22577 | 3/2002 |
| WO | WO 03/055860 | 7/2003 |
| WO | WO 2005/068452 | 7/2005 |
| WO | WO2005123719 | 12/2005 |
| WO | WO2007021966 | 2/2007 |
| WO | WO 2007/024843 | 3/2007 |
| WO | WO2007105058 | 9/2007 |
| WO | WO 2007/123892 | 11/2007 |
| WO | WO2008042639 | 4/2008 |
| WO | WO2008045627 | 4/2008 |
| WO | WO2009016460 | 2/2009 |
| WO | WO2009/050291 | 4/2009 |
| WO | WO2009062676 | 5/2009 |
| WO | WO2009115572 | 9/2009 |

(Continued)

OTHER PUBLICATIONS

Goodacre, et al., "Imidazo[1,2-a]pyrimidines as Functionally Selective and Orally Bioavailable GABAxA[alpha]2/[alpha]3 Binding Site Agonists for the Treatment of Anxiety Disorders", J. Med. Chem., 2006, pp. 35-38, vol. 49, No. 1, American Chemical Society, US.

(Continued)

*Primary Examiner* — Jason Sims
*Assistant Examiner* — Ibrahim D Bori
(74) *Attorney, Agent, or Firm* — Fish & Richardson P.C.

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of B-Raf.

27 Claims, 1 Drawing Sheet

(56) References Cited

FOREIGN PATENT DOCUMENTS

| WO | WO 2009/137391 | 11/2009 |
|---|---|---|
| WO | WO2010010154 | 1/2010 |
| WO | WO2010034838 | 4/2010 |
| WO | WO 2010/056662 | 5/2010 |
| WO | WO2010100127 | 9/2010 |
| WO | WO 2011/025927 | 3/2011 |
| WO | WO2011092088 | 8/2011 |
| WO | WO2011126903 | 10/2011 |
| WO | WO 2012/128709 | 9/2012 |
| WO | WO 2012/174061 | 12/2012 |

OTHER PUBLICATIONS

Trivedi AR, et al., "Novel dihydropyrimidines as a potential new class of antitubercular agents", Bioorganic & Medicinal Chemistry Letters, 2010, pp. 6100-6102, vol. 20.
"A Study of ARRY—438162 in Patients with Rheumatoid Arthritis," ClinicalTrials.gov, last updated Aug. 29, 2012, retrieved on Apr. 12, 2014, http://www.clinicaltrials.gov/ct2/show/NCT00650767?term=Arthritis&recr=Open, 3 pages.
"MEK Inhibitor MSC1936369B Plus FOLFIRI in Second Line K-Ras Mutated Metastatic Colorectal Cancer (mCRC)," ClinicalTrials.gov, last updated Oct. 21, 2013, retrived on Apr. 12, 2014, http://cliical trials.gov/ct2/show/NCT01085331?term-MSC1936369B&rank=1, 4 pages.
Arnold, "Synthetische Reaktionen Von dimethylformamid XVL* Formylierung Von y-Picolin," Coll. Czech. Chem. Commun., 1963, 28:863 (English Abstract).
Cohen et al., "BRAF Mutation in Papillary Thyroid Carcinoma," J. Natl. Cancer Inst., 2003, 95:625-627.
Cohen, "The development and therapeutic potential of protein kinase inhibitors," Current Opinion in Chemical Biology, 1999, 3:459-465.
Culbertson et al., "New 7-substituted quinolone antibacterial agents. The synthesis of 1-ethyl-I,4-dihydro-4- oxo-7-(2-thiazolyl and 4-thiazolyl)-3- quinolinecarboxylic acids," J. Heterocycl. Chem, 1987, 24:1509.
Davies et al., "Mutations of the BRAF Gene in Human Cancer," Nature, 2002, 417:949-954.
Dhirendra et al., "Solid dispersions: A review," Pak. J. Pharm Sci, Apr. 2009, 22(2):234-246.
Fremin and Meloche, "From basic research to clinical development of MEK 1/2 inhibitors for cancer therapy," J. Hematology and Oncology, 2010, 3:8.
Grimm et al., "A New Strategy for the Synthesis of Benzylic Sulfonamides: Palladium-Catalyzed Arylation and Sulfonamide Metathesis," J. Org. Chem, 2007, 72(21):8135-8138.
Hagemann and Rapp, "Isotope-specific functions of Raf kinases," Expt. Cell Res., 1999, 253:34-46.
Hingorani et al., "Suppression of BRAFV599E in Human Melanoma Abrogates Transformation," Cancer Res., 2003, 63:5198-520.
Hoshino et al., "Constitutive activation of the 41-/43-kDa mitogen-activated protein kinase signaling pathway in human tumors," Oncogene, 1999, 18:813-822.
International Preliminary Report on Patentability in International Application No. PCT/EP2009/0595506, dated Jan. 25, 2011, 6 pages.
International Preliminary Report on Patentability in International Application No. PCT/EP2011/050654, dated Jul. 31, 2012, 6 pages.
International Preliminary Report on Patentability in International Application No. PCT/EP2013/073452, dated May 12, 2015, 7 pages.
International Preliminary Report on Patentability in International Application No. PCT/US2010/046930, dated Feb. 28, 2012, 8 pages.
International Preliminary Report on Patentability in International Application No. PCT/US2012/066185, dated, May 27, 2014, 8 pages.
International Report on Patentability in International Application No. PCT/EP2011/063325, dated Feb. 5, 2013, 8 pages.
International Search Report and Written Opinion in International Application No. PCT/US2012/066185, dated Mar. 5, 2013, 13 pages.
International Search Report in International Application No. PCT/EP2009/059506, dated Sep. 23, 2009, 3 pages.
International Search Report in International Application No. PCT/EP2011/050654, dated Apr. 6, 2011, 4 pages.
International Search Report in International Application No. PCT/EP2011/063325, dated Aug. 31, 2011, 3 pages.
International Search Report in International Application No. PCT/EP2013/073452, dated Dec. 13, 2013, 5 pages.
International Search Report in International Application No. PCT/US2010/046930, dated Oct. 19, 2010, 5 pages.
Japanese Preliminary Examination Report in Japanese Application No. 2014-098022, dated Nov. 18, 2015, 5 pages. (with English Translation).
Kolch et al., "The role of Raf kinases in malignant transformation," Exp. Rev. Mol. Med, http://citeseerx.ist.psu.edu/viewdoc/download?doi=10.1.1.114.8626&rep=repl&type=pdf, Apr. 25, 2002, 18 pages.
Lai et al., "Cotargeting histone deacetylases and oncongenic BRAF synergistically kills human melanoma cells by necrosis independently of RIPK1 and RIPK3," Cell Death and Disease, 2013, 4:e655, 13 pages.
McCubrey et al., "Emerging MEK inhibitors," Expert Opinion Emerging Drugs, Inform Healthcare, 2010, 15(2):203-223.
McLaughlin et al., "A Simple, Modular method for the Synthesis of 3,4,5-Trisubstituted Pyrazoles," JOC 2008, 73:4309-4312.
Mercer and Pritchard, "Raf proteins and cancer: B-Raf is identified as a mutational target," Biochim. Biophys. Acta, 2003, 1653:25-40.
Peyssonnaux and Eychene, "The Raf/MEK/ERK pathway: new concepts of activation," Biology of the Cell, 2001, 93:53-62.
Raju et al, "Inhibition of DNA Repair as a Mechanism of Enhanced Radioresponse of Head and Neck Carcinoma Cells by a Selective Cyclooxygenase-2 Inhibitor, Celecoxib," Int. J. Radiation Oncology Biol. Phys., 2005, 53:520-528.
Saulnier et al., "An Efficient method for the Synthesis of Guanidino Prodrugs," Bioorganic and Medicinal Chemistry Letters, 1994, 4:1985.
Sherman et al., "Biologically targeted therapies for thyroid cancers," Thyroid Cancer, Jan. 2011, 329-349.
Tannapfel et al., "Mutations of the BRAF gene in cholangiocardinoma but not the hepatocellular carcinoma," Gut, 2003, 52:706-712.
Tran et al., "Dissolution-modulating mechanism of pH modifiers in solid dispersion containing weakly acidic or basic drugs with poor water solubility," Expert. Opin. Drug Deliv., Dec. 2010, 7(5):647-661.
Velculescu, "Defining the Blueprint of the Cancer Genome," Carcinogenesis, 2008, 29:1087-1091.
Wellbrock et al., "B-RAF is an Oncogene in Melanocytes," Cancer Res., 2004, 64:2338-2342.
Wojnowski et al., "Endothelial apoptosis in Braf-deficient mice," Nature Genet., 1997, 16:293-297.
Written Opinion in International Application No. PCT/EP2013/073452, dated Dec. 13, 2013, 6 pages.
Written Opinion of the International Searching Authority in International Application No. PCT/EP2009/0595506, dated Sep. 23, 2009, 5 pages.
Written Opinion of the International Searching Authority in International Application No. PCT/EP2011/050654, dated Apr. 6, 2011, 5 pages.
Written Opinion of the International Searching Authority in International Application No. PCT/EP2011/063325, dated Feb. 3, 2013, 6 pages.
Written Opinion of the International Searching Authority in International Application No. PCT/US2010/046930, dated Oct. 9, 2010, 7 pages.
Young et al., "Discovery and evaluation of potent P1 aryl heterocycle-based thrombin inhibitors," J. Med. Chem., 2004. 47:2995-3008.

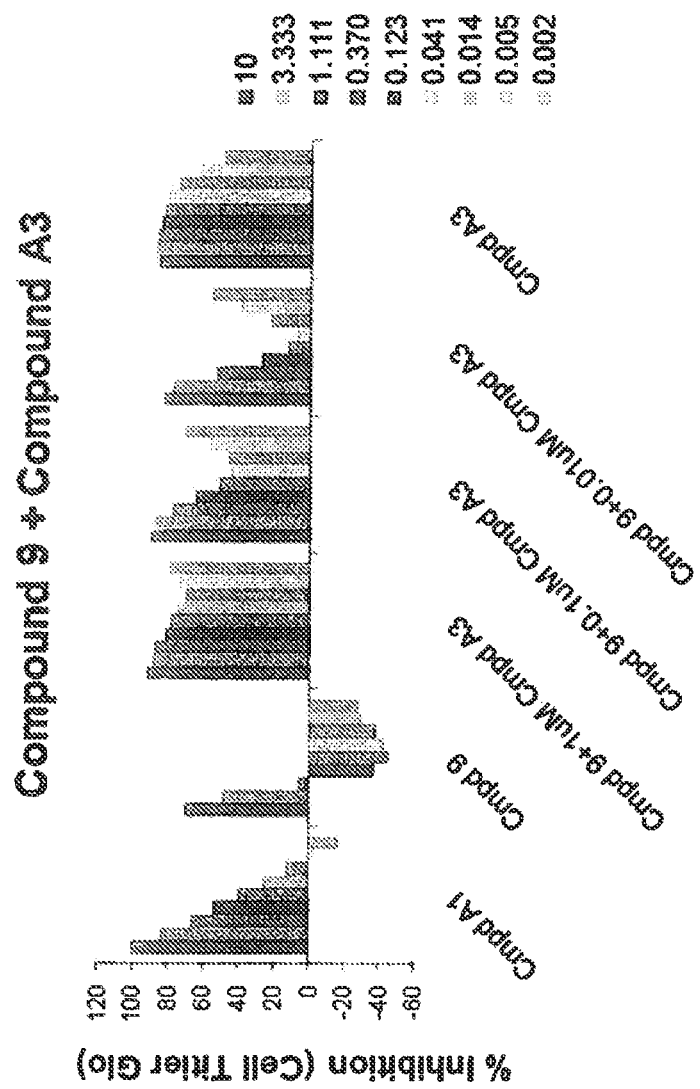

COMPOUNDS AND COMPOSITIONS AS PROTEIN KINASE INHIBITORS

CROSS-REFERENCE TO RELATED APPLICATIONS

This application is a divisional application of application Ser. No. 12/870,130, filed 27 Aug. 2010, which application claims the benefit of priority to U.S. Provisional Patent Application No. 61/238,073, filed 28 Aug., 2009 and U.S. Provisional Patent Application No. 61/313,039, filed 11 Mar., 2010. The full disclosures of these applications are incorporated herein by reference in their entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of B-Raf.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, trkB, Met, and the fibroblast growth factor receptor, FGFR3; non-receptor tyrosine kinases such as Abl and the fusion kinase BCR-Abl, Lck, Csk, Fes, Bmx and c-src; and serine/threonine kinases such as B-Raf, sgk, MAP kinases (e.g., MKK4, MKK6, etc.) and SAPK2α, SAPK2β and SAPK3. Aberrant kinase activity has been observed in many disease states including benign and malignant proliferative disorders as well as diseases resulting from inappropriate activation of the immune and nervous systems.

The novel compounds of this invention inhibit the activity of B-Raf or mutant forms thereof (for example V600E) and are, therefore, expected to be useful in the treatment of B-Raf-associated diseases.

SUMMARY OF THE INVENTION

In one aspect, the present invention provides compounds of Formula I:

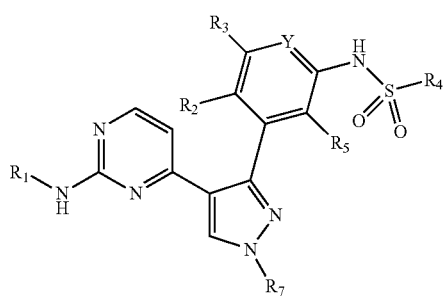

in which:

Y is selected from N and $CR_6$;

$R_1$ is selected from hydrogen, $-X_1R_{8a}$, $-X_1OX_2R_{8a}$, $-X_1C(O)NR_{8a}R_{8b}$, $-X_1NR_{8a}X_2R_{8b}$, $-X_1NR_{8a}C(O)X_2OR_{8b}$, $-X_1NR_{8a}C(O)X_2NR_{8a}R_{8b}$, $-X_1NR_{8a}S(O)_{0-2}R_{8b}$; wherein each $X_1$ is independently $C_{1-4}$alkylene; and $X_1$ optionally has 1 to 3 hydrogens replaced with a group selected from hydroxy, halo, cyano, $C_{1-4}$alkyl, halo-substituted-$C_{1-4}$alkyl, $C_{1-4}$alkoxy and halo-substituted-$C_{1-4}$alkoxy; $X_2$ is selected from a bond and $C_{1-4}$alkylene; wherein $R_{8a}$ and $R_{8b}$ are independently selected from hydrogen, $C_{1-6}$alkyl, halo-substituted-$C_{1-6}$alkyl, $C_{3-8}$cycloalkyl, heteroaryl and $C_{3-8}$heterocycloalkyl; wherein the cycloalkyl, heterocycloalkyl or heteroaryl of $R_{8a}$ or $R_{8b}$ is optionally substituted with 1 to 3 radicals independently selected from amino, cyano, $C_{1-4}$alkyl, $C_{1-4}$alkoxy, halo-substituted-$C_{1-4}$alkyl and halo-substituted-$C_{1-4}$alkoxy; with the proviso that $R_{8b}$ is not hydrogen when $R_1$ is selected from $-X_1NHC(O)OR_{8b}$ and $-X_1NR_{8a}S(O)_{0-2}R_{8b}$;

$R_2$, $R_3$, $R_5$ and $R_6$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy; with the proviso that when $R_5$ is fluoro and $R_1$ is selected from hydrogen, $-X_1R_{8a}$, $-X_1OX_2R_{8a}$, $-X_1C(O)NR_{8a}R_{8b}$, $-X_1NR_{8a}X_2R_{8b}$, $-X_1NR_{8a}C(O)X_2OR_{8b}$ and $-X_1NR_{8a}S(O)_{0-2}R_{8b}$, $R_3$ and $R_6$ are not both hydrogen;

$R_4$ is selected from $-R_9$ and $-NR_{10}R_{11}$; wherein $R_9$ is selected from $C_{1-6}$alkyl, $C_{3-8}$cycloalkyl, $C_{3-8}$heterocycloalkyl, aryl and heteroaryl; wherein said alkyl, cycloalkyl, heterocycloalkyl, aryl or heteroaryl of $R_9$ is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy; and $R_{10}$ and $R_{11}$ are independently selected from hydrogen and $R_9$;

$R_7$ is selected from hydrogen, $C_{1-4}$alkyl, $C_{3-8}$cycloalkyl and $C_{3-5}$heterocycloalkyl; wherein said alkyl, cycloalkyl or heterocycloalkyl of $R_7$ is optionally substituted with 1 to 3 radicals independently selected from halo, cyano, hydroxyl, $C_{1-4}$alkyl, halo-substituted-$C_{1-4}$alkyl, $C_{1-4}$alkoxy and halo-substituted-$C_{1-4}$alkoxy; and the N-oxide derivatives, prodrug derivatives, protected derivatives, the tautomers, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly B-Raf activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly B-Raf activity, particularly mutant B-raf (for example V600E), contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

BRIEF DESCRIPTION OF THE DRAWINGS

FIG. 1 illustrates that the addition of a MEK small molecule inhibitor can reverse the induced ERK signaling, cell growth and transformation caused by a Raf small molecule inhibitor.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted-$C_{1-4}$alkyl means and alkyl group (branched or unbranched) wherein any of the hydrogens can be substituted with a halogen. For example, halo-substituted-$C_{1-4}$alkyl can be trifluoromethyl, difluoroethyl, pentafluoroethyl, and the like. Similarly, hydroxy-substituted-$C_{1-6}$alkyl means and alkyl group (branched or unbranched) wherein any of the hydrogens can be substituted with a hydroxyl. For example, hydroxy-substituted-$C_{1-6}$alkyl includes 2-hydroxyethyl, and the like. Similarly, cyano-substituted-$C_{1-6}$alkyl means and alkyl group (branched or unbranched) wherein any of the hydrogens can be substituted with cyano.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heteroaryl" is as defined for aryl above where one or more of the ring members is a heteroatom. For example, heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes 2H-pyran, 4H-pyran, piperidine, 1,4-dioxane, morpholine, 1,4-dithiane, thiomorpholino, imidazolidin-2-one, tetrahydrofuran, piperazine, 1,3,5-trithiane, pyrrolidine, pyrrolidinyl-2-one, piperidine, piperidinone, 1,4-dioxa-8-aza-spiro[4.5]dec-8-yl, etc.

"Halogen" (or halo) represents chloro, fluoro, bromo or iodo.

"pMEK" means phosphorylated Mek.

"pERK" means phosphorylated ERK.

"Treat", "treating" and "treatment" refer to a method of alleviating or abating a disease and/or its attendant symptoms.

Compounds of the invention are named using Chemdraw Ultra (Version 10.0) and/or ChemAxon Name Generator (J Chem Version 5.3.1.0).

DESCRIPTION OF THE PREFERRED EMBODIMENTS

The present invention provides compounds, compositions and methods for the treatment of kinase related disease, particularly B-Raf kinase related diseases; for example, metastatic melanomas, solid tumors, brain tumors such as Glioblastoma multiform (GBM), acute myelogenous leukemia (AML), prostate cancer, gastric cancer, papillary thyroid carcinoma, ovarian low-grade carcinoma, and colorectal cancer.

In one embodiment, with reference to compounds of Formula I, $R_1$ is selected from —$X_1R_{8a}$ and —$X_1NHC(O)OR_{8b}$; wherein each $X_1$ is independently $C_{1-4}$alkylene; and $X_1$ optionally has 1 to 3 hydrogens replaced with a group selected from hydroxy, halo, cyano, $C_{1-4}$alkyl and halo-substituted-$C_{1-4}$alkyl; wherein $R_{8a}$ and $R_{8b}$ are independently selected from hydrogen and $C_{1-6}$alkyl; with the proviso that $R_{8b}$ is not hydrogen when $R_1$ is —$X_1NHC(O)OR_{8b}$;

In another embodiment are compounds of Formula Ia:

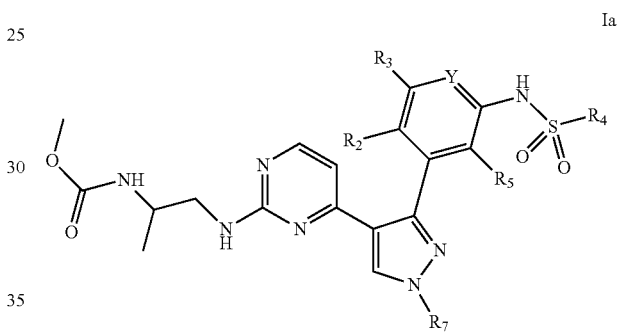

Ia in which: Y is selected from N and $CR_6$; $R_2$, $R_3$, $R_5$ and $R_6$ are independently is selected from hydrogen, halo, cyano, $C_{1-4}$alkyl, halo-substituted-$C_{1-4}$alkyl, $C_{1-4}$alkoxy and halo-substituted-$C_{1-4}$alkoxy; with the proviso that when $R_5$ is fluoro and $R_1$ is selected from hydrogen, —$X_1R_{8a}$, —$X_1OX_2R_{8a}$, —$X_1C(O)NR_{8a}R_{8b}$, —$X_1NR_{8a}X_2R_{8b}$, —$X_1NR_{8a}C(O)X_2OR_{8b}$ and —$X_1NR_{8a}S(O)_{0-2}R_{8b}$, $R_3$ and $R_6$ are not both hydrogen; $R_4$ is selected from —$R_9$ and —$NR_{10}R_{11}$; wherein $R_9$ is selected from $C_{1-6}$alkyl, $C_{3-8}$cycloalkyl, $C_{3-8}$heterocycloalkyl, aryl and heteroaryl; wherein said alkyl, cycloalkyl, heterocycloalkyl, aryl or heteroaryl of $R_9$ is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy; and $R_{10}$ and $R_{11}$ are independently selected from hydrogen and $R_9$; and $R_7$ is selected from hydrogen, $C_{1-4}$alkyl, $C_{3-5}$cycloalkyl and $C_{3-5}$heterocycloalkyl; wherein said alkyl, cycloalkyl or heterocycloalkyl of $R_7$ is optionally substituted with 1 to 3 radicals independently selected from halo, cyano, hydroxyl, $C_{1-4}$alkyl, halo-substituted-$C_{1-4}$alkyl, $C_{1-4}$alkoxy and halo-substituted-$C_{1-4}$alkoxy.

In a further embodiment, $R_4$ is —$R_9$; wherein $R_9$ is selected from $C_{1-3}$alkyl and $C_{3-8}$cycloalkyl; wherein said alkyl or cycloalkyl of $R_9$ is optionally substituted with 1 to 3 radicals independently selected from halo and halo-substituted-$C_{1-4}$alkyl.

In a further embodiment, $R_2$ is selected from hydrogen and fluoro; $R_3$ is selected from chloro, fluoro and methyl; $R_5$ is selected hydrogen, from chloro and fluoro; Y is selected from N and $CR_6$; and $R_6$ is selected from hydrogen and fluoro.

In a further embodiment are compounds selected from: methyl N-[(2S)-1-({4-[3-(3-chloro-5-methanesulfonamidophenyl)-1-(propan-2-yl)-1H-pyrazol-4-yl]pyrimidin-2-yl}amino)propan-2-yl]carbamate; methyl N-[(2S)-1-[(4-{3-[2-fluoro-3-(propane-1-sulfonamido)phenyl]-1-(propan-2-yl)-1H-pyrazol-4-yl}pyrimidin-2-yl)amino]propan-2-yl]carbamate; methyl N-[(2S)-1-({4-[3-(2-fluoro-3-methanesulfonamidophenyl)-1-(propan-2-yl)-1H-pyrazol-4-yl]pyrimidin-2-yl}amino)propan-2-yl]carbamate; methyl N-[(2S)-1-[(4-{3-[3-chloro-5-(propane-1-sulfonamido)phenyl]-1-(propan-2-yl)-1H-pyrazol-4-yl}pyrimidin-2-yl)amino]propan-2-yl]carbamate; methyl N-[(2S)-1-({4-[3-(2,6-difluoro-3-methanesulfonamidophenyl)-1-(propan-2-yl)-1H-pyrazol-4-yl]pyrimidin-2-yl}amino)propan-2-yl]carbamate; methyl N-[(2S)-1-[(4-{3-[2,6-difluoro-3-(propane-1-sulfonamido)phenyl]-1-(propan-2-yl)-1H-pyrazol-4-yl}pyrimidin-2-yl)amino]propan-2-yl]carbamate; methyl N-[(2S)-1-{[4-(3-{2-fluoro-3-[(3,3,3-trifluoropropane)sulfonamido]phenyl}-1-(propan-2-yl)-1H-pyrazol-4-yl)pyrimidin-2-yl]amino}propan-2-yl]carbamate; methyl N-[(2S)-1-({4-[3-(3-chloro-2-methanesulfonamidopyridin-4-yl)-1-(propan-2-yl)-1H-pyrazol-4-yl]pyrimidin-2-yl}amino)propan-2-yl]carbamate; methyl N-[(2S)-1-({4-[3-(3-fluoro-2-methanesulfonamidopyridin-4-yl)-1-(propan-2-yl)-1H-pyrazol-4-yl]pyrimidin-2-yl}amino)propan-2-yl]carbamate; methyl N-[(2S)-1-({4-[3-(2-chloro-3-ethanesulfonamido-4,5-difluorophenyl)-1-(propan-2-yl)-1H-pyrazol-4-yl]pyrimidin-2-yl}amino)propan-2-yl]carbamate; methyl N-[(2S)-1-({4-[3-(2,4-difluoro-3-methanesulfonamidophenyl)-1-(propan-2-yl)-1H-pyrazol-4-yl]pyrimidin-2-yl}amino)propan-2-yl]carbamate; methyl N-[(2S)-1-({4-[1-(propan-2-yl)-3-(2,4,5-trifluoro-3-methanesulfonamidophenyl)-1H-pyrazol-4-yl]pyrimidin-2-yl}amino)propan-2-yl]carbamate; methyl N-[(2S)-1-({4-[3-(3-methanesulfonamidophenyl)-1-(propan-2-yl)-1H-pyrazol-4-yl]pyrimidin-2-yl}amino)propan-2-yl]carbamate; methyl N-[(2S)-1-({4-[3-(3-ethanesulfonamido-2,4-difluorophenyl)-1-(propan-2-yl)-1H-pyrazol-4-yl]pyrimidin-2-yl}amino)propan-2-yl]carbamate; methyl N-[(2S)-2-({4-[3-(5-chloro-2-fluoro-3-methanesulfonamidophenyl)-1-(propan-2-yl)-1H-pyrazol-4-yl]pyrimidin-2-yl}amino)propyl]carbamate; methyl N-[(2S)-1-({4-[3-(5-chloro-2-fluoro-3-methanesulfonamidophenyl)-1-(oxan-2-yl)-1H-pyrazol-4-yl]pyrimidin-2-yl}amino)propan-2-yl]carbamate; methyl N-[(2S)-1-[(4-{3-[2,4-difluoro-3-(propane-1-sulfonamido)phenyl]-1-(propan-2-yl)-1H-pyrazol-4-yl}pyrimidin-2-yl)amino]propan-2-yl]carbamate; methyl N-[(2S)-1-({4-[3-(3-cyclopropanesulfonamido-2,5-difluorophenyl)-1-(propan-2-yl)-1H-pyrazol-4-yl]pyrimidin-2-yl}amino)propan-2-yl]carbamate; methyl N-[(2S)-1-({4-[3-(5-chloro-3-cyclopropanesulfonamido-2-fluorophenyl)-1-(propan-2-yl)-1H-pyrazol-4-yl]pyrimidin-2-yl}amino)propan-2-yl]carbamate; and methyl N-[(2S)-1-[(4-{3-[5-chloro-2-fluoro-3-(propane-1-sulfonamido)phenyl]-1-(propan-2-yl)-1H-pyrazol-4-yl}pyrimidin-2-yl)amino]propan-2-yl]carbamate.

In another embodiment are compounds of Formula Ib:

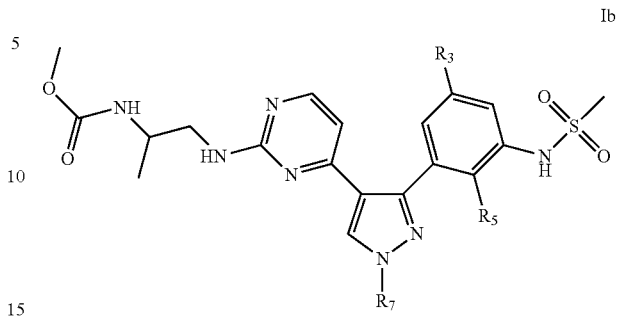

Ib in which: $R_3$ is selected from chloro, fluoro and methyl; $R_5$ is selected from fluoro and chloro; and $R_7$ is selected from ethyl and isopropyl.

In a further embodiment are compounds selected from: methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate; methyl N-[(2S)-1-({4-[3-(2,5-difluoro-3-methanesulfonamidophenyl)-1-(propan-2-yl)-1H-pyrazol-4-yl]pyrimidin-2-yl}amino)propan-2-yl]carbamate; methyl N-[(2S)-1-({4-[3-(5-chloro-2-fluoro-3-methanesulfonamidophenyl)-1-ethyl-1H-pyrazol-4-yl]pyrimidin-2-yl}amino)propan-2-yl]carbamate; methyl N-[(2S)-1-({4-[3-(2-fluoro-3-methanesulfonamido-5-methylphenyl)-1-(propan-2-yl)-1H-pyrazol-4-yl]pyrimidin-2-yl}amino)propan-2-yl]carbamate; methyl N-[(2S)-1-({4-[3-(2-chloro-3-methanesulfonamido-5-methylphenyl)-1-(propan-2-yl)-1H-pyrazol-4-yl]pyrimidin-2-yl}amino)propan-2-yl]carbamate; methyl N-[(2S)-1-({4-[3-(2-chloro-5-fluoro-3-methanesulfonamidophenyl)-1-(propan-2-yl)-1H-pyrazol-4-yl]pyrimidin-2-yl}amino)propan-2-yl]carbamate; methyl N-[(2R)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate; methyl N-[(2S)-1-({4-[3-(2,5-dichloro-3-methanesulfonamidophenyl)-1-(propan-2-yl)-1H-pyrazol-4-yl]pyrimidin-2-yl}amino)propan-2-yl]carbamate; and methyl N-[(2S)-1-({4-[3-(5-chloro-2-fluoro-3-methanesulfonamidophenyl)-1H-pyrazol-4-yl]pyrimidin-2-yl}amino)propan-2-yl]carbamate.

In another embodiment are compounds selected from: N-[5-chloro-3-(4-{2-[(2-cyanoethyl)amino]pyrimidin-4-yl}-1-(propan-2-yl)-1H-pyrazol-3-yl)-2-fluorophenyl]methanesulfonamide; N-{5-chloro-3-[4-(2-{[2-(dimethylamino)ethyl]amino}pyrimidin-4-yl)-1-(propan-2-yl)-1H-pyrazol-3-yl]-2-fluorophenyl}methanesulfonamide; N-(5-chloro-2-fluoro-3-{4-[2-(methylamino)pyrimidin-4-yl]-1-(propan-2-yl)-1H-pyrazol-3-yl}phenyl)methanesulfonamide; and N-{3-[4-(2-aminopyrimidin-4-yl)-1-(propan-2-yl)-1H-pyrazol-3-yl]-5-chloro-2-fluorophenyl}methanesulfonamide.

In a further embodiment are compounds selected from the Examples and Tables, infra.

In a further embodiment are intermediate compounds selected from: 3-Bromo-5-chloro-2-fluoroaniline; cyano-(2-methylthio-pyrimidin-4-yl)-acetic acid tert-butyl ester; 1-Isopropyl-4-(2-(methylthio)pyrimidin-4-yl)-1H-pyrazol-3-amine; 2-((2-Benzylidene-1-ethylhydrazinyl)methylene)-malononitrile; 1-(3-Amino-1-isopropyl-1H-pyrazol-4-yl)ethanone; 1-(3-Iodo-1-isopropyl-1H-pyrazol-4-yl)ethanone; 1-(3-Iodo-1-ethyl-1H-pyrazol-4-yl)ethanone; 1-(3-Iodo-1-methyl-1H-pyrazol-4-yl)ethanone; 3-(Dimethylamino)-1-

(3-iodo-1-isopropyl-1H-pyrazol-4-yl)prop-2-en-1-one; 3-(Dimethylamino)-1-(3-iodo-1-ethyl-1H-pyrazol-4-yl) prop-2-en-1-one; 3-(Dimethylamino)-1-(3-iodo-1-methyl-1H-pyrazol-4-yl)prop-2-en-1-one; 4-(3-Iodo-1-isopropyl-1H-pyrazol-4-yl)pyrimidin-2-amine; 4-(3-Iodo-1-ethyl-1H-pyrazol-4-yl)pyrimidin-2-amine; 4-(3-Iodo-1-methyl-1H-pyrazol-4-yl)pyrimidin-2-amine; 4-(3-Iodo-1-isopropyl-1H-pyrazol-4-yl)pyrimidin-2-ol; 2-Chloro-4-(3-iodo-1-isopropyl-1H-pyrazol-4-yl)pyrimidine; (S)-Methyl 1-(4-(3-iodo-1-isopropyl-1H-pyrazol-4-yl)pyrimidin-2-ylamino) propan-2-ylcarbamate; (R)-Methyl 1-(4-(3-iodo-1-isopropyl-1H-pyrazol-4-yl)pyrimidin-2-ylamino)propan-2-ylcarbamate; (S)-tert-butyl 1-(4-(3-iodo-1-isopropyl-1H-pyrazol-4-yl)pyrimidin-2-ylamino)propan-2-ylcarbamate; 3-(4-(3-iodo-1-isopropyl-1H-pyrazol-4-yl)pyrimidin-2-ylamino)propanenitrile; 4-(3-iodo-1-isopropyl-1H-pyrazol-4-yl)-N-methylpyrimidin-2-amine; $N^1$-(4-(3-iodo-1-isopropyl-1H-pyrazol-4-yl)pyrimidin-2-yl)-$N^2$,$N^2$-dimethylethane-1,2-diamine; N-(3-bromo-2,4-difluorophenyl)propane-1-sulfonamide; 3-Fluoro-4-iodopyridin-2-amine; 3-chloro-4-iodopyridin-2-amine; 3-Bromo-2,5,6-trifluoroaniline; 2,4-Dibromo-3,6-dichloroaniline; 3-bromo-2-chloro-5-methylaniline; 3-bromo-2,5-difluoroaniline; 3-Bromo-5-chloro-2-fluorobenzoic acid; Tert-butyl 3-bromo-5-chloro-2-fluorophenylcarbamate; tert-butyl 3-bromo-2-fluoro-5-methylphenylcarbamate; Tert-butyl 5-chloro-2-fluoro-3-(4,4,5,5-tetramethyl-1,3,2-dioxaborolan-2-yl)phenylcarbamate; tert-butyl 2,6-difluoro-3-(4,4,5,5-tetramethyl-1,3,2-dioxaborolan-2-yl)phenylcarbamate; N-(2,4-difluoro-3-(4,4,5,5-tetramethyl-1,3,2-dioxaborolan-2-yl)phenyl)propane-1-sulfonamide; 2-(2-fluoro-3-nitrophenyl)-4,4,5,5-tetramethyl-1,3,2-dioxaborolane; 2,5-difluoro-3-(4,4,5,5-tetramethyl-1,3,2-dioxaborolan-2-yl) aniline; 2-chloro-5-fluoro-3-(4,4,5,5-tetramethyl-1,3,2-dioxaborolan-2-yl)aniline; 2,5-dichloro-3-(4,4,5,5-tetramethyl-1,3,2-dioxaborolan-2-yl)aniline; 2-chloro-5-methyl-3-(4,4,5,5-tetramethyl-1,3,2-dioxaborolan-2-yl) aniline; tert-butyl 2-fluoro-5-methyl-3-(4,4,5,5-tetramethyl-1,3,2-dioxaborolan-2-yl)phenylcarbamate; 3-fluoro-4-(4,4,5,5-tetramethyl-1,3,2-dioxaborolan-2-yl)pyridin-2-amine; 2,3,6-trifluoro-5-(4,4,5,5-tetramethyl-1,3,2-dioxaborolan-2-yl)aniline; 3-chloro-4-(4,4,5,5-tetramethyl-1,3,2-dioxaborolan-2-yl)pyridin-2-amine; 3-chloro-5-(4,4,5,5-tetramethyl-1,3,2-dioxaborolan-2-yl)aniline; and 3-methoxy-6-methyl-5-(4,4,5,5-tetramethyl-1,3,2-dioxaborolan-2-yl)aniline.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

Some Raf inhibitors, in addition to increasing MEK and ERK signaling in wild-type B-Raf cells, also induce cell growth in cancer cell lines and cause transformation and growth in fibroblasts. The induction of downstream signaling has previously been attributed to published Raf pathway feedback loops. However, induction of pMEK and pERK can occur within minutes of Raf inhibitor treatment, even before reported feedback phosphorylation events are seen on B-Raf and C-Raf. The induction of signaling and cell growth both occur in a biphasic pattern, with low compound concentrations (0.01-0.1 µM) causing maximal induction, and higher compound concentrations (1-10 µM) causing less profound induction. Such a biphasic pattern is also observed in biochemical assays with purified wild-type B-Raf or C-Raf and is suggestive of a mechanism involving the interaction of two signaling subunits. In addition, Raf dimerization can up regulate pMEK, not through trans-phosphorylation of Raf molecules but presumably by a conformational activation of the kinase. Consistent with that model, Raf inhibitor treatment induces B-Raf/C-Raf dimer formation in cells. In addition, knockdown of A- or B-Raf with siRNA does not abrogate the Raf inhibitor induction of pMEK and pERK, and knockdown of C-Raf only slightly decreases the induction. Notably, knockdown of K-Ras in K-Ras mutant cells also only slightly decreases the induction, implying that this effect is not primarily mediated by Ras. Taken together, the data suggest a model in which inhibitor binding to one Raf molecule induces dimerization and conformational activation of a partner Raf molecule in the dimer. This can explain why wild-type Raf and mutant Ras tumors are insensitive to selective Raf kinase inhibitors and might also have important implications for toxicity, since induction of strong mitogenic signaling could lead to hyper proliferation of normal tissues. Understanding the Raf inhibitor induction mechanism may lead to the design of improved inhibitors.

The addition of a MEK inhibitor in combination with a Raf inhibitor leads to a significant inhibition of ERK signaling and consequently a decrease in cellular proliferation and transformation. Since MEK inhibitor treatments alone have led to dose limiting toxicities in the clinic, a Raf plus MEK inhibitor combination may represent a superior treatment strategy.

The present invention also includes combinations of the BRaf inhibitors disclosed in this invention with other agents. In particular, the present invention provides for combinations with MEK1/2 inhibitors. FIG. 1 illustrates that the addition of a MEK small molecule inhibitor can reverse the induced ERK signaling, cell growth and transformation caused by a Raf small molecule inhibitor. For example, a compound of Formula I (compound 9 of the invention, namely: ((S)-methyl 1-(4-(3-(5-chloro-2-fluoro-3-(methylsulfonamido)phenyl)-1-isopropyl-1H-pyrazol-4-yl)pyrimidin-2-ylamino)propan-2-ylcarbamate) can lead to an induction in cellular proliferation, seen as a negative inhibition in FIG. 1 of a Cell Titer Glo assay using SW620 cells. The Y-axis shows negative and positive inhibition. Each experiment is shown as a series of 9 serial dilutions between 10 and 0.002 M. Compound A1 (N-(4-methyl-3-(1-(6-(4-methylpiperazin-1-ylamino)pyrimidin-4-yl)-1H-imidazol-2-ylamino)phenyl)-3-(trifluoromethyl)benzamide) is a control, A3 is a MEK inhibitor (PD0325901). Compound 9 is tested in the absence and presence of 1 µM, 0.1 µM and 0.01 µM of MEK inhibitor A3.

Pharmacology and Utility

Compounds of the invention modulate the activity of kinases and, as such, are useful for treating diseases or disorders in which kinases contribute to the pathology and/or symptomology of the disease. Examples of kinases that are inhibited by the compounds and compositions described herein and against which the methods described herein are useful include, but are not limited to, B-Raf, including mutant forms of B-Raf.

The mitogen-activated protein kinase (MAPK) pathway mediates the activity of a number of effector molecules which coordinate to control cellular proliferation, survival, differentiation and migration. Stimulation of cells by, for example, growth factors, cytokines or hormones results in the plasma membrane-associated Ras becoming GTP-bound and thereby activated to recruit Raf. This interaction induces the kinase activity of Raf leading to direct phosphorylation of MAPK/ERK (MEK), which in turn phosphorylates the extracellular signal-related kinase (ERK). Activated ERK then phosphorylates a wide array of effector molecules, for example, kinases, phosphatases, transcription factors and cytoskeletal proteins. Therefore, the Ras-Raf-MEK-ERK signaling pathway transmits signals from cell surface receptors to the nucleus and is essential, for example, in cell proliferation and survival. The regulation of this signaling cascade is further enriched by the multiple isoforms of Ras (including K-Ras, N-Ras and H-Ras), Raf (A-Raf, B-Raf, C-Raf/Raf-1), MEK (MEK-1 and MEK-2) and ERK (ERK-1 and ERK-2). Since 10-20% of human cancers harbor oncogenic Ras mutations and many human cancers have activated growth factor receptors, this pathway is an ideal target for intervention.

The essential role and the position of Raf in many signaling pathways has been demonstrated from studies using deregulated and dominant inhibitory Raf mutants in mammalian cells as well as from studies employing biochemical and genetic techniques to model organisms. In the past, the focus on Raf being an anti-tumor drug target centered on its function as a downstream effector of Ras. However, recent findings suggest that Raf may have a prominent role in the formation of certain tumors with no requirement of an oncogenic Ras allele. In particular, activating alleles of B-Raf and N-Ras have been identified in ~70% of melanomas, 40% of papillary thyroid carcinoma, 30% of ovarian low-grade carcinoma, and 10% of colorectal cancers. Mutations in K-Ras occur in approximately 90% of pancreatic cancers. Most B-Raf mutations are found within the kinase domain, with a single substitution (V600E) accounting for at least 80%. The mutated B-Raf proteins activate the Raf-MEK-ERK pathway either via elevated kinase activity towards MEK or via activating C-Raf.

Therefore, development of a kinase inhibitor for B-Raf provides a new therapeutic opportunity for treatment of many types of human cancers, especially for metastatic melanomas, solid tumors, brain tumors such as Glioblastoma multiform (GBM), acute myelogenous leukemia (AML), lung cancer; papillary thyroid carcinoma, ovarian low-grade carcinoma, and colorectal cancer. Several Raf kinase inhibitors have been described as exhibiting efficacy in inhibiting tumor cell proliferation in vitro and/or in vivo assays (see, for example, U.S. Pat. Nos. 6,391,636, 6,358,932, 6,037,136, 5,717,100, 6,458, 813, 6,204,467, and 6,268,391). Other patents and patent applications suggest the use of Raf kinase inhibitors for treating leukemia (see, for example, U.S. Pat. Nos. 6,268,391, 6,204,467, 6,756,410, and 6,281,193; and abandoned U.S. Patent Application Nos. 20020137774 and 20010006975), or for treating breast cancer (see, for example, U.S. Pat. Nos. 6,358,932, 5,717,100, 6,458,813, 6,268,391, 6,204,467 and 6,911,446). Data demonstrates that Raf kinase inhibitors can significantly inhibit signaling through the MAPK pathway, leading to dramatic shrinkage in B-Raf (V600E) tumors.

The compounds of the present invention inhibit cellular processes involving B-Raf kinase by blocking the signal cascade in these cancer cells and ultimately inducing stasis and/ or death of the cells.

In accordance with the foregoing, the present invention further provides a method for preventing or treating lung carcinoma, prostate cancer, gastric cancer, pancreatic carcinoma, bladder carcinoma, colon carcinoma, myeloid disorders, prostate cancer, thyroid cancer, melanoma, adenomas and carcinomas of the ovary, eye, liver, biliary tract, and nervous system. Further, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 30 mg/kg per body weight. An indicated daily dosage in the larger mammal, e.g. humans, is in the range from about 0.5 mg to about 2000 mg, conveniently administered, e.g. in divided doses up to four times a day or in retard form. Suitable unit dosage forms for oral administration comprise from ca. 1 to 500 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. For example, compounds of the invention can be formulated into a microemulsion pre concentrate (MEPC). Compounds of Formula I can be prepared at 40 mg/ml in a mixture of 56% PEG400, 29% cremophor EL and 15% oleic acid. The mixture, without a compound of Formula I, is first prepared by vortexing/shaking. A compound of the invention is added and sonication is used to disperse the powder into the vehicle. The mixture is heated to 80° C. in a water bath for about an hour stirring, with sonication, every 15 minutes. This mixture is physically and chemically stable at room temperature for about one week.

Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other anti-tumor or anti-proliferative agents, for example, mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens, an anti-angiogenesis agent, kinase inhibitor, pan kinase inhibitor or growth factor inhibitor.

Compounds of the invention can be administered in therapeutically effective amounts in combination with one or more suitable excipients selected from corn starch, potato starch, tapioca starch, starch paste, pre-gelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

An embodiment of the invention is a method of claim 12 or 13, further comprising administering to the subject an additional therapeutic agent. The additional therapeutic agent comprises an anticancer drug, a pain medication, an antiemetic, an antidepressant or an anti-inflammatory agent. Further, the additional therapeutic agent is a different Raf kinase inhibitor or an inhibitor of MEK, mTOR, HSP90, AKT, PI3K, CDK9, PAK, Protein Kinase C, a MAP kinase, a MAPK Kinase, or ERK and is administered to the subject concurrently with a compound of the invention.

For example, the addition of a MEK inhibitor in combination with a Raf inhibitor leads to a significant inhibition of ERK signaling and consequently a decrease in cellular proliferation and transformation. Since MEK inhibitor treatments alone have led to dose limiting toxicities in the clinic, a Raf plus MEK inhibitor combination represents a superior treatment strategy. Examples of MEK inhibitors are AS703026 (EMD Serono); MSC1936369B (EMD Serono); GSK1120212 (GlaxoSmithKline); AZD6244 (Memorial Sloan-Kettering Cancer Center); PD-0325901 (Pfizer); ARRY-438162 (Array BioPharma); RDEA119 (Ardea Biosciences, Inc.); GDC0941 (Genentech); GDC0973 (Genentech); TAK-733 (Millennium Pharmaceuticals, Inc.); RO5126766 (Hoffmann-La Roche); and XL-518 (Exelixis).

In another embodiment of the invention are combinations and methods of treating cancer comprising a therapeutically effective amount of a compound of the Summary of the Invention (Raf inhibitor) and at least one MEK protein kinase inhibitor.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

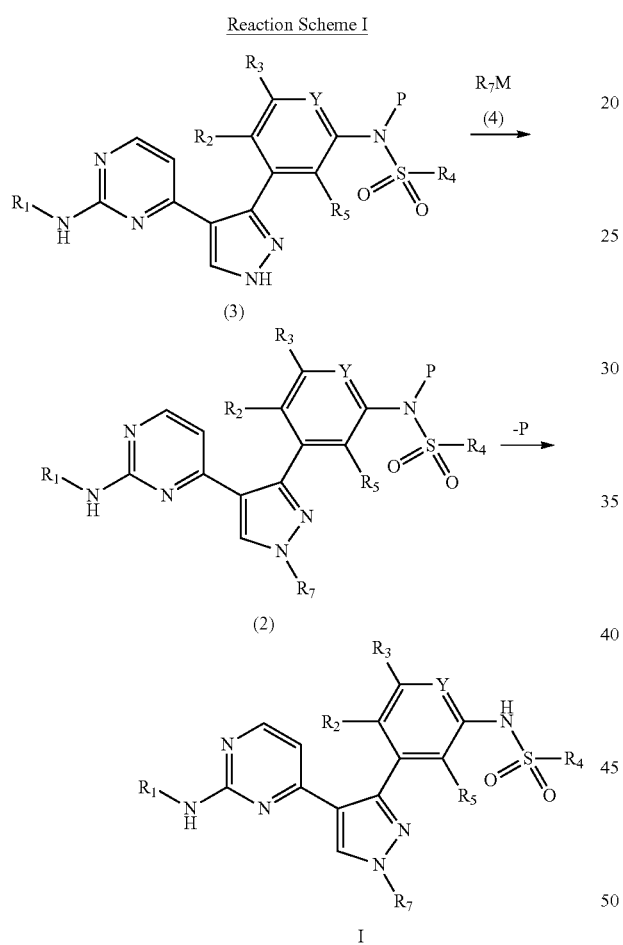

in which $R_1$, $R_2$, $R_3$, $R_4$, $R_5$, $R_7$, and Y are as defined in the Summary of the Invention, P is a suitable protecting group (for example, MEM, MOM, SEM, $R_4SO_2$, and the like), and M is a leaving group (for example, chloro, bromo, iodo, methanesulfonyloxy, p-toluenesulfonyloxy, and the like). A compound of Formula I can be synthesized by removal of protecting group P from a compound of Formula 2 (for example, by treatment with a strong acid such as hydrogen chloride in the presence of a protic solvent such as methanol or water when P is MEM, MOM, or SEM; or by treatment with aqueous or methanolic sodium or potassium carbonate, optionally in the presence of a cosolvent such as toluene, when P is a second sulfonyl group $R_4SO_2$).

Compounds of Formula 2 can be prepared by reacting a compound of Formula 3 with an alkylating agent of Formula 4 in the presence of a suitable solvent (for example, DMF, DMSO, and the like) and a suitable base (for example, potassium carbonate, sodium hydride, and the like). The reaction proceeds in a temperature range of about 0° C. to about 150° C. and can take up to about 24 hours to complete. The reaction mixture is optionally further reacted to remove any protecting groups.

Compounds of Formula I can also be prepared by proceeding as in the following Reaction Scheme II:

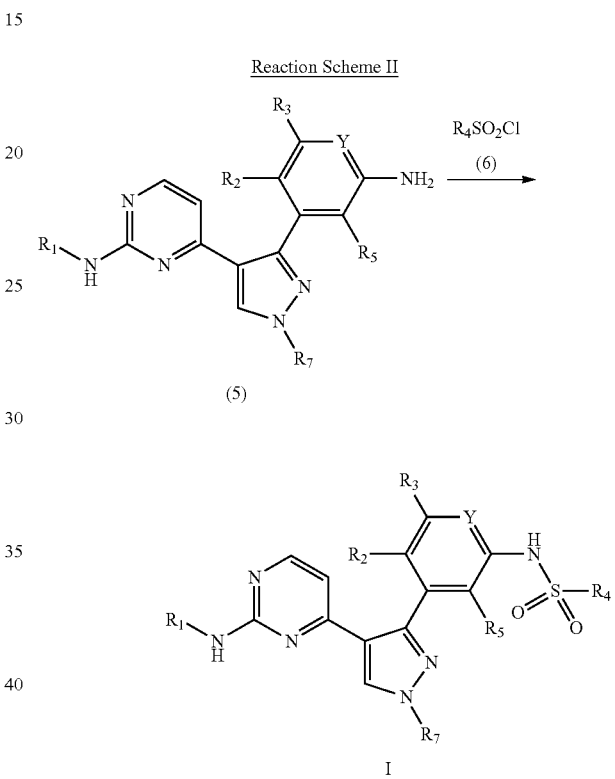

in which $R_1$, $R_2$, $R_3$, $R_4$, $R_5$, and Y are as defined in the Summary of the Invention. A compound of Formula I can be synthesized by reacting a compound of Formula 5 with a sulfonylating reagent of Formula 6 in the presence of a suitable base (for example, pyridine, triethylamine, 4-(N,N-dimethylamino)pyridine, and the like) and a suitable solvent (such as pyridine, dichloromethane, 2-methylTHF, and the like). The reaction proceeds in a temperature range of about 0° C. to about 100° C. and can take up to about 24 hours to complete. The reaction mixture is optionally further reacted to remove any protecting groups. In some instances, the sulfonylating reagent can react twice to produce a bis-sulfonyl derivative. In this instance, the bis-sulfonyl compound can be converted to a compound of Formula a by treatment with a suitable base (for example, sodium or potassium hydroxide, or sodium or potassium carbonate) in the presence of a protic solvent such as methanol or water, optionally in the presence of a cosolvent such as toluene or 2-methylTHF. The reaction takes place in a temperature range of about 20° C. to about 100° C. and can take up to about 24 hours to complete.

Compounds of Formula I can also be prepared by proceeding as in the following Reaction Scheme III:

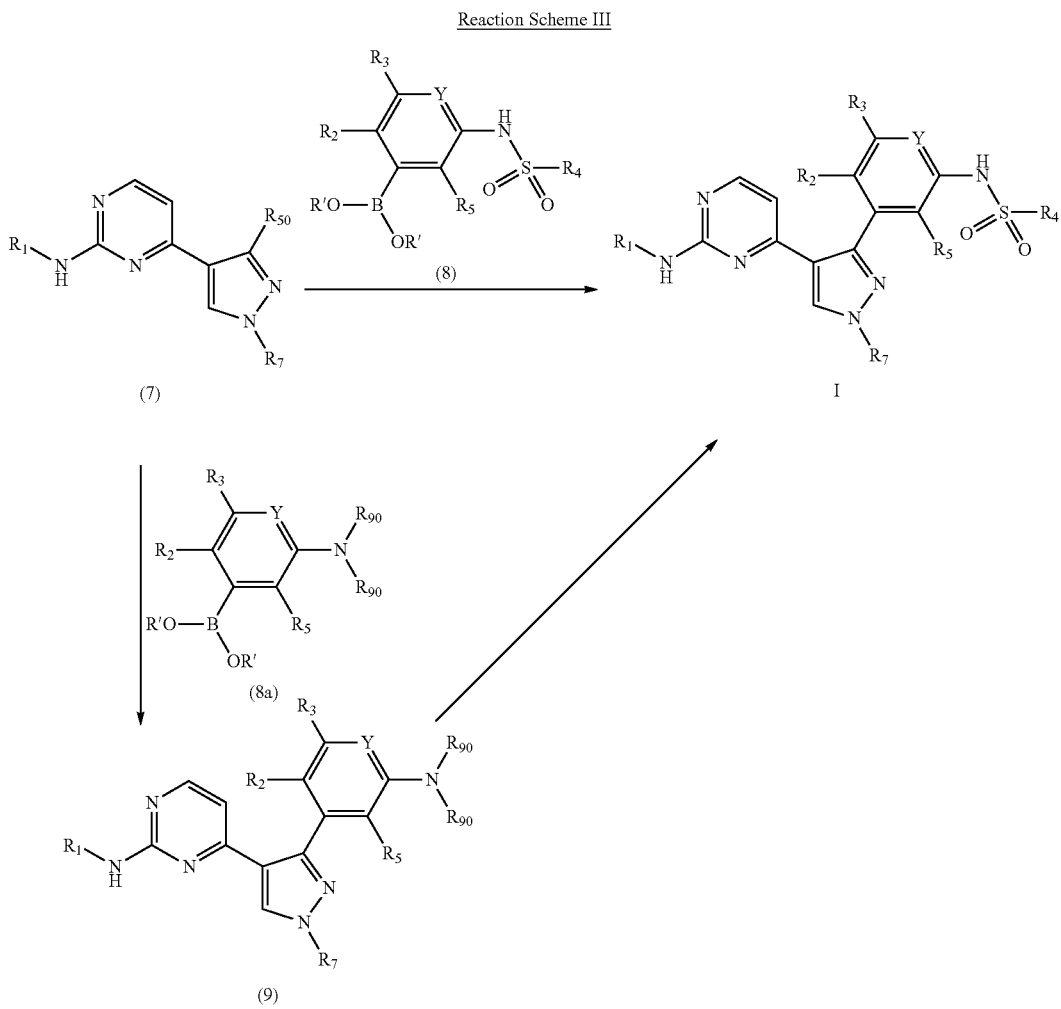

in which $R_1$, $R_2$, $R_3$, $R_4$, $R_5$, and Y are as defined in the Summary of the Invention, $R_{50}$ is a leaving group (for example, iodo, bromo, chloro, trifluoromethanesulfonyloxy, and the like), each R' can be, for example hydrogen, methyl, and the like, or the two R' groups can be joined together to form a cyclic boronate ester. The two $R_{90}$ groups can each be hydrogen, or the two $R_{90}$ groups, taken together, can represent a suitable nitrogen protecting group (for example, one $R_{90}$ can be hydrogen and the other can be BOC). A compound of Formula Ia can be synthesized by reacting a compound of Formula 7 with a compound of Formula 8 in the presence of a suitable transition metal catalyst (for example, tetrakis (triphenylphosphinepalladium)(0) or $PdCl_2(dppf)$, a suitable solvent (for example, DME, dioxane, toluene, ethanol, and the like) and a suitable base (for example, anhydrous potassium carbonate or aqueous sodium carbonate solution, and the like). The reaction proceeds in a temperature range of about 20° C. to about 120° C. and can take up to about 24 hours to complete. The reaction mixture is optionally further reacted to remove any protecting groups.

A compound of Formula 1 can also be prepared by a similar Suzuki reaction protocol in which a compound of Formula 7 is reacted with a compound of Formula 8a to generate a compound of Formula 9. Following deprotection of the $R_{90}$ groups, a sulfonylation reaction, as described for Reaction Scheme II, generates a compound of Formula Ia.

It will be appreciated by one skilled in the art that other organometallic coupling reactions, for example using tin reagents (Stille coupling) or zinc reagents (Negishi coupling), might also be employed in place of the Suzuki coupling reaction using boron reagents described in Reaction Scheme III.

Compounds of Formula 7 can be prepared by proceeding as in the following Reaction Scheme IV:

Reaction Scheme IV

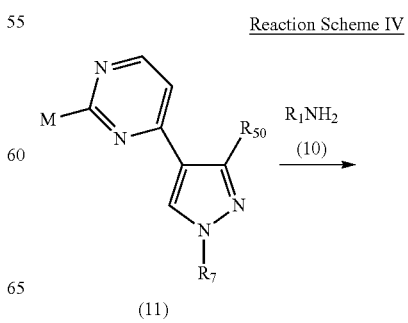

-continued

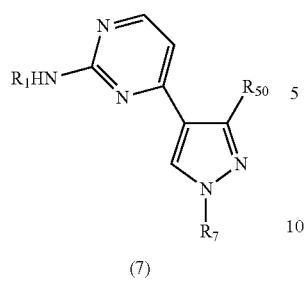

(7)

In this instance, M is a leaving group (for example, chloro, bromo, iodo, methanesulfonyl, and the like), $R_{50}$ is a leaving group (for example, iodo, bromo, chloro, trifluoromethanesulfonyloxy, and the like), and $R_7$ is as defined in the Summary of the Invention. A compound of Formula 7 can be prepared by reacting an amine compound of Formula 10 with a compound of Formula 11. The reaction is performed in the presence of a suitable base (for example, triethylamine, potassium carbonate, and the like) in a solvent such as isopropanol, DMSO, NMP, or dioxane at a temperature from about 25 to about 120° C. In some instances further transformations of the newly-introduced $R_1$ group may subsequently be performed to arrive at the final intended $R_1$ group.

Compounds of Formula 11a, which are a subset of compounds of Formula 11 in which M is methanesulfonyl, can be prepared by proceeding as in the following Reaction Scheme V:

Reaction Scheme V

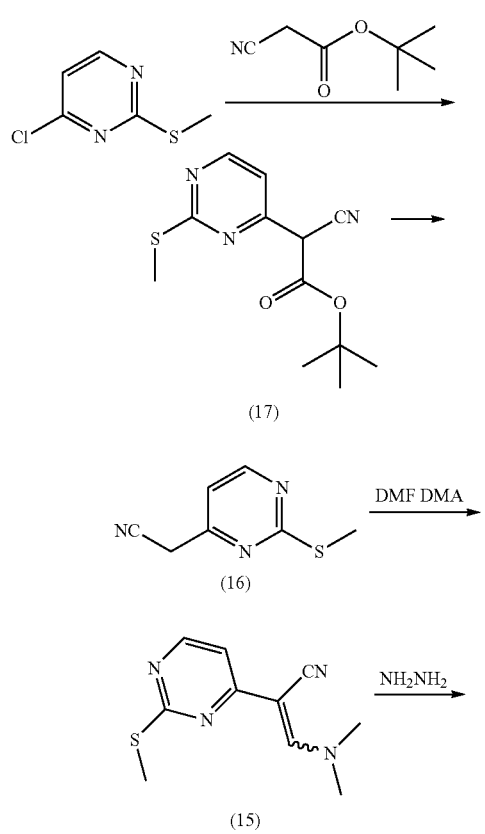

-continued

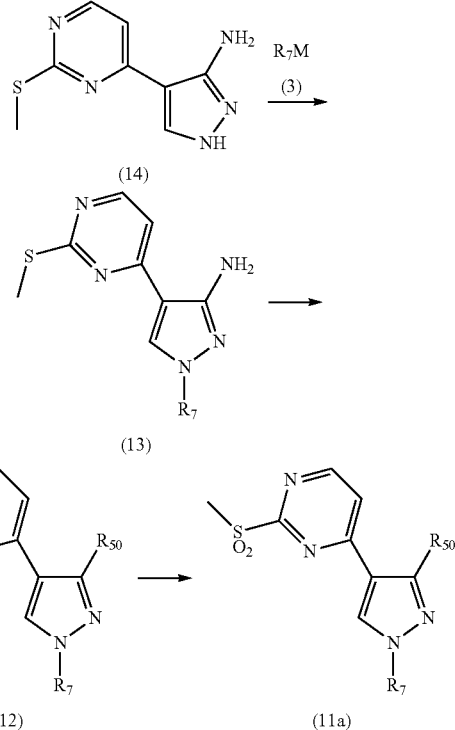

In which $R_7$ and $R_{50}$ are as defined in the Summary of the Invention. A compound of Formula 11a can be prepared by reacting a compound of Formula 12 with a suitable oxidizing system (for example, m-chloroperbenzoic acid in a solvent of dichloromethane, or Oxone™ in aqueous methanol, and the like), at a temperature of about −78° C. to about 50° C. The reaction takes up to about 24 hours to complete.

A compound of Formula 12 in which $R_{50}$ is chloro, bromo, or iodo can in turn be prepared by reacting an amine compound of Formula 13 with a suitable diazotization reagent system (for example, nitrous acid in conjunction with a copper (I) halide salt, isoamyl nitrite in conjunction with copper (I) iodide/methylene iodide, isoamyl nitrite in conjunction with boron trifluoride, iodine, and potassium iodide in acetonitrile, and the like). The reaction takes place at a temperature of about 0 to about 80° C., and takes from about 1 to about 6 hours to complete.

A compound of Formula 13 can be prepared by reacting a compound of Formula 14 with a compound of Formula 3, as described for Reaction Scheme I.

A compound of Formula 14 can be prepared by cyclization of an enaminonitrile compound of Formula 15 with hydrazine or a hydrazine salt in a suitable solvent (for example, ethanol and the like). The reaction takes place at a temperature of about 25 to about 100° C., and can take from about 1 hour to about 24 hours to complete.

Alternatively, a compound of Formula 13 can be prepared from a compound of Formula 15 in a one-step procedure by reacting a compound of Formula 15 with a monosubstituted hydrazine $R_7NH-NH_2$. The reaction takes place at a temperature of about 25 to about 100° C., and can take from about 1 hour to about 24 hours to complete.

A compound of Formula 15 can in turn be prepared by reaction of a compound of Formula 16 with DMF DMA or Bredereck's reagent, optionally in the presence of a co-solvent such as DMF, at a temperature of about 50 to about 150° C. The reaction takes about 1 to about 24 hours to complete.

A compound of Formula 16 can be prepared by treatment of a compound of Formula 17 with a suitable acid (for example, p-toluenesulfonic acid, and the like) in a suitable inert solvent (for example, toluene, and the like). The reaction takes place at a temperature of about 50 to about 120° C., and takes about 1 to about 24 hours to complete.

25 to about 80° C. The reaction takes from about 1 to about 24 hours to complete.

Compounds of Formula 11b, which are a subset of compounds of Formula 11 in which M is a halogen, can be prepared by proceeding as in the following Reaction Scheme VI:

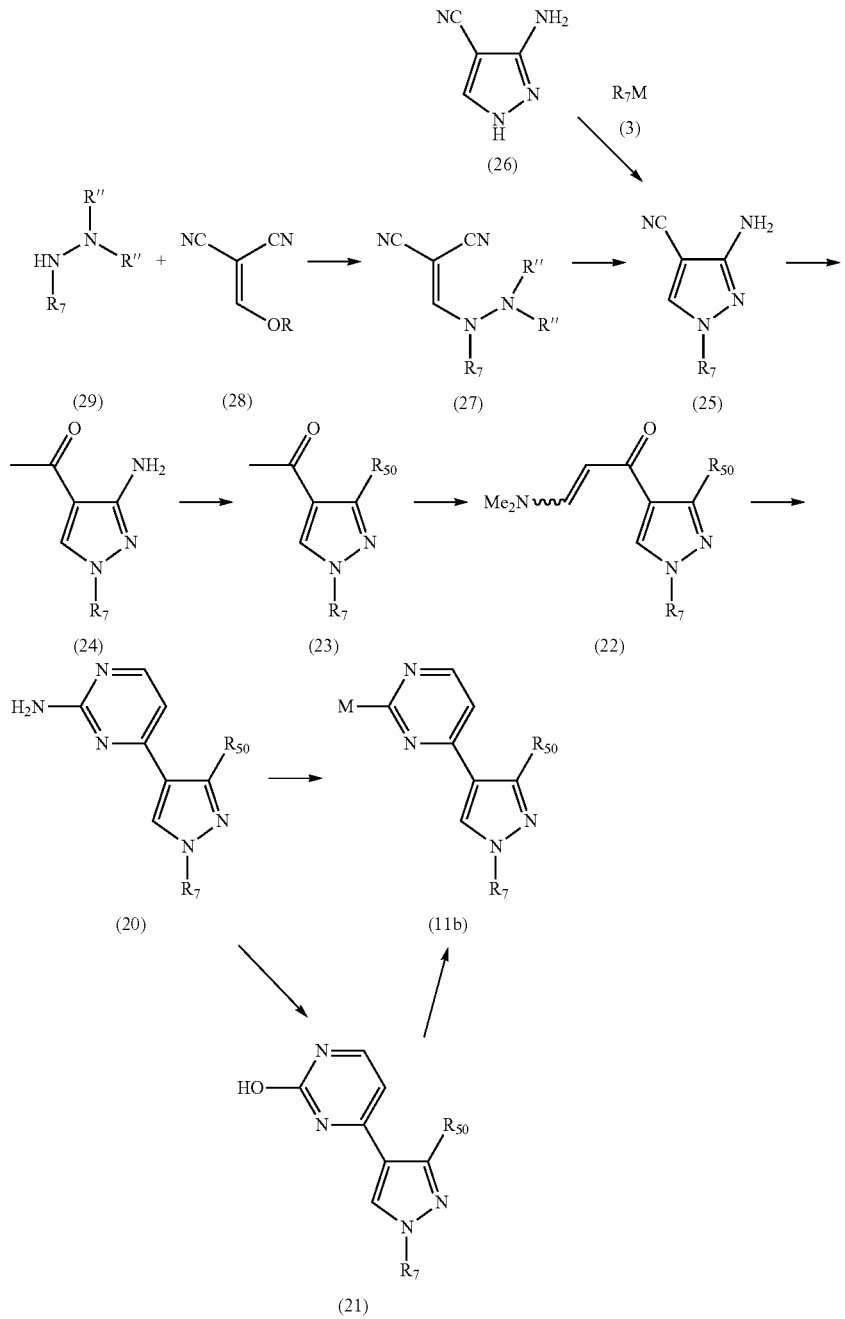

Finally, a compound of Formula 17 can be prepared by reaction of 4-chloro-2-(methylthio)pyrimidine with tert-butyl cyanoacetate in the presence of a suitable base (for example, sodium hydride and the like) and a suitable solvent (for example, DMSO and the like), at a temperature of about in which $R_7$ and $R_{50}$ are as defined in the Summary of the Invention. A compound of Formula 11b, in which M is a halogen, can be prepared by reacting a compound of Formula 20 with a suitable diazotization reagent system (for example, nitrous acid in conjunction with a copper (I) halide salt, sodium nitrite in conjunction with p-toluenesulfonic acid and potassium iodide. The reaction takes place at a temperature of about 0 to about 80° C., and takes from about 1 to about 6 hours to complete. Alternatively, treatment of a compound of Formula 20 with a diazotization reagent (for example, sodium nitrite and the like) in the presence of a carboxylic acid (for example, trifluoroacetic acid and the like) at 0 to 40° C. for a period of about 0.5 to about 6 hours, followed by treatment with a basic aqueous solution (for example aqueous potassium carbonate solution and the like) provides a compound of Formula 21 (such a compound may exist in tautomeric forms). Subsequent treatment of a compound of Formula 21 with a chlorinating agent (for example, phosphorous oxychloride and the like), optionally in the presence of a base such as N,N-dimethylaniline or DIPEA, and optionally in the presence of an inert solvent such as acetonitrile or toluene, and an additive such as DMF, at a temperature of about 50 to about 110° C., and for a time of about 1 to about 72 hours, provides a compound of Formula 11b, in which M is chlorine.

A compound of Formula 20 can in turn be prepared by reaction of a compound of Formula 22 with guanidine or a guanidine salt (for example, guanidine hydrochloride or guanidine carbonate), optionally in the presence of a base (for example, lithium hydroxide and the like) in a suitable solvent (for example, sec-butanol, NMP and the like), at a temperature from about 50 to about 180° C., and for a time of about 2 to about 48 hours.

A compound of Formula 22 can be prepared by reaction of a compound of Formula 23 with DMF DMA or Bredereck's reagent, optionally in the presence of a co-solvent such as DMF, at a temperature of about 50 to about 150° C. The reaction takes about 1 to about 24 hours to complete.

A compound of Formula 23 in which $R_{50}$ is chloro, bromo, or iodo can be prepared by reacting an amine compound of Formula 24 with a suitable diazotization reagent system (for example, nitrous acid in conjunction with a copper (I) halide salt, sodium nitrite in conjunction with p-toluenesulfonic acid and potassium iodide, or isoamylnitrite in conjunction with boron trifluoride-THF, iodine, potassium iodide, and acetonitrile). The reaction takes place at a temperature of about 0 to about 80° C., and takes from about 1 to about 6 hours to complete.

A compound of Formula 24 can in turn be prepared by reacting a compound of Formula 25 with an organometallic reagent such as methyllithium, methyllithium-lithium bromide complex, or a methylmagnesium halide reagent, in an inert solvent such as THF, ether, or cyclopropyl methyl ether, at a temperature of about 0 to about 100° C., followed by treatment with an aqueous quenching solution. The reaction takes from about 2 to about 48 hours to complete.

A compound of Formula 25 can be prepared by reacting a compound of Formula 26 with a compound of Formula 3, as described for Reaction Scheme I. Alternatively, a compound of Formula 25 can be prepared from a compound of Formula 27, in which the two R" groups taken together form an acid-labile protecting group (for example, an imine such as benzylidene or a carbamate such as t-butylcarbamate). The reaction is carried out by treatment of a compound of Formula 27 with an aqueous acidic reagent (for example, concentrated hydrochloric acid and the like) in a solvent such as ethanol, at a temperature of about 25 to about 100° C. Preferably the two R" groups, taken together, form an imine such as benzylidine.

A compound of Formula 27 can in turn be prepared by reacting a compound of Formula 28 with a compound of Formula 29, in which the two R" groups taken together form an acid-labile protecting group (for example, an imine such as benzylidene or a carbamate such as t-butylcarbamate). The reaction is performed in a solvent (for example toluene, methanol, or ethanol) at a temperature of about 25 to about 120° C., optionally in the presence of a catalyst such as DMAP, and takes about 1 to about 24 hours to complete. Optionally, the reaction is performed in an inert solvent (for example, THF and the like) in the presence of a base (for example n-butyllithium and the like) at a temperature of about −80 to about 25° C., over a time of about 0.5 to about 12 hours.

A compound of Formula 29 can be prepared by methods known to those skilled in the art. For example, a compound of Formula 29, in which the two R" groups taken together form a benzylidene group, can be prepared by reaction of benzaldehyde with a mono-substituted hydrazine $R_7NHNH_2$, in a solvent such as ethanol or toluene, for about 1 to about 24 hours, and at a temperature of about 25 to about 120° C. Alternatively, the reaction can be carried out using a mono-substituted hydrazine salt (for example, a hydrochloride salt or an oxalate salt, and the like), in conjunction with a base (for example sodium acetate or triethylamine).

Compounds of Formula 8 or Formula 8a can be prepared as described in the following Reaction Scheme VII:

Reaction Scheme VII

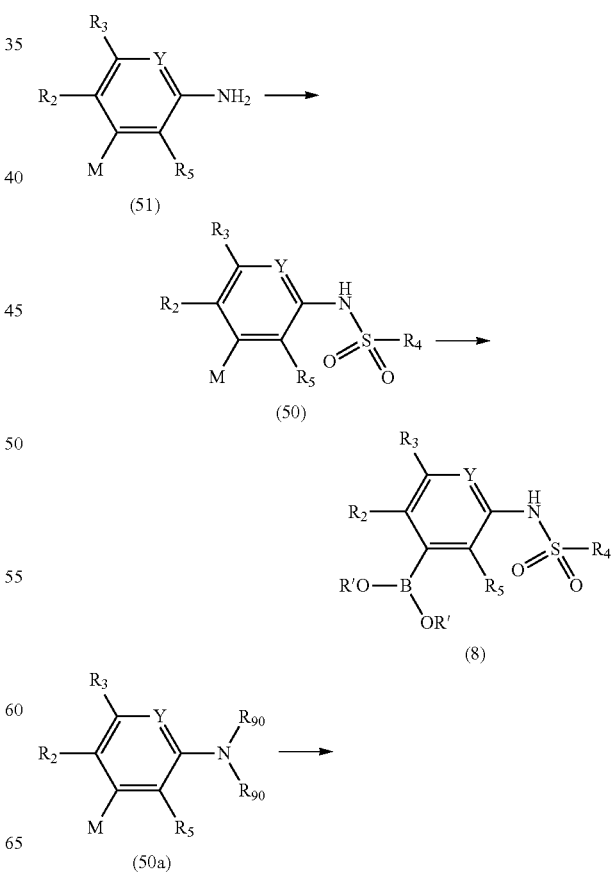

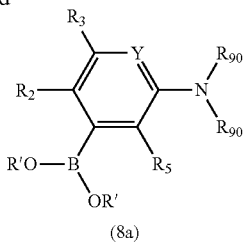

in which $R_2$, $R_3$, $R_4$, $R_5$, and Y are as defined in the Summary of the Invention, M is a leaving group (for example, iodo, bromo, chloro, trifluoromethanesulfonyloxy, and the like), and each R' can be, for example hydrogen, methyl, and the like, or the two R' groups can be joined together to form a cyclic boronate ester. The two $R_{90}$ groups can each be hydrogen, or the two $R_{90}$ groups, taken together, can represent a suitable nitrogen protecting group (for example, one $R_{90}$ can be hydrogen and the other can be BOC). Compounds of Formula 8 or Formula 8a can be prepared by reaction of a compound of Formula 50 or Formula 50a, respectively, with a diboron compound (for example, bis(pinacolato)diboron and the like) in the presence of a suitable transition metal catalyst (for example $PdCl_2(dppf)$),) and a suitable base (for example, potassium acetate and the like) in a suitable solvent (for example, toluene, dioxane and the like). The reaction proceeds in a temperature range of about 20° C. to about 120° C. and can take up to about 24 hours to complete. A compound of Formula 50 can in turn be prepared by sulfonylation of a compound of Formula 51 as described for Reaction Scheme II. It will be appreciated by one skilled in the art that compounds of Formula 51 or Formula 50a, for example, 3-bromoanilines, or N—BOC-protected 3-bromoanilines, can be prepared by a variety of methods, including, but not limited to, those described further in the Examples below.

A compound of Formula 70 can be prepared as described in the following Reaction Scheme VIII:

Reaction Scheme VIII

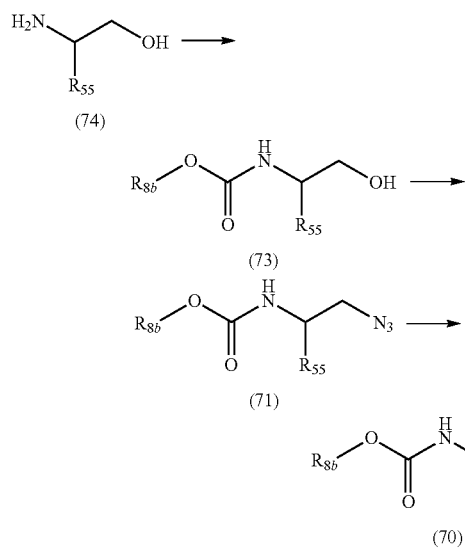

in which $R_{8b}$ is as defined in the Summary of the Invention and $R_{55}$ is selected from a $C_{1-4}$alkyl or halo-substituted-$C_{1-4}$alkyl. A compound of Formula 70 can be prepared by treatment of a compound of Formula 71 with a suitable reducing system (for example, hydrogenation over a palladium catalyst, and the like) in a suitable solvent (for example, ethanol or ethyl acetate) at a temperature of about 25 to about 75° C., over a period of about 0.5 to about 12 hours.

A compound of Formula 71 can in turn be prepared by a two step process consisting of conversion of the hydroxy group of a compound of Formula 73 to a suitable leaving group, followed by displacement with azide anion. For the first step, suitable reagents include phosphorous tribromide, or methanesulfonyl chloride in combination with a suitable base such as triethylamine. The reactions are carried out in a suitable solvent (for example, dichloromethane, and the like), at a temperature of about 0 to about 50° C. For the second step, the displacement is carried out with an azide reagent (for example, sodium azide, and the like) in a suitable solvent (for example, DMF or DMSO) at a temperature from about 25 to about 150° C. The reaction takes from about 1 to about 24 hours to complete. Alternatively, the transformation can be carried out in one step by treatment of a compound of Formula 73 with a phosphine reagent (for example, triphenylphosphine, and the like) and an azodicarboxylate reagent (for example, diethylazodicarboxylate and the like) in the presence of hydrazoic acid (formed in situ from an azide salt, such as sodium azide, and an acid). The reaction takes place at a temperature of about −80° C. to about 75° C., and takes about 1 to about 24 hours to complete.

A compound of Formula 73 can be prepared by treatment of a compound of Formula 74 with a chloroformate (for example, methyl chloroformate and the like) or an alternative alkoxycarbonylation reagent such as di-tert-butyldicarboxylate. The reaction takes place in an inert solvent (for example, dichloromethane and the like) at a temperature of about −80 to about 25° C., and takes about 1 to about 12 hours to complete. A base such as triethylamine may optionally be used. The reaction can also be performed in a two-phase system consisting of a solvent such as THF or dioxane, and an aqueous basic solution, such as aqueous sodium bicarbonate solution, at a temperature of about 25° C., for a period of about 2 to about 16 hours.

A compound of Formula 70 can also be prepared as described in the following Reaction Scheme IX:

Reaction Scheme IX

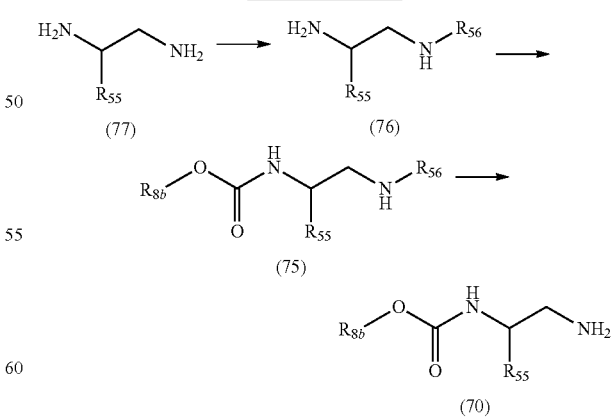

in which $R_{8b}$ is as defined in the Summary of the Invention, $R_{55}$ is selected from a $C_{1-4}$alkyl or halo-substituted-$C_{1-4}$alkyl, and $R_{56}$ is a suitable protecting group, for example, benzyloxycarbonyl (CBz). A compound of Formula 70 can be prepared by deprotection of a compound of Formula 75. For example, a compound of Formula 70 can be prepared by treatment of a compound of Formula 75, in which $R_{56}$ is Cbz, with a suitable reducing system (for example, hydrogenation over a palladium catalyst, and the like) in a suitable solvent (for example, ethanol, methanol, MTBE, or ethyl acetate) at a temperature of about 25 to about 75° C., optionally in the presence of an acid such as hydrogen chloride, over a period of about 0.5 to about 12 hours. Alternatively, the deprotection can be carried out under transfer hydrogenation conditions, using a suitable hydrogen donor such as formic acid, ammonium formate, or 1,4-cyclohexadiene. A compound of Formula 75 can in turn be prepared by reaction of a compound of Formula 76 with a chloroformate (for example, methyl chloroformate and the like) or an alternative alkoxycarbonylation reagent such as di-tert-butyldicarboxylate. The reaction takes place in an inert solvent (for example, dichloromethane and the like) at a temperature of about −80 to about 25° C., and takes about 1 to about 24 hours to complete. A base such as triethylamine may optionally be used. The reaction can also be performed in a two-phase system consisting of a solvent such as THF or dioxane, and an aqueous basic solution, such as aqueous sodium bicarbonate solution, at a temperature of about 25° C., for a period of about 2 to about 16 hours. A compound of Formula 76 can be prepared by protection of a compound of Formula 77. The protection conditions can be chosen to provide preferentially or substantially the single isomer of Formula 76. Alternatively, conditions can be chosen in which little or no preference for formation of the single isomer of Formula 77 is shown, but in which a compound of Formula 76 can nevertheless be isolated in sufficient purity for further use. Means of obtaining such purity can include crystallization of either the free base or a salt. A compound of Formula 76, in which $R_{56}$ is Cbz, can be prepared by treatment of a compound of Formula 77 with benzyl chloroformate. The reaction takes place in an inert solvent (for example, dichloromethane and the like) at a temperature of about −80 to about 25° C., and takes about 1 to about 24 hours to complete. A base such as triethylamine may optionally be used. The reaction can also be performed in a two-phase system consisting of a solvent such as THF or dioxane, and an aqueous basic solution, such as aqueous sodium bicarbonate solution, at a temperature of about 25° C., for a period of about 2 to about 24 hours. A salt of a compound of Formula 77 can be used, in conjunction with a base such as triethylamine or sodium carbonate, as input in place of the free base.

It will be appreciated by one skilled in the art that a compound of Formula 70 can be either a single enantiomer or a mixture of enantiomers, and that a single enantiomer compound of Formula 70 can be obtained by starting with an appropriate single enantiomer compound of Formula 74 or Formula 77.

Detailed examples of the synthesis of a compound of Formula Ia can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I to IX; and
(b) optionally converting a compound of the invention into a pharmaceutically acceptable salt;
(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer, for example stereoisomer, of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

Abbreviations used are as follows: benzyloxycarbonyl (Cbz); tert-butoxycarbonyl (BOC); Cell proliferation (CP); dichloromethane (DCM); N,N-di-isopropylethylamine (DIPEA); [1,1'-Bis(diphenylphosphino)ferrocene]dichloropalladium(II) (PdCl$_2$(dppf)); 1,2-dimethoxyethane (DME); N,N-dimethyl acetamide (DMA); N,N-dimethylaminopyridine (DMAP); N,N-dimethyl formamide (DMF); N,N-dimethyl formamide dimethylacetal (DMF DMA); dimethylsulfoxide (DMSO); ethyl acetate (EtOAc); high pressure liquid chromatography (HPLC); isopropyl acetate (iPrOAc); methanesulfonyl (Ms); 2-methyltetrahydrofuran (2-methylTHF); N-methylpyrrolidinone (NMP); tetrahydrofuran (THF); thin layer chromatography (TLC); and para-toluenesulfonic acid (pTsOH).

Intermediate.
Cyano-(2-methylthio-pyrimidin-4-yl)-acetic acid tert-butyl ester

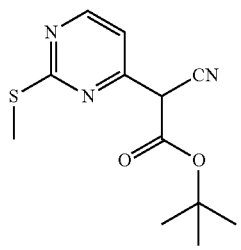 [SMILES: CSc1nccc(C(C#N)C(=O)OC(C)(C)C)n1]

To a suspension of sodium hydride (7.15 g, 179 mmol, 60% in oil) in DMSO (100 mL) was added tert-butyl cyanoacetate (24.8 g, 170 mmol) at 23° C. After the evolution of hydrogen ceased, 4-chloro-2-methylthiopyrimidine (13.7 g, 85 mmol) was added. The reaction was heated at 80° C. for 16 h. The reaction mixture was then cooled to room temperature and quenched with ice-cooled saturated ammonium chloride (300 mL). The solid was filtered and washed with water (2×200 mL). 300 mL of hexane was added to the solid and the suspension was heated at 60° C. for 1 h and then cooled to room temperature. The solid was filtered and washed with hexane to afford the title compound; $^1$H NMR 400 MHz (CDCl$_3$) δ 7.82 (d, 1H), 6.74 (d, 1H), 2.63 (s, 3H), 2.61 (s, 1H), 1.52 (s, 9H); MS m/z: 266.0 (M+1).

Intermediate.
(2-Methylthio-pyrimidin-4-yl)-acetonitrile

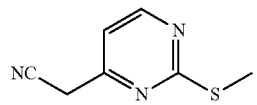

To a solution of Intermediate cyano-(2-methylthio-pyrimidin-4-yl)-acetic acid tert-butyl ester (5.3 g, 20 mmol) in anhydrous toluene (100 mL) was added p-toluenesulfonic acid (800 mg). The mixture was heated to reflux for 8 h, cooled to room temperature and extracted with ethyl acetate. The organic layer was washed with 1N aqueous sodium hydroxide solution and brine, dried over sodium sulfate, filtered and concentrated. The crude product was purified by silica gel chromatography (3:1 hexanes/ethyl acetate eluant) to afford the title compound: $^1$H NMR 400 MHz (CDCl$_3$) δ 8.56 (d, 1H), 7.12 (d, 1H), 3.84 (s, 2H), 2.57 (s, 3H); MS m/z: 166.0 (M+1).

Intermediate. 4-(2-(Methylthio)pyrimidin-4-yl)-1H-pyrazol-3-amine

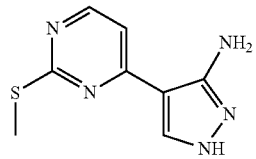

Step 1. 3-(Dimethylamino)-2-(2-(methylthio)pyrimidin-4-yl)acrylonitrile. N,N-Dimethylformamide dimethyl acetal (30 mL) was added to Intermediate (2-Methylthio-pyrimidin-4-yl)-acetonitrile (2.62 g, 15.7 mmol) and the mixture was heated at 100° C. for 16 h. The cooled reaction mixture was concentrated, and the residue was used without further purification.

Step 2. 4-(2-(Methylthio)pyrimidin-4-yl)-1H-pyrazol-3-amine. A mixture of crude 3-(dimethylamino)-2-(2-(methylthio)pyrimidin-4-yl)acrylonitrile from the previous step (entire amount) and hydrazine monohydrate (2.36 mL, 47 mmol) in anhydrous ethanol (75 ml) was heated at 80° C. for 16 hours. The reaction mixture was cooled to room temperature and concentrated. The reaction mixture was partitioned between ethyl acetate and brine. The organic layer was separated and washed with brine, dried over sodium sulfate, filtered and concentrated. The crude product was purified by silica gel chromatography (2 to 5% methanol in dichloromethane eluant) to afford 4-(2-(methylthio)pyrimidin-4-yl)-1H-pyrazol-3-amine: $^1$H NMR 400 MHz (DMSO-d$_6$) δ

11.9 (s, 1H), 8.3 (s, 1H), 7.87 (s, 1H), 7.23 (s, br 1H), 6.43 (s, 1H), 5.74 (s, 1H), 2.53 (s, 3H); MS m/z: 208.0 (M+1).

Intermediate. 1-Isopropyl-4-(2-(methylthio)pyrimidin-4-yl)-1H-pyrazol-3-amine

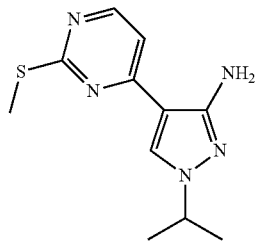 [SMILES: CSc1nccc(-c2cn(C(C)C)nc2N)n1]

Intermediate 4-(2-(Methylthio)pyrimidin-4-yl)-1H-pyrazol-3-amine (10.0 g, 40 mmol) was dissolved in THF (200 mL), followed by addition of 2-iodopropane (6.3 mL, 63 mmol) and sodium methoxide (25% weight solution in methanol, 14.3 ml, 63 mmol). The mixture was heated at 50° C. with stirring under a nitrogen atmosphere for 3 d, then was concentrated under vacuum. The residue was taken up in ethyl acetate (200 mL) and washed with aqueous potassium carbonate solution and brine, then dried over sodium sulfate, filtered, and concentrated to provide a brown residue. The residue was chromatographed on silica gel (hexane/ethyl acetate eluant) to provide 1-isopropyl-4-(2-(methylthio)pyrimidin-4-yl)-1H-pyrazol-3-amine as a solid; $^1$H NMR 400 MHz (CDCl$_3$) δ 8.23 (d, J=5.6 Hz, 1H), 7.60 (s, 1H), 6.83 (d, J=5.6 Hz, 1H), 5.23 (d, J=2.8 Hz, 2H), 4.21-4.25 (m, 1H), 2.50 (s, 3H), 1.37 (d, J=6.8 Hz, 6H); MS m/z: 250.1 (M+1).

Similarly prepared were: 1-Ethyl-4-(2-(methylthio)pyrimidin-4-yl)-1H-pyrazol-3-amine and 1-Methyl-4-(2-(methylthio)pyrimidin-4-yl)-1H-pyrazol-3-amine.

Intermediate. 4-(3-Iodo-1-isopropyl-1H-pyrazol-4-yl)-2-(methylthio)pyrimidine

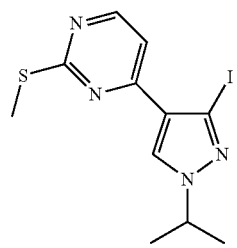 [SMILES: CSc1nccc(-c2cn(C(C)C)nc2I)n1]

A mixture of Intermediate 1-isopropyl-4-(2-(methylthio)pyrimidin-4-yl)-1H-pyrazol-3-amine (4.0 g, 16.0 mmol), isopentylnitrite (13.2 g, 112 mmol), and methylene iodide (30 mL) was heated at 100° C. for 3 h. Removal of the volatiles under vacuum provided a dark residue, which was purified by silica gel chromatography (2:1 hexane/ethyl acetate eluant) to afford the title compound as a solid; MS m/z: 361.1 (M+1).

Similarly prepared were: 4-(3-Iodo-1-ethyl-1H-pyrazol-4-yl)-2-(methylthio)pyrimidine; 4-(3-Iodo-1-methyl-1H-pyrazol-4-yl)-2-(methylthio)pyrimidine; and 4-(3-iodo-1H-pyrazol-4-yl)-2-(methylthio)pyrimidine.

Intermediate. 4-(3-Iodo-1-(tetrahydro-2H-pyran-2-yl)-1H-pyrazol-4-yl)-2-(methylthio)pyrimidine

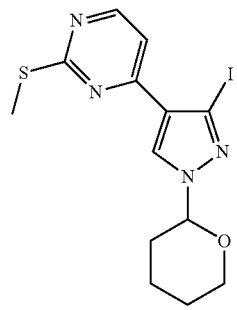 [SMILES: CSc1nccc(-c2cn(C3CCCCO3)nc2I)n1]

A solution of 4-(3-iodo-1H-pyrazol-4-yl)-2-(methylthio)pyrimidine (270 mg, 0.85 mmol) and p-toluenesulfonic acid monohydrate (32 mg, 0.17 mmol) in 3,4-dihydro-2H-pyran (1 ml) was heated at 60° C. for 5 h. The cooled mixture was diluted with ethyl acetate, and the mixture was washed with water and brine, and then dried over sodium sulfate, filtered, and concentrated. The residue was chromatographed on silica gel (10% ethyl acetate in hexanes eluant) to provide the title compound. MS (m/z): 402.7 (M+1).

Intermediate. 4-(3-Iodo-1-isopropyl-1H-pyrazol-4-yl)-2-(methylsulfonyl)pyrimidine

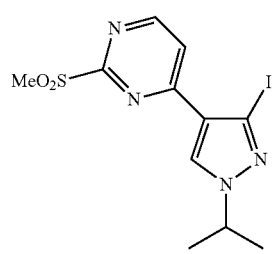 [SMILES: CC(C)n1cc(-c2ccnc(S(C)(=O)=O)n2)c(I)n1]

To a solution of Intermediate 4-(3-iodo-1-isopropyl-1H-pyrazol-4-yl)-2-(methylthio)pyrimidine (4.51 g, 12.5 mmol) in dichloromethane (60 mL) at 0° C. was added m-chloroperbenzoic acid (3.65 g, 77% purity, 16.3 mmol). The mixture was stirred at 0° C. under nitrogen for 3 h, then was diluted with ethyl acetate and washed with aqueous potassium carbonate solution and brine. The organic layer was dried over magnesium sulfate, filtered, and concentrated to provide 4-(3-iodo-1-isopropyl-1H-pyrazol-4-yl)-2-(methylsulfonyl)pyrimidine as a solid. MS m/z: 393.0 (M+1).

Similarly prepared were: 4-(3-Iodo-1-ethyl-1H-pyrazol-4-yl)-2-(methylsulfonyl)pyrimidine; and 4-(3-Iodo-1-methyl-1H-pyrazol-4-yl)-2-(methylsulfonyl)pyrimidine.

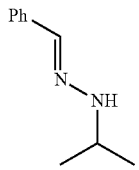

Intermediate. 1-Benzylidene-2-isopropylhydrazine

To a round-bottom flask containing anhydrous sodium acetate (8.2 g, 0.1 mol) in 125 ml 50% ethanol was added isopropylhydrazine HCl salt (11.1 g, 0.1 mole) and benzaldehyde (10.6 g, 0.1 mole). The mixture was stirred at rt for 20 h. The reaction was extracted with ether (3×250 ml). The organic layers were combined and washed with aqueous sodium bicarbonate solution and brine and dried over sodium sulfate. Filtration, concentration, and co-evaporation with toluene (3×) provided the title compound as an oil. MS m/z 163.3 (M+1).

Similarly prepared were: 1-Benzylidene-2-ethylhydrazine starting from ethylhydrazine oxalate, using methanol and triethylamine in place of ethanol and sodium acetate, respectively; and 1-Benzylidene-2-methylhydrazine starting from methylhydrazine, using methanol as solvent, with no added base.

Intermediate. 2-((2-Benzylidene-1-isopropylhydrazinyl)methylene)-malononitrile

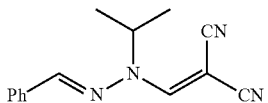

A solution of Intermediate 1-benzylidene-2-isopropylhydrazine (12.9 g, 0.079 mol) in 200 ml anhydrous THF was cooled in a dry ice/acetone bath under an argon atmosphere. To this solution was added n-butyllithium (1.6 M in hexanes, 66 ml, 0.106 mol) via syringe. Following completion of the addition, the mixture was stirred at dry-ice temperature for an additional 5 minutes. A solution of (2-(ethoxymethylene)malononitrile (13.6 g, 0.11 mol) in THF (30 ml) was added. The mixture was stirred at dry-ice temperature for 0.5 h, and then was quenched with saturated aqueous sodium bicarbonate solution. The quenched reaction mixture was allowed to warm to rt and was extracted with ethyl acetate. The organic layers were combined, dried over sodium sulfate, filtered, and concentrated. The residue was suspended in ethanol with sonication. The resulting precipitate was collected via filtration and washed with a small amount of cold ethanol to obtain 2-((2-benzylidene-1-isopropylhydrazinyl)methylene)malononitrile as a yellow solid. The mother liquor was concentrated and the residue purified by silica gel column chromatography (1:1 hexanes/ethyl acetate eluant) to afford additional 2-((2-benzylidene-1-isopropylhydrazinyl)methylene)malononitrile. MS m/z 239.2 (M+1).

Intermediate. 2-((2-Benzylidene-1-ethylhydrazinyl)methylene)-malononitrile

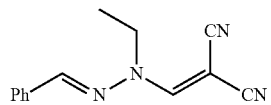 [SMILES: CCN(C=C(C#N)C#N)/N=C/c1ccccc1]

To a solution of 2-(ethoxymethylene)malononitrile (15.2 g, 0.124 mole) in 100 ml toluene was added Intermediate 1-benzylidene-2-ethylhydrazine (18.4 g, 0.124 mole). The mixture was allowed to stand at room temperature, and a precipitate formed. The reaction mixture was stirred for an additional 16 h. The precipitate was collected on a filter and washed with a small amount of cold ethanol to obtain 2-((2-benzylidene-1-ethylhydrazinyl)methylene)malononitrile as a solid.

Similarly prepared was 2-((2-Benzylidene-1-methylhydrazinyl)-methylene)malononitrile.

Intermediate. 3-Amino-1-isopropyl-1H-pyrazole-4-carbonitrile

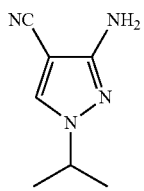

A mixture of Intermediate 2-((2-benzylidene-1-isopropylhydrazinyl)-methylene)malononitrile (9.42 g, 40 mmol), concentrated hydrochloric acid (5 ml), and ethanol (50 ml) was heated at reflux for 20 min. The reaction mixture was concentrated and ether (50 ml) was added. The mixture was sonicated, then the upper ether layer was discarded. To the residue was added 20 ml of 5N aqueous sodium hydroxide solution and the mixture was extracted with dichloromethane (3×). The organic layers were combined, dried over sodium sulfate, filtered, and concentrated. The residue was purified by silica gel column chromatography (1:1 hexanes/ethyl acetate eluant) to afford 3-amino-1-isopropyl-1H-pyrazole-4-carbonitrile as a brown solid. $^1$H NMR (400 MHz, DMSO-$d_6$) δ 8.09 (s, 1H), 5.51 (s, 2H), 4.22 (m, 1H), 1.31 (d, J=7 Hz, 6H); MS m/z 151.2 (M+1).

Similarly prepared were: 3-amino-1-ethyl-1H-pyrazole-4-carbonitrile; and 3-amino-1-methyl-1H-pyrazole-4-carbonitrile.

Intermediate.
1-(3-Amino-1-isopropyl-1H-pyrazol-4-yl)ethanone

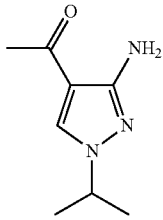

To a solution of Intermediate 3-amino-1-isopropyl-1H-pyrazole-4-carbonitrile (5.29 g, 36.5 mmol) in 200 ml anhydrous THF at 0° C. was added methylmagnesium bromide solution (3 M in ether, 56.5 ml, 0.17 mol). The reaction mixture was heated at reflux for 4 h. The mixture was cooled to 0° C. and was then quenched with 10% aqueous hydrochloric acid to neutral pH. The reaction was extracted with a large amount of 9:1 dichloromethane/isopropanol. The organic layers were combined and dried over sodium sulfate, filtered, and concentrated. The crude product was purified by silica gel column chromatography (1:1 ethyl acetate/hexanes to 9:1 ethyl acetate/methanol eluant) to afford the title compound as a light brown solid. $^1$H NMR (400 MHz, DMSO-$d_6$) δ 8.18 (s, 1H), 5.62 (s, 2H), 4.23 (m, 1H), 2.20 (s, 3H), 1.37 (d, J=7 Hz, 6H); MS m/z 168.2 (M+1).

Similarly prepared were: 1-(3-Amino-1-ethyl-1H-pyrazol-4-yl)ethanone; and 1-(3-Amino-1-methyl-1H-pyrazol-4-yl)ethanone.

Intermediate.
1-(3-Iodo-1-isopropyl-1H-pyrazol-4-yl)ethanone

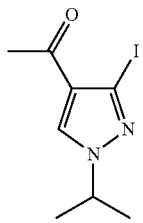

To a solution of Intermediate 1-(3-amino-1-isopropyl-1H-pyrazol-4-yl)ethanone (3.97 g, 24 mmol) and p-TsOH.H$_2$O (9.07 g, 48 mmole, 2 eq) in 150 ml of acetonitrile at 0° C. was added dropwise a solution of sodium nitrite (2.97 g, 43 mmole, 1.8 eq) and potassium iodide (8.0 g, 48 mmol, 2.0 eq) in 20 ml water. The mixture was stirred at this temperature for 10 minutes and then allowed to warm to rt and stirred for 3 h. The mixture was concentrated and then diluted with water and neutralized with aqueous sodium carbonate solution to pH 9 to 10. The mixture was extracted with ethyl acetate (3×). The combined organic layers were washed with sodium thiosulfate solution, dried over sodium sulfate, filtered, and concentrated. The residue was purified by silica gel column chromatography (1:1 hexanes/ethyl acetate eluant) to provide the title compound as a light brown solid. $^1$H NMR (400 MHz, DMSO-$d_6$) δ 8.51 (s, 1H), 4.53 (m, 1H), 2.37 (s, 3H), 1.41 (d, J=7 Hz, 6H); MS m/z 279.1 (M+1).

Similarly prepared were: 1-(3-Iodo-1-ethyl-1H-pyrazol-4-yl)ethanone; and 1-(3-Iodo-1-methyl-1H-pyrazol-4-yl)ethanone.

Intermediate. 3-(Dimethylamino)-1-(3-iodo-1-isopropyl-1H-pyrazol-4-yl)prop-2-en-1-one

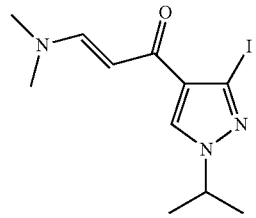 [SMILES: CC(C)n1cc(C(=O)/C=C/N(C)C)c(I)n1]

A mixture of Intermediate 1-(3-iodo-1-isopropyl-1H-pyrazol-4-yl)ethanone (5.0 g, 18.0 mmol) and N,N-dimethylformamide dimethyl acetal (50 mL) was heated at 155° C. for 20 h. The mixture was concentrated under vacuum to provide the crude title compound. MS m/z 334.0 (M+1).

Similarly prepared were: 3-(Dimethylamino)-1-(3-iodo-1-ethyl-1H-pyrazol-4-yl)prop-2-en-1-one; and 3-(Dimethylamino)-1-(3-iodo-1-methyl-1H-pyrazol-4-yl)prop-2-en-1-one.

Intermediate. 4-(3-Iodo-1-isopropyl-1H-pyrazol-4-yl)pyrimidin-2-amine

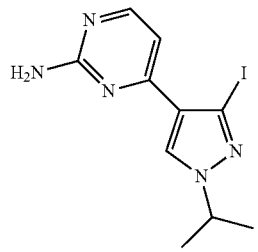 [SMILES: CC(C)n1cc(-c2ccnc(N)n2)c(I)n1]

A mixture of crude Intermediate 3-(dimethylamino)-1-(3-iodo-1-isopropyl-1H-pyrazol-4-yl)prop-2-en-1-one (4.0 g, 12.0 mmol), guanidine hydrochloride (2.63 g, 27.6 mmol), lithium hydroxide (635 mg, 27.6 mmol), and sec-butanol (50 ml) was heated with stirring in a sealed reaction vessel at 110° C. for 20 h. The cooled reaction mixture was concentrated, then water was added and the mixture was extracted with ethyl acetate. The combined extracts were dried over sodium sulfate, filtered, and concentrated. Ethyl acetate was added to the solid residue, and the mixture was sonicated. The solid product was collected on a filter, rinsed with ethyl acetate, and dried to give the title compound as a tan solid. MS m/z 330.0 (M+1).

Similarly prepared were: 4-(3-Iodo-1-ethyl-1H-pyrazol-4-yl)pyrimidin-2-amine; and 4-(3-Iodo-1-methyl-1H-pyrazol-4-yl)pyrimidin-2-amine.

Intermediate. 4-(3-Iodo-1-isopropyl-1H-pyrazol-4-yl)pyrimidin-2-ol

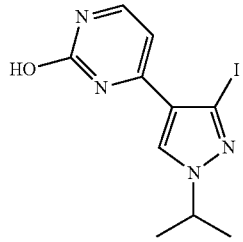 [SMILES: CC(C)n1cc(-c2ccnc(O)n2)c(I)n1]

Sodium nitrite (314 mg, 4.55 mmol) was added in portions to a stirred mixture of Intermediate 4-(3-iodo-1-isopropyl-1H-pyrazol-4-yl)pyrimidin-2-amine (500 mg, 1.52 mmol) and trifluoroacetic acid (15 ml) at 0° C. The mixture was allowed to warm to rt and was stirred for 1 h, then the solvent was removed under vacuum. The crude mixture was diluted with ethyl acetate and washed with saturated aqueous potassium carbonate solution and brine to provide the title compound as a solid. MS m/z 331.0 (M+1).

Similarly prepared were: 4-(3-Iodo-1-ethyl-1H-pyrazol-4-yl)pyrimidin-2-ol; and 4-(3-Iodo-1-methyl-1H-pyrazol-4-yl)pyrimidin-2-ol.

Intermediate. 2-Chloro-4-(3-iodo-1-isopropyl-1H-pyrazol-4-yl)pyrimidine

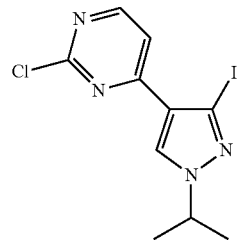 [SMILES: CC(C)n1cc(-c2ccnc(Cl)n2)c(I)n1]

A solution of Intermediate 4-(3-iodo-1-isopropyl-1H-pyrazol-4-yl)pyrimidin-2-ol (438 mg, 1.33 mmol) in phosphorous oxychloride (10 ml) was heated at 110° C. for 16 h. The mixture was concentrated under vacuum, then aqueous sodium bicarbonate solution was carefully added and the mixture was extracted with ethyl acetate. The combined organic extracts were dried over sodium sulfate, filtered, and concentrated to provide the title compound as a yellow solid. MS m/z 349.0 (M+1).

Similarly prepared were: 2-Chloro-4-(3-iodo-1-ethyl-1H-pyrazol-4-yl)pyrimidine; and 2-Chloro-4-(3-iodo-1-methyl-1H-pyrazol-4-yl)pyrimidine.

Intermediate. (S)-Methyl 1-hydroxypropan-2-ylcarbamate

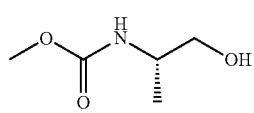

To a solution of (S)-alaminol (10 g, 130 mmol) and sodium bicarbonate (32.8 g, 390 mmol) in THF—H$_2$O (1:1, 650 mL) at 0° C. was added dropwise methyl chloroformate (11.4 mL, 143 mmol). The mixture was stirred and allowed to warm to rt over 4 h, and was then extracted with ethyl acetate. The organic layer was washed with 1N aqueous sodium hydroxide solution and brine, and was then dried over sodium sulfate, filtered and concentrated to give the crude title compound, which was used without further purification. MS m/z 134.1 (M+1).

Similarly prepared were: (R)-methyl 1-hydroxypropan-2-ylcarbamate, using (R)-alinol in place of (S)-alaminol; and (S)-1,1-Dimethylethyl 1-hydroxypropan-2-ylcarbamate using di-t-butyl-dicarbonate in place of methyl chloroformate.

Intermediate. (S)-Methyl 1-azidopropan-2-ylcarbamate

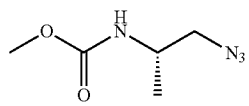

To a solution of Intermediate (S)-methyl 1-hydroxypropan-2-ylcarbamate (2.65 g, 20 mmol) and triethylamine (7.0 ml, 50 mmol) in anhydrous dichloromethane (100 mL) was added methanesulfonyl chloride (1.91 mL, 23.9 mmol). The mixture was stirred at rt for 3 h and was then extracted with ethyl acetate. The organic layer was washed with 1N sodium hydroxide solution and brine, and was then dried over sodium sulfate, filtered and concentrated. The crude mesylate product was then dissolved in dry DMF (70 mL) and sodium azide (5.2 g, 80 mmol) was added. The mixture was heated with stirring at 80° C. for 2 h. The cooled reaction mixture was concentrated and the residue was partitioned between ethyl acetate and brine. The organic layer was separated and washed with brine, dried over sodium sulfate, filtered and concentrated. The residue was purified by silica gel chromatography (8:1 hexane/ethyl acetate eluant) to afford (S)-methyl 1-azidopropan-2-ylcarbamate. MS m/z 159.1 (M+1).

Similarly prepared were: (R)-Methyl 1-azidopropan-2-ylcarbamate; and (S)-1,1-dimethylethyl 1-azidopropan-2-ylcarbamate.

Intermediate. (S)-Methyl 1-aminopropan-2-ylcarbamate

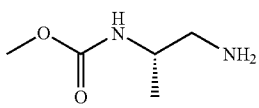

To a solution of Intermediate (S)-methyl 1-azidopropan-2-ylcarbamate (2.86 g, 18.2 mmol) in ethyl acetate (200 ml) was added 10% palladium on carbon (wet, 286 mg). The flask was degassed and refilled with hydrogen gas (balloon, 1 atmosphere), and the mixture was stirred at rt for 16 hours. The reaction mixture was filtered through a pad of celite and washed with ethyl acetate. The filtrate was concentrated to give crude (S)-methyl 1-aminopropan-2-ylcarbamate, which was used without further purification. $^1$H NMR 400 MHz (CDCl$_3$) δ 4.79 (s, 1H), 3.71-3.65 (m, 1H), 3.66 (s, 3H), 2.75 (dd, 1H), 2.65 (dd, 1H), 1.14 (d, 3H); MS m/z 133.1 (M+1).

Similarly prepared were: (R)-Methyl 1-aminopropan-2-ylcarbamate; and (S)-1,1-dimethylethyl 1-aminopropan-2-ylcarbamate.

Intermediate. (S)-Methyl 1-(4-(3-iodo-1-isopropyl-1H-pyrazol-4-yl)pyrimidin-2-ylamino)propan-2-ylcarbamate

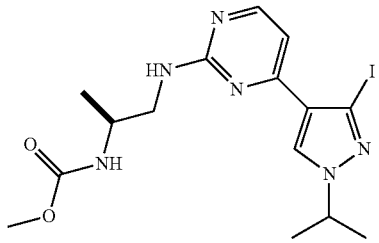 [SMILES: COC(=O)N[C@@H](C)CNc1nccc(-c2cn(C(C)C)nc2I)n1]

A solution of Intermediate 2-chloro-4-(3-iodo-1-isopropyl-1H-pyrazol-4-yl)pyrimidine (1.4 g, 4.01 mmol), (S)-methyl 1-aminopropan-2-ylcarbamate (0.8 g, 6 mmol) and triethylamine (2.8 ml, 20 mmol) in isopropanol (30 ml) and dioxane (20 mL) was heated in a sealed vessel at 125° C. for 48 hours. The cooled mixture was concentrated under vacuum, and aqueous sodium bicarbonate was added to the residue. The mixture was extracted with ethyl acetate, and the combined extracts were dried over sodium sulfate, filtered, and concentrated. The crude residue was purified by silica gel column chromatography (1:2 hexanes/ethyl acetate eluant) to provide the title compound as a white solid. MS m/z 445.0 (M+1).

Similarly prepared were: (R)-Methyl 1-(4-(3-iodo-1-isopropyl-1H-pyrazol-4-yl)pyrimidin-2-ylamino)propan-2-ylcarbamate; (S)-tert-butyl 1-(4-(3-iodo-1-isopropyl-1H-pyrazol-4-yl)pyrimidin-2-ylamino)propan-2-ylcarbamate; 3-(4-(3-iodo-1-isopropyl-1H-pyrazol-4-yl)pyrimidin-2-ylamino)propanenitrile; 4-(3-iodo-1-isopropyl-1H-pyrazol-4-yl)-N-methylpyrimidin-2-amine; and $N^1$-(4-(3-iodo-1-isopropyl-1H-pyrazol-4-yl)pyrimidin-2-yl)-$N^2$,$N^2$-dimethylethane-1,2-diamine.

Intermediate. N-(3-bromo-2,4-difluorophenyl)propane-1-sulfonamide

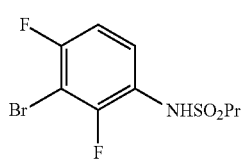

A solution of 3-bromo-2,4-difluoroaniline (4.16 g, 20 mmol, EP184384), n-propanesulfonyl chloride (4.6 ml, 40 mmol), pyridine (8 ml), DMAP (97 mg), and DCM (100 ml) was stirred at rt for 16 h. Aqueous sodium bicarbonate solution was added and the mixture was extracted with ethyl acetate. The organic layer was washed with aqueous sodium bicarbonate and brine. The crude product was purified by silica gel chromatography (8:1 to 3:1 hexanes/ethyl acetate eluant) to give the title compound. MS m/z 313.9 (M+1).

Intermediate. 3-Fluoro-4-iodopyridin-2-amine

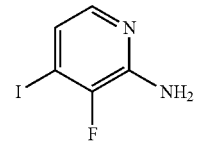

A solution of 2-amino-3-fluoropyridine (1.0 g, 8.9 mmol) in anhydrous THF (40 ml) was treated dropwise at −78° C. with n-butyllithium (1.6 M in hexanes, 13.9 ml, 22.3 mmol). Following the addition, the mixture was stirred at −78° C. for 1 h, then a solution of iodine (10.2 g, 40.1 mmol) in THF (20 ml) was added. The mixture was extracted with ethyl acetate, and the organic extracts were washed with sodium thiosulfate, sodium bicarbonate and brine. The organic phase was dried over sodium sulfate and concentrated. The crude product was purified by silica gel chromatography (8:1 to 2:1 hexanes/ethyl acetate eluant) to provide the title compound. MS m/z 238.9 (M+1).

Similarly prepared was: 3-chloro-4-iodopyridin-2-amine.

Intermediate. 3-Bromo-2,5,6-trifluoroaniline

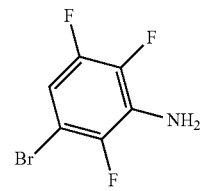 [SMILES: Nc1c(F)c(F)cc(Br)c1F]

To a microwave tube was added 1-bromo-2,3,4,5-tetrafluorobenzene (1.0 g) and 28% aqueous ammonium hydroxide (5 mL). The mixture was heated under microwave irradiation at 150° C. for 2 hrs, then the mixture was poured into water and extracted with hexane. The organic layer was separated, dried with $MgSO_4$, then concentrated. The residue was purified by silica gel flash chromatography (9:1 hexanes/ethyl acetate eluant) afford the title compound as a colorless liquid. $^1$H NMR (400 MHz, $CDCl_3$) δ 6.75 (m, 1H), 3.95 (br s, 2H) ppm; MS m/z: 226, 228 (M+H)$^+$.

Intermediate. 2,4-Dibromo-3,6-dichloroaniline

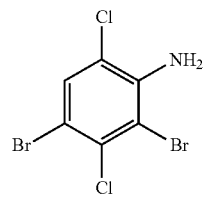 [SMILES: Nc1c(Cl)cc(Br)c(Cl)c1Br]

A mixture of 2,5-dichloroaniline (0.2 g), N-bromosuccinimide (0.48 g) and THF (20 mL) was stirred at rt for 2 hrs. The solvent was removed, and the residue was purified by silica gel flash chromatography (8:2 hexanes/ethyl acetate eluant) to afford the title compound. MS m/z: 318 (M+H)⁺.

Intermediate. 1,3-Dibromo-2,5-dichlorobenzene

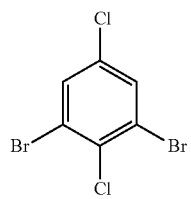

A stirred mixture of 2,4-dibromo-3,6-dichloroaniline (5.0 g), tert-Butyl nitrite (3.3 g) and EtOH (50 mL) was heated in a sealed tube at 50° C. for 2 hrs. The mixture was concentrated and the residue was purified by silica gel flash chromatography (hexanes eluant) to afford the title compound. MS m/z: 303 (M+H)⁺.

Intermediate. 3-Bromo-2-chloro-5-fluoroaniline

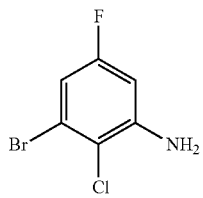

Step 1. 3-bromo-2-chloro-N-(diphenylmethylene)-5-fluoroaniline. A mixture of 2,6-dibromo-4-fluoro-1-chlorobenzene (865 mg, 3 mmol), benzophenone imine (0.61 ml, 3.6 mmol), Pd$_2$(dba)$_3$ (137 mg, 0.15 mmol), sodium t-butoxide (432 mg, 4.5 mmol), (S)-BINAP (280 mg, 0.45 mmol), and toluene (30 ml) was heated at 80° C. for 16 h. The mixture was extracted with ethyl acetate and the combined organic phase washed with brine. The organic phase was dried over sodium sulfate and concentrated. The crude product was purified by silica gel flash chromatography (40:1 to 20:1 hexanes/ethyl acetate eluant) to provide the title compound as a powder. MS m/z 388.9 (M+1).

Step 2. 3-Bromo-2-chloro-5-fluoroaniline. A solution of 3-bromo-2-chloro-N-(diphenylmethylene)-5-fluoroaniline (1.16 g) in THF (20 ml) was treated with 2N hydrochloric acid (1.5 ml, 1 eq) and the mixture was stirred at rt for 2 h. The mixture was extracted with ethyl acetate and the combined organic phase washed with brine. The organic phase was dried over sodium sulfate and concentrated. The crude residue was chromatographed on silica gel (40:1 to 15:1 hexanes/ethyl acetate eluant) to provide the title compound, contaminated by benzophenone. MS m/z 223.9 (M+1).

Similarly prepared were: 3-bromo-2,5-dichloroaniline; 3-bromo-2-chloro-5-methylaniline; and 3-bromo-2,5-difluoroaniline.

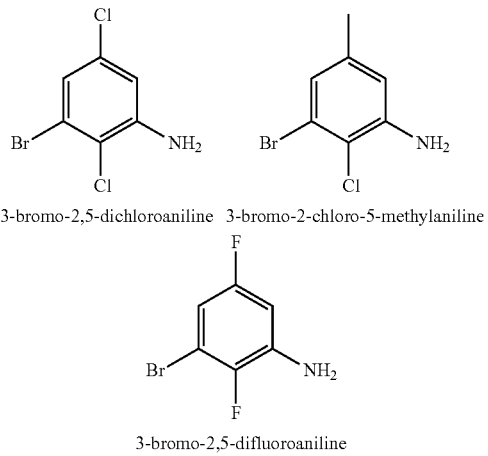

3-bromo-2,5-dichloroaniline    3-bromo-2-chloro-5-methylaniline 3-bromo-2,5-difluoroaniline Intermediate. 3-Bromo-5-chloro-2-fluorobenzoic acid

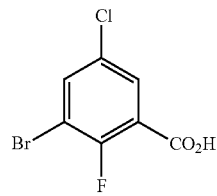 [SMILES: O=C(O)c1cc(Cl)cc(Br)c1F]

A solution of 2-bromo-4-chloro-1-fluorobenzene (4.31 g, 20 mmol) was added dropwise to a −78° C. solution of LDA in THF (prepared from diisopropylamine (3.38 ml, 24 mmol) and n-BuLi (1.6 M, 13.1 ml, 21 mmol)). The mixture was stirred at −78° C. for 1 h, and then was transferred slowly (~30-60 min) via cannula to a stirred −78° C. mixture of dry ice and THF (40 ml). The mixture was stirred at −78° C. for 1 h, and then was allowed to warm to rt (gas evolution). The mixture was concentrated, and was then treated with 50 ml of 1 N sodium hydroxide solution. The mixture was extracted with ethyl acetate (discarded). The aqueous layer was acidified with 1N hydrochloric acid, and then was extracted with chloroform (3×400 ml). The chloroform extract was dried over sodium sulfate, filtered, and concentrated to provide the crude title compound. The product was contaminated with a small amount of the isomeric product 2-bromo-6-chloro-3-fluorobenzoic acid. ¹H NMR for title compound 3-Bromo-5-chloro-2-fluorobenzoic acid: (400 MHz, CDCl$_3$) δ 7.93 (dd, 1H, J=2.8, 5.6 Hz), 7.79 (dd, 1H, J=2.8, 5.6 Hz) ppm.

Similarly prepared were: 3-bromo-2,6-difluorobenzoic acid; and 3-bromo-2-fluoro-5-methylbenzoic acid.

Intermediate. Tert-butyl 3-bromo-5-chloro-2-fluorophenylcarbamate

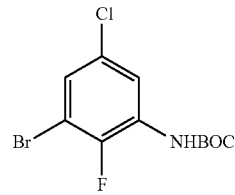

A solution of crude Intermediate 3-bromo-5-chloro-2-fluorobenzoic acid (2.03 g, 8 mmol), diphenylphosphoryl azide (2.07 mL, 9.6 mmol, 1.2 eq), and DIPEA (1.67 mL, 9.6 mmol, 1.2 eq) in 1:1 t-butanol/toluene (25 ml) was heated at 110° C. for 36 h. The mixture was concentrated, then partitioned between ethyl acetate and water. The organic layer was washed with brine, and was then dried over sodium sulfate, filtered, and concentrated. The crude product was purified by silica gel chromatography (30:1 to 10:1 hexanes/ethyl acetate eluant) to provide the title compound. MS m/z: 267.8 (M+H)$^+$. (M-$^t$Bu).

Similarly prepared were: tert-butyl 3-bromo-2,6-difluorophenylcarbamate; and tert-butyl 3-bromo-2-fluoro-5-methylphenylcarbamate.

Intermediate. 3-Bromo-5-chloro-2-fluoroaniline

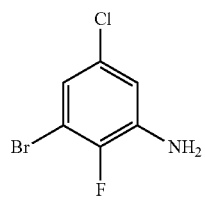

A solution of tert-butyl 3-bromo-5-chloro-2-fluorophenylcarbamate (900 mg, 2.78 mmol) in DCM/TFA (1:1, 20 mL) was stirred at rt for 1 h. The reaction mixture was concentrated, then the residue was taken up in ethyl acetate and washed with aqueous sodium bicarbonate and brine. The organic layer was dried over sodium sulfate, filtered, and concentrated to provide the crude title compound (736 mg). MS m/z 223.9 (M+1).

Intermediate. 5-bromo-3-methoxy-2-methylaniline

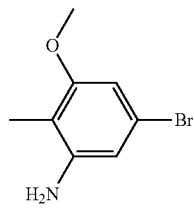

A heterogeneous reaction mixture of 4-bromo-2-methoxy-6-nitrotoluene (500 mg, 2.032 mmol), acetic acid (20 ml), and iron (1135 mg, 20.32 mmol) was stirred at rt for 24 hr. Ethyl acetate was added, then the mixture was filtered through celite and the filtrate concentrated. The residue was partitioned between ethyl acetate and saturated aqueous sodium bicarbonate solution. The aqueous layer was extracted with further ethyl acetate. The combined organic phases were washed with water and brine, then dried over sodium sulfate, filtered and concentrated to afford the title compound. MS m/z: 218.0 (M+H)$^+$.

Intermediate. Tert-butyl 5-chloro-2-fluoro-3-(4,4,5,5-tetramethyl-1,3,2-dioxaborolan-2-yl)phenylcarbamate

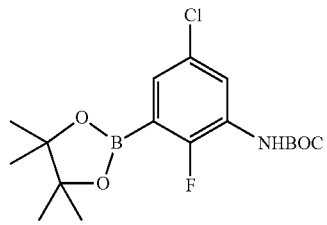

A mixture of Intermediate tert-butyl 3-bromo-5-chloro-2-fluorophenylcarbamate (1.45 g, 4.46 mmol), bis(pinacolato)diboron (1.7 g, 6.69 mmol), potassium acetate (1.53 g, 15.6 mmol), PdCl$_2$(dppf)-CH$_2$Cl$_2$ (163 mg, 0.22 mmol), and dioxane (100 ml) was heated in a sealed tube at 100° C. for 16 h. The crude reaction mixture was taken up in ethyl acetate and washed with aqueous sodium bicarbonate solution and brine. The organic layer was dried over sodium sulfate, filtered, and concentrated. The crude compound was diluted with hot hexane (600 mL), heated to 65° C. for 30 min. then cooled to room temperature. The brown mixture was filtered through Celite and the filter cake was washed with hexanes. The combined filtrates were concentrated to afford the crude title compound as a yellow oil. MS m/z 233 (M-pinacol-tBu).

Similarly prepared were: 5-chloro-2-fluoro-3-(4,4,5,5-tetramethyl-1,3,2-dioxaborolan-2-yl)aniline; tert-butyl 2,6-difluoro-3-(4,4,5,5-tetramethyl-1,3,2-dioxaborolan-2-yl)phenylcarbamate; N-(2,4-difluoro-3-(4,4,5,5-tetramethyl-1,3,2-dioxaborolan-2-yl)phenyl)propane-1-sulfonamide; 2-(2-fluoro-3-nitrophenyl)-4,4,5,5-tetramethyl-1,3,2-dioxaborolane; 2,5-difluoro-3-(4,4,5,5-tetramethyl-1,3,2-dioxaborolan-2-yl)aniline; 2-chloro-5-fluoro-3-(4,4,5,5-tetramethyl-1,3,2-dioxaborolan-2-yl)aniline; 2,5-dichloro-3-(4,4,5,5-tetramethyl-1,3,2-dioxaborolan-2-yl)aniline; 2-chloro-5-methyl-3-(4,4,5,5-tetramethyl-1,3,2-dioxaborolan-2-yl)aniline; tert-butyl 2-fluoro-5-methyl-3-(4,4,5,5-tetramethyl-1,3,2-dioxaborolan-2-yl)phenylcarbamate; 3-fluoro-4-(4,4,5,5-tetramethyl-1,3,2-dioxaborolan-2-yl)pyridin-2-amine; 2,3,6-trifluoro-5-(4,4,5,5-tetramethyl-1,3,2-dioxaborolan-2-yl)aniline; 3-chloro-4-(4,4,5,5-tetramethyl-1,3,2-dioxaborolan-2-yl)pyridin-2-amine; 3-chloro-5-(4,4,5,5-tetramethyl-1,3,2-dioxaborolan-2-yl)aniline; 3-methoxy-2-methyl-5-(4,4,5,5-tetramethyl-1,3,2-dioxaborolan-2-yl)aniline.

Intermediate. 2-fluoro-3-(4,4,5,5-tetramethyl-1,3,2-dioxaborolan-2-yl)aniline

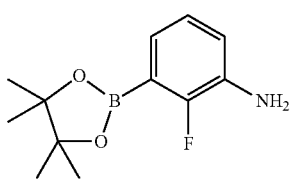 [SMILES: CC1(C)OB(c2cccc(N)c2F)OC1(C)C]

A mixture of Intermediate 2-(2-fluoro-3-nitrophenyl)-4,4,5,5-tetramethyl-1,3,2-dioxaborolane (500 mg), 10% palladium on carbon (50 mg) and ethyl acetate (20 ml) was stirred under 1 atmosphere of hydrogen for 16 h. The mixture was sparged with nitrogen and filtered. The filtrate was concentrated to provide the title compound, which was used without further purification. MS m/z 237.1 (M+1).

Example 1

Methyl N-[(2S)-1-[(4-{3-[2,6-difluoro-3-(propane-1-sulfonamido)phenyl]-1-(propan-2-yl)-1H-pyrazol-4-yl}pyrimidin-2-yl)amino]propan-2-yl]carbamate (Compound 7 in table 1)

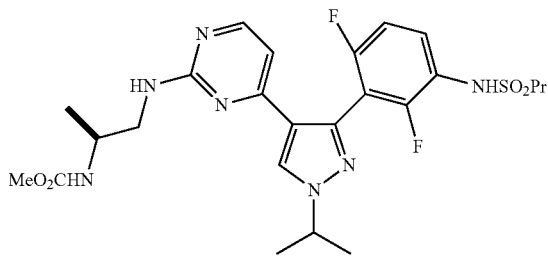

A mixture of crude Intermediate N-(2,4-difluoro-3-(4,4,5,5-tetramethyl-1,3,2-dioxaborolan-2-yl)phenyl)propane-1-sulfonamide (854 mg), Intermediate (S)-methyl 1-(4-(3-iodo-1-isopropyl-1H-pyrazol-4-yl)pyrimidin-2-ylamino)propan-2-ylcarbamate (350 mg, 90% pure), tetrakis(triphenylphosphine)palladium(0) (90 mg), 2 M aqueous sodium carbonate solution (6 ml), toluene (50 ml), and ethanol (6 ml) was heated at 80° C. for 16 h. The cooled mixture was extracted with ethyl acetate and the combined organic extracts were washed with brine. The organic phase was dried over sodium sulfate and concentrated. The crude product was purified by silica gel chromatography (70:1 to 40:1 DCM/methanol eluant) to provide the title compound.

Example 2

Methyl N-[(2S)-1-({4-[3-(2-chloro-5-fluoro-3-methanesulfonamidophenyl)-1-(propan-2-yl)-1H-pyrazol-4-yl]pyrimidin-2-yl}amino)propan-2-yl]carbamate (Compound 15 in table 1)

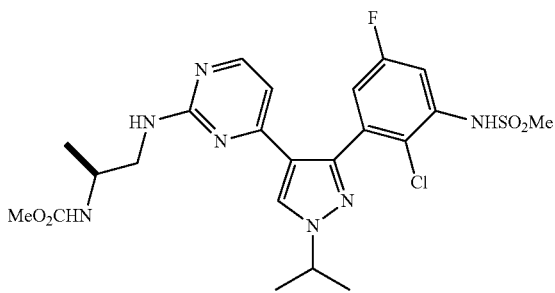

Step 1. (S)-Methyl 1-(4-(3-(3-amino-2-chloro-5-fluorophenyl)-1-isopropyl-1H-pyrazol-4-yl)pyrimidin-2-ylamino)propan-2-ylcarbamate. A mixture of crude Intermediate 2-chloro-5-fluoro-3-(4,4,5,5-tetramethyl-1,3,2-dioxaborolan-2-yl)aniline (214 mg), Intermediate (S)-methyl 1-(4-(3-iodo-1-isopropyl-1H-pyrazol-4-yl)pyrimidin-2-ylamino)propan-2-ylcarbamate (68 mg, 0.14 mmol), tetrakis(triphenylphosphine)-palladium(0) (16 mg), 2 M aqueous sodium carbonate solution (3 ml), toluene (18 ml), and ethanol (3 ml) was heated at 85° C. for 16 h. The mixture was extracted with ethyl acetate and the combined organic extracts were washed with brine. The organic phase was dried over sodium sulfate and concentrated. The crude product was purified by silica gel chromatography (60:1 to 40:1 DCM/methanol eluant) to provide the title compound (46 mg) contaminated with (S)-methyl 1-(4-(1-isopropyl-1H-pyrazol-4-yl)pyrimidin-2-ylamino)propan-2-ylcarbamate. MS m/z 462.1 (M+1).

Step 2. S)-Methyl 1-(4-(3-(2-chloro-5-fluoro-3-(methanesulfonamido)phenyl)-1-isopropyl-1H-pyrazol-4-yl)pyrimidin-2-ylamino)propan-2-ylcarbamate. A mixture of the aniline product of step 1 (46 mg), pyridine (2 ml), triethylamine (1 mL), DCM (4 ml), and methanesulfonyl chloride (23 ul, 0.3 mmol) was stirred at rt for 16 h. The crude reaction mixture was concentrated, then the residue was taken up in a mixture of toluene (9 ml), ethanol (1 ml), sodium carbonate (2 g), and water (10 ml). The stirred mixture was heated at 85° C. for 16 h. Workup as for Step 1 provided the crude product, which was purified by silica gel chromatography (60:1 to 40:1 DCM/methanol eluant) to provide the title compound.

Example 3

Methyl N-[(2S)-1-[(4-{3-[5-chloro-2-fluoro-3-(propane-1-sulfonamido)phenyl]-1-(propan-2-yl)-1H-pyrazol-4-yl}pyrimidin-2-yl)amino]propan-2-yl]carbamate (Compound 1 in table 1)

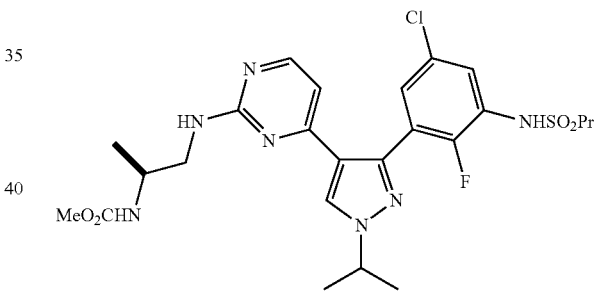

Step 1. (S)-Methyl 1-(4-(3-(5-chloro-2-fluoro-3-(tert-butoxycarbonylamino)phenyl)-1-isopropyl-1H-pyrazol-4-yl)pyrimidin-2-ylamino)propan-2-ylcarbamate. A mixture of crude Intermediate tert-butyl 5-chloro-2-fluoro-3-(4,4,5,5-tetramethyl-1,3,2-dioxaborolan-2-yl)phenylcarbamate (2.0 g), Intermediate (S)-methyl 1-(4-(3-iodo-1-isopropyl-1H-pyrazol-4-yl)pyrimidin-2-ylamino)propan-2-ylcarbamate (600 mg, 1.34 mmol), tetrakis(triphenylphosphine)palladium (0) (150 mg, 0.13 mmol), 2 M aqueous sodium carbonate solution (6.7 ml, 13.5 mmol), toluene (80 mL), and ethanol (6 mL) was heated at 80° C. for 16 h. The mixture was extracted with ethyl acetate and the combined organic extracts were washed with brine. The organic phase was dried over sodium sulfate and concentrated. The crude product was purified by silica gel chromatography (80:1 to 60:1 DCM/methanol eluant) to provide the title compound contaminated with triphenylphosphine oxide. MS m/z 562.1 (M+1).

Step 2. (S)-Methyl 1-(4-(3-(3-amino-5-chloro-2-fluorophenyl)-1-isopropyl-1H-pyrazol-4-yl)pyrimidin-2-ylamino)propan-2-ylcarbamate. A solution of partially-purified (S)-methyl 1-(4-(3-(5-chloro-2-fluoro-3-(tert-butoxycarbonylamino)phenyl)-1-isopropyl-1H-pyrazol-4- yl)pyrimidin-2-ylamino)propan-2-ylcarbamate (1.15 g) in DCM (50 mL) and TFA (20 mL) was stirred at rt for 1 h. The solvents were removed, then aqueous sodium bicarbonate solution was added. The mixture was extracted with ethyl acetate, and then the combined organic extracts were washed with sodium bicarbonate and brine. The organic phase was dried over sodium sulfate and concentrated. The product was obtained by silica gel chromatography (60:1 to 40:1 DCM/methanol eluant); MS m/z 462.1 (M+1).

Step 3. Methyl N-[(2S)-1-[(4-{3-[5-chloro-2-fluoro-3-(propane-1-sulfonamido)phenyl]-1-(propan-2-yl)-1H-pyrazol-4-yl}pyrimidin-2-yl)amino]propan-2-yl]carbamate. A mixture of (S)-methyl 1-(4-(3-(3-amino-5-chloro-2-fluorophenyl)-1-isopropyl-1H-pyrazol-4-yl)pyrimidin-2-ylamino)propan-2-ylcarbamate (41 mg, 0.09 mmol), triethylamine (1 ml), and DCM (4 ml) was treated with propanesulfonyl chloride (40 mg, 0.27 mmol). The mixture was stirred at rt for 16 h. The crude mixture was concentrated, and the residue was taken up in a mixture of toluene (9 ml), ethanol (1 ml), sodium carbonate (2 g), and water (10 ml). The stirred mixture was heated at 85° C. for 16 h. Workup as for Step 1 provided the crude product, which was purified by silica gel chromatography (60:1 to 40:1 DCM/methanol eluant) to provide the title compound.

Example 4

Methyl N-[(2S)-1-({4-[3-(5-chloro-2-fluoro-3-methanesulfonamidophenyl)-1-(oxan-2-yl)-1H-pyrazol-4-yl]pyrimidin-2-yl}amino)propan-2-yl]carbamate (Compound 33 in table 1) and Methyl N-[(2S)-1-({4-[3-(5-chloro-2-fluoro-3-methanesulfonamidophenyl)-1H-pyrazol-4-yl]pyrimidin-2-yl}amino)propan-2-yl]carbamate (Compound 31 in table 1)

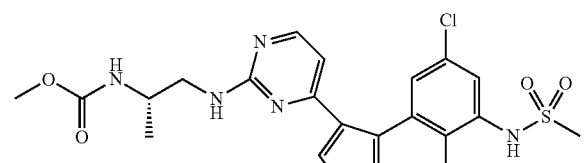

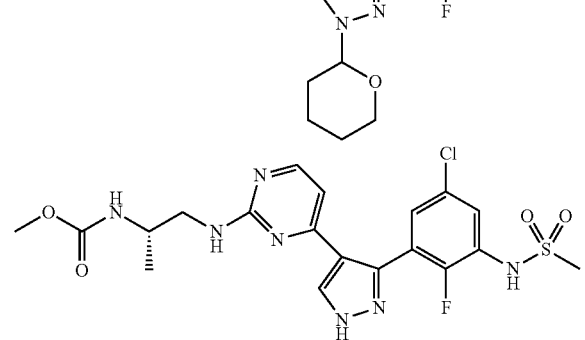

Step 1. 5-Chloro-2-fluoro-3-(4-(2-(methylthio)pyrimidin-4-yl)-1-(tetrahydro-2H-pyran-2-yl)-1H-pyrazol-3-yl)aniline. Prepared according to the procedure of Example 3, step 1, starting from intermediate 4-(3-iodo-1-(tetrahydro-2H-pyran-2-yl)-1H-pyrazol-4-yl)-2-(methylthio)pyrimidine and intermediate 5-chloro-2-fluoro-3-(4,4,5,5-tetramethyl-1,3,2-dioxaborolan-2-yl)aniline. MS m/z 420.0 (M+1).

Step 2. N-(5-Chloro-2-fluoro-3-(4-(2-(methylthio)pyrimidin-4-yl)-1-(tetrahydro-2H-pyran-2-yl)-1H-pyrazol-3-yl)phenyl)methanesulfonamide) and N-(5-chloro-2-fluoro-3-(4-(2-(methylthio)pyrimidin-4-yl)-1-(tetrahydro-2H-pyran-2-yl)-1H-pyrazol-3-yl)phenyl)-N-(methylsulfonyl)methanesulfonamide. To a solution of 5-chloro-2-fluoro-3-(4-(2-(methylthio)pyrimidin-4-yl)-1-(tetrahydro-2H-pyran-2-yl)-1H-pyrazol-3-yl)aniline (233 mg, 0.55 mmol) and triethylamine (2 mL) in dichloromethane (10 mL) was added methanesulfonyl chloride (0.13 mL, 1.66 mmol). The mixture was stirred at room temperature for 16 h, providing a mixture of the title compounds (LCMS analysis). Ethyl acetate was added and the mixture was washed with water and brine, then the organic layer was dried over sodium sulfate, filtered, and concentrated to provide the crude title mixture, which was used without further purification. MS m/z monosulfonamide 498.0 (M+1); bis-sulfonamide 576.0 (M+1)

Step 3. Methyl N-[(2S)-1-({4-[3-(5-chloro-2-fluoro-3-methanesulfonamidophenyl)-1-(oxan-2-yl)-1H-pyrazol-4-yl]pyrimidin-2-yl}amino)propan-2-yl]carbamate. The crude product mixture from Step 2 was dissolved in THF—H₂O (1:1, 30 mL) and treated at rt with Oxone® (1.68 g, 2.75 mmol). The mixture was stirred at rt for 16 h, then ethyl acetate was added. The organic layer was washed with aqueous sodium bicarbonate solution, water, and brine, then was dried over sodium sulfate, filtered, and concentrated. The crude residue was dissolved in NMP (5 mL) and treated with intermediate (S)-methyl 1-aminopropan-2-ylcarbamate (146 mg, 1.1 mmol) and sodium carbonate (233 mg, 2.2 mmol). The mixture was heated with stirring at 110° C. for 16 h. The cooled reaction mixture was diluted with ethyl acetate, and was then washed with water and brine. The organic layer was dried over sodium sulfate, filtered, and concentrated. The residue was chromatographed on silica gel (2% methanol in dichloromethane eluant) to provide the title compound.

Step 4. Methyl N-[(2S)-1-({4-[3-(5-chloro-2-fluoro-3-methanesulfonamidophenyl)-1H-pyrazol-4-yl]pyrimidin-2-yl}amino)propan-2-yl]carbamate. To a solution of methyl (2S)-1-(4-(3-(5-chloro-2-fluoro-3-(methylsulfonamido)phenyl)-1-(tetrahydro-2H-pyran-2-yl)-1H-pyrazol-4-yl)pyrimidin-2-ylamino)propan-2-ylcarbamate (94 mg, 0.16 mmol) in MeOH (15 mL) was added concentrated hydrochloric acid (0.5 mL). The mixture was stirred at rt for 16 h. Aqueous sodium bicarbonate was added to adjust the pH to 9 and the mixture was extracted with ethyl acetate. The organic layer was washed with aqueous sodium bicarbonate and brine. The crude product was purified by silica gel chromatography (30:1 to 15:1 dichloromethane/methanol eluant) to provide the title compound.

Example 5

Methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (Compound 9 in table 1)

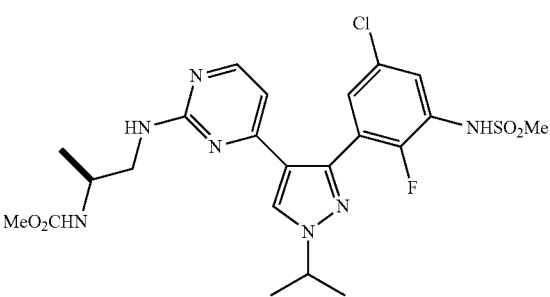

Methanesulfonyl chloride (0.277 mL, 3.57 mmol) was added to a solution of (S)-methyl 1-(4-(3-(3-amino-5-chloro-2-fluorophenyl)-1-isopropyl-1H-pyrazol-4-yl)pyrimidin-2-ylamino)propan-2-ylcarbamate (550 mg, 1.2 mmol) in DCM (30 mL) and pyridine (10 mL), and the mixture was stirred at rt for 16 h. Aqueous sodium bicarbonate solution was added, and the mixture was extracted with ethyl acetate and washed with brine. The organic phase was dried over sodium sulfate and concentrated. The crude product was purified by silica gel chromatography (60:1 to 40:1 DCM/methanol) to provide the title compound. An alternative synthesis is described in example 6, infra.

Also isolated from the reaction mixture were: Methyl N-[(2S)-2-({4-[3-(5-chloro-2-fluoro-3-methanesulfonamidophenyl)-1-(propan-2-yl)-1H-pyrazol-4-yl]pyrimidin-2-yl}amino)propyl]carbamate (Compound 32 in table 1); N-{3-[4-(2-aminopyrimidin-4-yl)-1-(propan-2-yl)-1H-pyrazol-3-yl]-5-chloro-2-fluorophenyl}methanesulfonamide (Compound 30 in table 1).

Example 6

Methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate (Compound 9 in table 1)

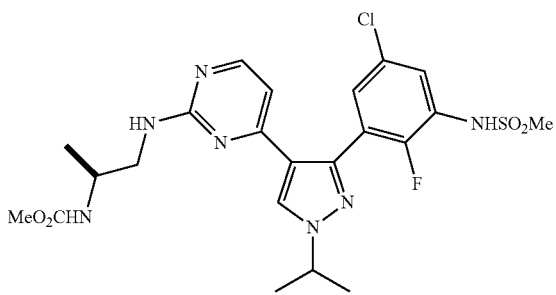

Step 1. 1-Benzylidene-2-isopropylhydrazine. Into a reactor equipped with a mechanical stirrer, a thermometer, and an addition funnel under nitrogen purge were charged isopropylhydrazine hydrogenchloride salt (712 g, 6.43 mol), sodium acetate (528 g, 6.43 mol), and 50% ethanol (4500 mL). The mixture was stirred at 20° C. for 5 min. Benzaldehyde (683 g, 6.43 mol) was added while maintaining the batch temperature below 23° C. The mixture was stirred at 20° C. over 20 h. Toluene (6500 mL) was added and stirring was maintained for 5 min. The organic layer was separated. Saturated aqueous sodium bicarbonate solution (4800 mL) was slowly added to the vigorously stirred organic layer (Note: the pH of the aqueous layer was ~8.0). The organic layer was separated and washed with saturated aqueous sodium bicarbonate solution (3000 mL). Then the organic layer was separated and concentrated under vacuum (50→20 torr) at 40° C. to give the title compound as a yellow oil (used without further purification).

Step 2. 2-((2-Benzylidene-1-isopropylhydrazinyl)methylene)-malononitrile. To a flask equipped with a mechanical stirrer, a thermometer, and an addition funnel under nitrogen purge were charged (ethoxyethylidine)malononitrile (755 g, 6.18 mol), DMAP (150 g, 1.23 mol), and ethanol (6400 mL). The mixture was stirred to give a dark orange solution and an endotherm from 20° C. to 12° C. was observed. 1-Benzylidene-2-isopropylhydrazine (1101 g, crude) was added slowly over 15 min to give an exotherm to 32° C. and an orange suspension. The orange suspension was heated to 50° C. and held at 50° C. for 30 min to give a dark brown suspension. Ethanol (3200 mL) was added to the mixture and the mixture was cooled to 20° C. and held at 20° C. for 1 h. The slurry was filtered and the solid cake was rinsed with ethanol (3000 mL). The solid was collected and dried under vacuum at 40° C./5 torr for 3 h to furnish the title compound as a yellow solid. HPLC purity >99%.

Step 3. 3-Amino-1-isopropyl-1H-pyrazole-4-carbonitrile. To a flask equipped with a mechanical stirrer, a thermometer, a condenser, and an addition funnel under nitrogen purge were charged 2-((2-benzylidene-1-isopropylhydrazinyl)methylene)-malononitrile (632.6 g, 2.65 mol), MeOH (2.5 L), and conc. (12 N) HCl (329.0 mL, 3.94 mol). The mixture was heated to 63° C. and held at 63° C. for 30 min to give an orange solution. The mixture was cooled to 15° C. Heptane (4 L) and MTBE (1 L) were added and the mixture stirred for 5 min. Then water (7.5 L) was added in a stream over 30 min at 15° C. to 25° C. The mixture was stirred 10 min at 25° C. after the water addition was complete. The heptane/MTBE layer was separated. The aqueous layer was washed with a (4:1 v/v) heptane/MTBE mixture (2×5 L) by stirring each wash for 10 min at 25° C. The layers were separated. Solid sodium chloride (1 Kg) was added to the aqueous layer. Saturated aqueous potassium carbonate solution was then added to the aqueous layer slowly to control the $CO_2$ evolution and to adjust the pH to ~9.0. The aqueous layer was then extracted twice with $CH_2Cl_2$ (1×2.2 L, 1×800 mL). The combined $CH_2Cl_2$ layers were dried over $MgSO_4$, filtered and the filtrate was concentrated under vacuum (200 torr) at a bath temperature of 30° C. until the residual weight was ~1 Kg. Heptane (6.0 L) was slowly added (over ~20 min) to the $CH_2Cl_2$ solution with stirring and a slurry was formed. The mixture was concentrated under vacuum (60 torr) at an internal temperature of 25° C. until the residual volume was ~6.2 L. The slurry was cooled to 15° C. and held at this temperature for 10 min. The product was filtered and the solid was washed with heptane (1 L). The solid was dried under vacuum (5 torr) at 30° C. for 4 h to furnish the title compound as a yellow solid. HPLC purity >99%.

Step 4. 1-(3-Amino-1-isopropyl-1H-pyrazol-4-yl)-ethanone. To a flask fitted with a mechanical stirrer, thermometer, reflux condenser, heating/cooling capacity, addition funnel, and nitrogen inlet/outlet was charged 3-amino-1-isopropyl-1H-pyrazole-4-carbonitrile (274 g, 1.82 mole) and cyclopentyl methyl ether (2600 mL) at 20° C. under nitrogen. The suspension was cooled to –10° C. 1.5 M Methyllithium/lithium bromide complex in diethyl ether solution (6.0 L, 9.00 mol) was added dropwise over 2.5 h at –10° C. to 0° C. When the methyllithium addition was complete the reaction suspension was quickly warmed to 5° C. to 10° C. and held in this temperature range for 1 h. The mixture was cooled to 0° C. and 2N HCl (6.0 L) was added dropwise at 5-10° C. The (upper) organic layer was separated and extracted with 2N HCl (500 mL). The combined aqueous layers were stirred at rt over 16 h. The mixture was cooled to 15° C. and basified with 50% NaOH (260.0 g) to give a pH of ~11.0. The mixture was extracted with $CH_2Cl_2$ (1×2.0 L, 1×1 L). The combined $CH_2Cl_2$ layers were dried over $MgSO_4$, filtered and concentrated under vacuum to give a yellow solid (278 g). The solid was dissolved in EtOAc (750 mL) upon heating to 65° C. The solution was cooled to rt and a slurry was obtained. Heptane (1500 mL) was added slowly over 40 min at rt. The slurry was cooled to –10° C. and held at –10° C. for 30 min. The slurry was filtered and the filter cake was rinsed with heptane (300 mL). The solid was dried under vacuum (5 torr) at 40° C. for 3 h to give the title compound as a light brown solid. HPLC purity >99%. M.P. 136-139° C.

Step 5. 1-(3-Iodo-1-isopropyl-1H-pyrazol-4-yl)-ethanone. A flask equipped with a mechanical stirrer, a thermometer, and an addition funnel under nitrogen purge was charged with 1-(3-amino-1-isopropyl-1H-pyrazol-4-yl)-ethanone (250.0 g, 1.49 mol) and acetonitrile (3725 mL). The mixture was cooled to −20° C. BF$_3$.THF (313.1 g, 2.23 mol) was added dropwise while keeping the internal temp.<−10° C. Isoamyl nitrite (227.5 g, 1.94 mol) was added dropwise while keeping internal temp.<−10° C. The mixture was allowed to warm to 10° C. and was stirred at 10° C. for 30 min. The mixture was added in a thin stream to a flask containing a mixture of I$_2$ (28.5 g, 0.112 mol), KI (371.9 g, 2.24 mol) and acetonitrile (1160 mL) at 10-15° C. with vigorous stirring. The addition caused the evolution of nitrogen gas and a slight exotherm. The mixture was stirred at rt for 30 min. HPLC showed no diazonium intermediate left. Then sodium bisulfite (157.1 g, 1.51 mol) in 8% sodium chloride solution (4360 mL) was added at 15-20° C. The mixture was basified with saturated potassium carbonate to pH~8.5. The top acetonitrile layer was separated and concentrated under vacuum to give an oily residue. The oil was dissolved in iPrOAc (2770 mL) and washed with saturated aqueous sodium carbonate solution (1100 mL). The iPrOAc layer was separated and concentrated to a residual volume of ~1.5 L. A suspension was obtained. To the suspension was added heptane (5.5 L) over 30 min at 20° C. The suspension was stirred for 10 min at 20° C. after the heptane addition was complete. The slurry was filtered and the solid was rinsed with heptane (1 L) and then dried at 20° C. under vacuum (5 torr) for 16 h to give the title compound. MP: 90-92° C.

Step 6. 3-(Dimethylamino)-1-(3-iodo-1-isopropyl-1H-pyrazol-4-yl)-prop-2-en-1-one. To a flask equipped with a mechanical stirrer, a thermometer, and an addition funnel under nitrogen purge were charged 1-(3-Iodo-1-isopropyl-1H-pyrazol-4-yl)-ethanone (640 g, 2.30 mol) and DMF (6.4 L). The resulting orange solution was heated to 120° C. Bredereck's reagent (598.6 g, 3.43 mol) was added in one portion. The addition caused the batch temperature to decrease to 114° C. and the solution turned darker orange in color. The mixture was stirred at 120° C. for 20 min. The mixture was cooled to rt and then concentrated at 5 mmHg at 60° C. to give an oily residue. The residue was dissolved in iPrOAc (2400 mL) by warming to 74° C. The mixture was cooled to 35° C. and stirred to obtain a slurry. Heptane (6000 mL) was added at 35° C. to rt over 1 h. The mixture was cooled to −15° C. and filtered and the solid was dried under vacuum at 40° C. for 3 h to give the title compound as a solid. HPLC purity >98%. MP: 106-109° C.

Step 7. 4-(3-Iodo-1-isopropyl-1H-pyrazol-4-yl)-pyrimidin-2-amine. To a flask equipped with a mechanical stirrer, a thermometer, a Dean-Stark trap, and a condenser under nitrogen purge were charged (E)-3-dimethylamino-1-(3-iodo-1-isopropyl-1H-pyrazol-4-yl)-prop-2-en-1-one (735 g, 2.2 mol), guanidine carbonate (596 g, 3.3 mol) and NMP (5200 mL). The mixture was heated to 130° C. and held at 130° C. for 5 h. (Note: any low-boiling fractions were collected by the Dean-Stark trap). The mixture was cooled to 80° C. and 15% aq. sodium chloride (7500 mL) was added at 80° C. to 35° C. over ~1 h. The product began to precipitate approximately half way thru the aqueous sodium chloride addition. The mixture was further cooled to rt and held for 30 min. The solid product was collected by filtration and dried under vacuum at 65° C. for 16 h to give the title compound as a solid. HPLC purity >99%. MP: 167-169° C.

Step 8. 4-(3-Iodo-1-isopropyl-1H-pyrazol-4-yl)-pyrimidin-2-ol. A flask equipped with a mechanical stirrer and thermometer under nitrogen purge was charged with TFA (748.8 mL). 4-(3-Iodo-1-isopropyl-1H-pyrazol-4-yl)-pyrimidin-2-amine (300 g, 0.91 mol) was added in portions as a solid while maintaining the internal temperature below 30° C. using a cold water bath. The mixture was stirred at rt for 10 min to obtain a solution. The mixture was cooled to 20° C. and sodium nitrite (79.7 g, 1.27 mol) was added in portions over 5 h at 22-28° C. with rapid stirring. (Note: some gas evolution was observed and there was a mild exotherm that was easily controlled using a cool water bath). DCM (12 L) was added and the mixture was warmed to 27° C. Water (4400 mL) was added (Note: gas evolution at beginning). Saturated potassium carbonate solution (~1500 mL) was added slowly to the mixture to basify to pH~9.0 (Note: A large amount of gas was evolved). To the mixture was added a solution of sodium bisulfite (32 g, 0.30 mol) in water (100 mL). The mixture was stirred at 27° C. for 15 min and the pH was readjusted to ~9.0. The DCM layer was separated and concentrated under vacuum (200-100 mmHg) at a bath temp of 40° C. until the residual weight was ~2300 g (~1750 mL). To the residue was added MTBE (1500 mL) at 20° C. The mixture was stirred 10 min at 20° C. and was then filtered. The solid was dried 16 h at 30° C. under vacuum (5 torr) to give the title compound as an off-white solid. HPLC purity >99%. MP: 216-218° C.

Step 9. 2-Chloro-4-(3-iodo-1-isopropyl-1H-pyrazol-4-yl)-pyrimidine. To a flask fitted with a stirrer, thermometer, condenser, addition funnel and nitrogen inlet/outlet was charged 4-(3-iodo-1-isopropyl-1H-pyrazol-4-yl)-pyrimidin-2-ol (311 g, 942 mmol). To the solid was added acetonitrile (2500 mL) at 20° C. The mixture was stirred to give a suspension. To the suspension was added DIPEA (246.2 mL, 1.41 mol), followed by DMF (218.8 mL, 2.83 mol). The resulting suspension was stirred 5 min at 20° C. To the suspension was added POCl$_3$ (217 g, 1.41 mol) at 20-40° C. to give an orange solution. The mixture was warmed to 80° C. and held at 80° C. for 3 h. The mixture was cooled to 10° C. and a solution of ammonium hydroxide (622 mL of 28%) in deionized water (5550 mL) was added slowly over 1.5 h, keeping the temperature below 20° C. After completion of the ammonium hydroxide addition, the resulting suspension was stirred for 40 min at 10-20° C. The solid product was collected by filtration and dried overnight at 40° C. under vacuum (5 torr) to give the title compound as a brown solid HPLC purity >99%.

Step 10. (S)-Benzyl 2-(methoxycarbonylamino)propylcarbamate. To a suspension of (S)-1,2-diaminopropane dihydrochloride (50 g, 340 mmol) in dichloromethane (500 mL) was added potassium carbonate (1190 mmol). The suspension was stirred and filtered to collect the filtrate. The filtrate was cooled to 0-5° C. and stirred while benzyl chloroformate (51 ml, 357 mmol) was added dropwise. Following completion of the addition, the reaction mixture was stirred for 3 h at 0-5° C., and was then allowed to warm to rt and was stirred at rt overnight. To this mixture was added dropwise triethylamine (71 ml, 510 mmol) and the mixture was cooled to 0-5° C. Methyl chloroformate (28 ml, 357 mmol) was added slowly at 0-5° C. and the mixture was allowed to warm to rt and was stirred overnight. The mixture was poured into water. The organic volatiles were removed under vacuum. The resulting aqueous slurry was filtered to collect the solids, and the filter cake was then washed with ethyl acetate to provide a white solid (65 g, 92-94% HPLC purity). Multiple recrystallizations from ethyl acetate provided the title compound as a white solid, HPLC purity 99.5%.

Step 11. (S)-Methyl 1-aminopropan-2-ylcarbamate Hydrochloric Acid Salt. A solution of (S)-Benzyl 2-(methoxycarbonylamino)propylcarbamate in methanol was hydrogenated over a 5% palladium/C catalyst at 50-60 psi. The reaction mixture was filtered and the filtrate was concentrated under vacuum to give a colorless oil. 60 g of the colorless oil was dissolved in 200 mL of anhydrous dichloromethane and the solution was cooled to 0-5° C. in an ice-water bath. A solution of HCl in methanol (ca. 75 mL) was added dropwise until the pH of the solution was <1. The resulting suspension was stirred at 0-5° C. for 30 min, then the solid was collected via filtration. The solid was washed with dichloromethane and then with hexanes to give the title compound as a white solid.

Step 12. 3-Bromo-5-chloro-2-fluorobenzaldehyde. A solution of 2,2,6,6-tetramethylpiperidine (327 g, 98%, 2.274 mol) and THF (1.9 L, HPLC grade) was cooled to −75° C. (dry ice-methanol bath) under an argon atmosphere. 1.6 M n-BuLi/hexane solution (1.47 L, 2.35 mol) was added slowly into the mixture at −72 to −67° C. over 1 h. The mixture was stirred at −72 to −67° C. for 30 min to give a pale yellow suspension. 2-Bromo-4-chloro-1-fluorobenzene (435 g, 97%, 2.02 mol) was added slowly into the mixture at −72 to −67° C. over 30 min, and then the mixture was stirred at −72 to −67° C. for an additional 30 min. Dimethylformamide (230 g, 99.5%, 3.14 mol) was added slowly into the mixture at −70 to −65° C. over 30 min and then the mixture was stirred at −70 to −65° C. for 30 min to afford a light brown solution. The cooling bath was removed and then saturated ammonium chloride solution (720 mL) was added into the batch at −60 to −30° C. over 15 min to obtain a hazy mixture. 6 N hydrochloric acid was quickly added into the mixture at −30 to 10° C. over 15 min to pH 1 and then ethyl acetate (2.0 L) was added at 10 to 20° C. The layers were separated and the aqueous layer was extracted with ethyl acetate (1×300 mL). The combined organic extracts were washed with water (1×800 mL) and brine (1×500 mL), dried over magnesium sulfate, and filtered. The filtrate was concentrated under vacuum (60-65° C.) to give the title compound as a tan viscous oil, which solidified upon standing after several hours. $^1$H NMR (CDCl$_3$): δ 7.76-8.30 (m, 2H), 10.0-10.8 (br s, 1H); MS m/z 238.0 (M+1).

Step 13. 3-Bromo-5-chloro-2-fluorobenzoic acid. A stirred mixture of 3-bromo-5-chloro-2-fluorobenzaldehyde (415 g), tert-butanol (1.2 L) and water (1.2 L) was warmed to 30° C. and then potassium permanganate (335 g, 2.12 mol) was added (5 portions) into the batch at 40-45° C. over 1 h. The dark purple contents were heated in a step-wise fashion at 45-50° C. for 30 min, 50-55° C. for 30 min and 55-60° C. for 30 min to afford a purple-brown suspension. The reaction mixture was allowed to cool to 20° C., then saturated sodium sulfite solution was added at 22-27° C., until a negative peroxide test was obtained. Warm water (2.5 L, ~50° C.) and saturated sodium carbonate solution (100 mL) were added sequentially into the mixture over 15 min. The dark suspension was filtered through a 1 cm celite bed, and the filter cake was washed with warm water (4×1 L, ~50 C). The combined filtrate was acidified with 6 N hydrochloric acid solution to pH 1 to obtain a yellow oily suspension. Ethyl acetate (3 L) was added into the mixture and the mixture was stirred for 10 min. The (upper) organic layer was washed with water (1.2 L), dried over magnesium sulfate, filtered, and concentrated under vacuum (60-65° C.) to give a thick yellow suspension. Hexane (700 mL) was added into the residue and the suspension was cooled to 5-10° C. The solid was collected by filtration, and the filter cake was dried under vacuum (65° C.) overnight to give the title compound as a yellow solid. mp 150-152° C.; HPLC purity (225 nm): 97.5%; $^1$H NMR (d$_6$-DMSO): δ 7.82 (s, 1H), 8.10 (s, 1H), 13.82 (br s, 1H); MS m/z 254 (M+H).

Step 14. Tert-butyl 3-bromo-5-chloro-2-fluorophenylcarbamate. A mixture of 3-bromo-5-chloro-2-fluorobenzoic acid (243 g, 97.5%, 0.935 mol), triethylamine (105 g, 99.5%, 1.02 mol), and tert-butanol (1.4 L) was heated to 74° C. A solution of diphenylphosphoryl azide (260 g, 97%, 0.916 mol) in toluene (960 mL) was added slowly into the mixture at 75-79° C. over 1 h (gentle refluxing). The mixture was heated slowly to 83° C. over 30 min and maintained at 83-84° C. (gentle refluxing) for 1 h. The contents were concentrated under vacuum (65-70° C.) to a viscous oil. Toluene (2 L) and water (1.5 L) were added sequentially into the batch and the mixture was then stirred at 35° C. for 15 min. The aqueous layer was discarded The organic layer was washed with saturated sodium bicarbonate solution (400 mL) and water (400 mL). The organic layer was concentrated under vacuum (60-65° C.) to ~350 mL residue (~94% purity). 10% ethyl acetate/hexane (~1.2 L, v/v) was added into the batch and the mixture was then heated at 50° C. for 15 min to give a light yellow homogenous solution. Ethyl acetate/hexane solution was transferred onto a premade silica gel (1.8 kg, 70-200 mesh)/hexane bed on a 4-L Pyrex Büchner funnel (with coarse fritted discs, 40-60 μm, 16 cm diameter, 18 cm height). t-Butyl carbamate product was eluted (by gravity) slowly with 3-5% ethyl acetate/hexane (total volume ~5 L, v/v) to collect the title compound as an off-white solid. mp 87-88° C.; HPLC purity (225 nm): 97-98%; $^1$H NMR (d$_6$-DMSO): δ 1.48 (s, 9H), 7.48-7.49 (m, 1H), 7.80-7.82 (m, 1H), 9.42 (s, 1H); MS m/z 325 (M+H).

Step 15. (S)-Methyl 1-(4-(3-iodo-1-isopropyl-1H-pyrazol-4-yl)pyrimidin-2-ylamino)propan-2-ylcarbamate. To a 4-neck flask equipped with a mechanical stirrer, a thermometer, and a condenser under nitrogen purge were charged 2-Chloro-4-(3-iodo-1-isopropyl-1H-pyrazol-4-yl)-pyrimidine (300.0 g), (S)-methyl 1-aminopropan-2-ylcarbamate hydrochloric acid salt (174.3 g), sodium carbonate (365.7 g) and DMSO (2400 mL). The mixture was heated with stirring for 18 h at an internal temperature of 90° C. The mixture was cooled to 40° C. Toluene (3870 mL) was added at 37-43° C. with stirring. Water (7200 mL) was added at 37-43° C. The Toluene layer was separated at 37-43° C. To the Toluene layer was added 15% aqueous sodium chloride 1 solution (3870 mL) and the pH of the aq. layer was adjusted to a pH~5.0 by the addition of 10% aqueous citric acid solution at 37-43° C. The pH adjustment required ~20 mL of 10% aqueous citric acid. The toluene layer was then washed with saturated aqueous sodium bicarbonate solution (2880 mL) at 37-43° C. The toluene layer containing the title compound was used as input in step 17.

Step 16. Tert-butyl 5-chloro-2-fluoro-3-(4,4,5,5-tetramethyl-1,3,2-dioxaborolan-2-yl)phenylcarbamate. To a flask equipped with a mechanical stirrer, thermometer, condenser, and heating mantle under nitrogen purge were charged tert-butyl 3-bromo-5-chloro-2-fluorophenylcarbamate (33.0 g), bis(pinacolato)diboron (447.0 g), potassium acetate (405.6 g) and toluene (2700 mL). The mixture was stirred at rt for 15 min and PdCl$_2$(dppf) (50.4 g) was added. The mixture was then heated to 108±2° C. (Note: The mixture turned dark at 50-60° C.) A solution of tert-butyl 3-bromo-5-chloro-2-fluorophenylcarbamate (414 g) in toluene (1770 mL) was added at 108±2° C. over 70 min. The mixture was held at 108±2° C. for 15 h. The mixture was cooled to rt under nitrogen flow and then was filtered through celite. The filtrate containing the title compound was used as input in step 17.

Step 17. (S)-Methyl 1-(4-(3-(5-chloro-2-fluoro-3-(tert-butoxycarbonylamino)phenyl)-1-isopropyl-1H-pyrazol-4-yl)pyrimidin-2-ylamino)propan-2-ylcarbamate. To a flask was charged (S)-methyl 1-(4-(3-iodo-1-isopropyl-1H-pyrazol-4-yl)pyrimidin-2-ylamino)propan-2-ylcarbamate (3870 ml toluene solution, ~382 g, 0.861 mol) and tert-butyl 5-chloro-2-fluoro-3-(4,4,5,5-tetramethyl-1,3,2-dioxaborolan-2-yl)phenylcarbamate (4470 ml toluene solution, ~467.0 g, 1.26 mol). To the resulting brown solution was added a solution of sodium carbonate (349.8 g, 3.30 mol) in water (1400 mL). To the mixture was added PdCl$_2$(dppf) (34.5 g, 0.047 mol). The mixture was warmed to 80° C. with stirring and was held at this temperature for 2 h. The mixture was cooled to 40° C. and filtered thru celite. The layers in the filtrate were separated. The toluene layer containing the title compound was used directly as input in step 18.

Step 18. (S)-Methyl 1-(4-(3-(3-amino-5-chloro-2-fluorophenyl)-1-isopropyl-1H-pyrazol-4-yl)pyrimidin-2-ylamino)propan-2-ylcarbamate. To a flask was charged (S)-methyl 1-(4-(3-(5-chloro-2-fluoro-3-(tert-butoxycarbonylamino)phenyl)-1-isopropyl-1H-pyrazol-4-yl)pyrimidin-2-ylamino)propan-2-ylcarbamate (~7.3 L toluene solution, ~483.3 g, 0.86 mol) at 20° C. under a nitrogen atmosphere. To the solution was added 12N HCl (574.3 mL, 6.95 mol) over ~20 min while maintaining the temperature below 25° C. The HCl addition caused an exotherm from 19° C. to 24° C. The mixture was stirred at 20-23° C. for 1 h. To the reaction mixture was added water (3100 mL). The mixture was stirred 10 min at 20° C. The aqueous layer was separated and washed with 2-methylTHF (3100 mL). To the aqueous layer was slowly added saturated aqueous potassium carbonate solution (~778 mL). The pH of the aqueous layer was ~8.5. The aqueous layer was extracted with 2-methylTHF (3825 mL). The 2-methylTHF layer was concentrated under vacuum (60 mmHg, 40° C.). The residue was diluted with 2-methylTHF (~3800 mL) to provide a solution of the title compound, which was used directly as input in step 19. HPLC purity: 95%.

Step 19. (S)-Methyl 1-(4-(3-(5-chloro-2-fluoro-3-(N-(methylsulfonyl)methylsulfonamido)phenyl)-1-isopropyl-1H-pyrazol-4-yl)pyrimidin-2-ylamino)propan-2-ylcarbamate. To a flask was charged (S)-methyl 1-(4-(3-(3-amino-5-chloro-2-fluorophenyl)-1-isopropyl-1H-pyrazol-4-yl)pyrimidin-2-ylamino)propan-2-ylcarbamate (~3.8 L methylTHF solution, ~396.5 g, 0.86 mol) at 20° C. To the solution was added triethylamine (435.0 g, 4.3 mol). The solution was cooled to 0 to −5° C. To the solution was added methanesulfonyl chloride (246.0 g, 2.15 mol) dropwise with stirring over 20 min at 0 to −5° C. The mixture was allowed to warm to 18-20° C. and was held at this temperature for 20 min. To the reaction mixture was added water (2115 mL) over 30 min at 18-20° C. The mixture was stirred 10 min at 20° C. after the addition was complete. Then the pH was adjusted to between 6.0 and 6.5 with 2N HCl (~1230 mL). The pH was then adjusted to 7-7.5 using saturated aqueous sodium bicarbonate solution. The mixture was stirred 10 min @ 20° C. The layers were separated. The 2-methylTHF layer containing the title compound was used directly in step 20.

Step 20. Methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate. To a flask was charged (S)-methyl 1-(4-(3-(5-chloro-2-fluoro-3-(N-(methylsulfonyl)methylsulfonamido)phenyl)-1-isopropyl-1H-pyrazol-4-yl)pyrimidin-2-ylamino)propan-2-ylcarbamate (~3.8 L methylTHF solution, ~531.5 g, 0.86 mol). To the solution was added 3N aqueous sodium hydroxide (1782.8 mL, 5.34 mol) at 15-20° C. with stirring. The mixture was vigorously stirred at 20-23° C. over 30 min and the stirring was stopped. The aqueous layer was discarded. 2N HCl (~410 mL) was added to the organic layer to adjust the pH to 6.0-6.5, then saturated aqueous sodium bicarbonate solution (~300 mL) was added to adjust the pH~8.5. The aqueous layer was discarded. The organic layer was washed with 15% aqueous sodium chloride solution (2000 mL). The organic layer was concentrated under vacuum (80 torr) at a bath temperature of 45° C. to give a brown solution (780 g). The solution was diluted with 2-methylTHF (3500 mL), and then a suspension of PICA HP 120N activated carbon (90 g, CDH858) in 2-methylTHF (1 L) was added. The resulting black suspension was warmed to 60° C. and held at 60° C. for 16 h. After the 16 h hold the Pd content was 309 ppm. The mixture was cooled to 20° C. and filtered through a pad of celite (prewetted with 2-methylTHF). The reaction flask was rinsed with 2-methylTHF (500 mL). This rinse was then poured thru the filter cake of PICA/celite. To the filtrate was added PL-TMT resin (90 g). The resulting suspension was heated with stirring to 60° C. and held at this temperature for 4 h. After 4 h at 60° C. the Pd content was 2.3 ppm. The mixture was cooled to 20° C. and stirred overnight at 20° C. The mixture was filtered through a pad of celite (prewetted with 2-methylTHF). The filtrate was concentrated under vacuum (100-80 torr) at 40-45° C. to give an orange oil. This residual oil was dissolved in 3 L of 200 proof ethanol by warming to 78° C. The resulting clear orange solution was then cooled to 20° C. over 3 h, and a precipitate formed. The mixture was then cooled to 0° C. and held 1 h at 0° C. The mixture was filtered and the filter cake was washed with ethanol (300 mL). The solid was dried 14 h at 40° C. to give the title compound; MP: 186-189° C.

The compounds in the following table 1 were prepared similarly to the above examples, using the appropriate starting materials:
TABLE 1
| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 1 | 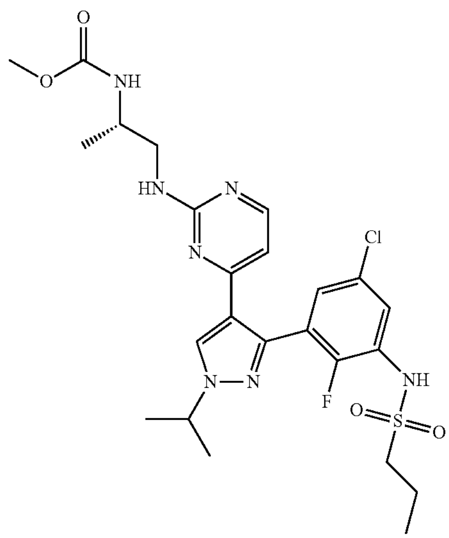 [SMILES: CCCS(=O)(=O)Nc1cc(Cl)cc(-c2nn(C(C)C)cc2-c2ccnc(NC[C@H](C)NC(=O)OC)n2)c1F] | | 0.002 | $^1$H NMR 400 MHz (CD$_3$OD) δ 8.41 (s, 1H), 8.06 (d, 1H), 7.57 (dd, 1H), 7.34 (dd, 1H), 6.64 (d, 1H), 4.63 (hept, 1H), 3.62-3.68 (m, 1H), 3.57 (s, 3H), 3.40-3.44 (m, 1H), 3.32-3.36 (m, 1H), 3.05 (q, 2H), 1.88 (q, 2H), 1.58 (d, 6H), 1.02 (d, 3H), 0.97 (t, 3H); MS m/z 568.2 (M + 1). |
| 2 | 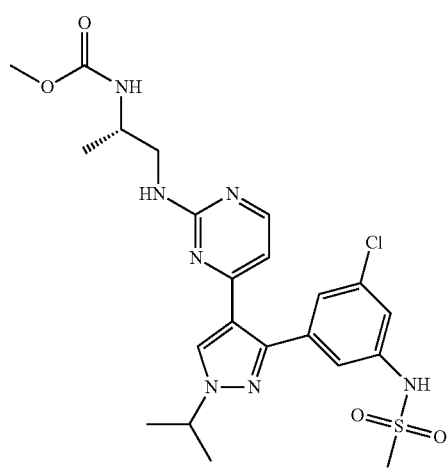 [SMILES: COC(=O)N[C@@H](C)CNc1nccc(-c2cn(C(C)C)nc2-c2cc(Cl)cc(NS(C)(=O)=O)c2)n1] | 0.018 | 0.0008 | MS m/z 522.1 (M + 1) |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
| --- | --- | --- | --- | --- |
| 3 | 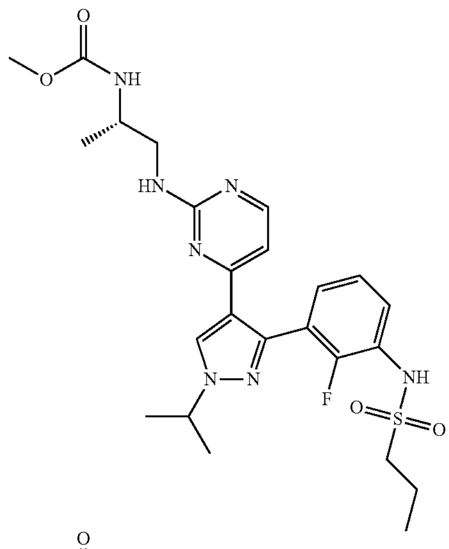 | 0.002 | | MS m/z 534.1 (M + 1) |
| 4 | 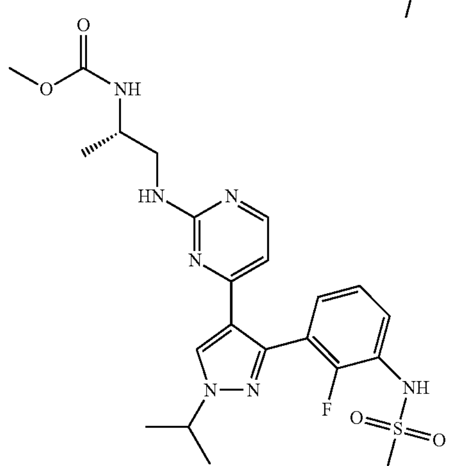 | 0.033 | 0.0023 | MS m/z 506.1 (M + 1) |
| 5 | 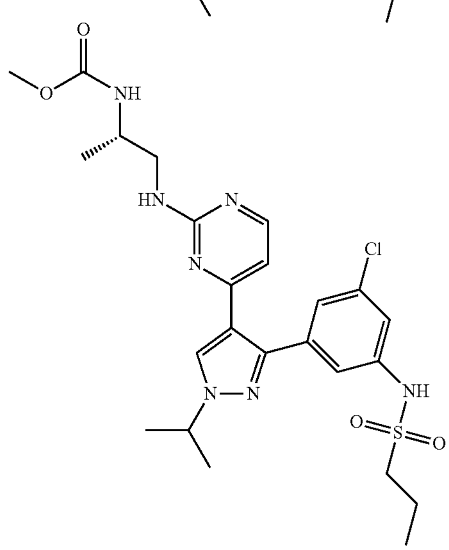 | 0.001 | 0.0002 | MS m/z 550.1 (M + 1) |

TABLE 1-continued
| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 6 | 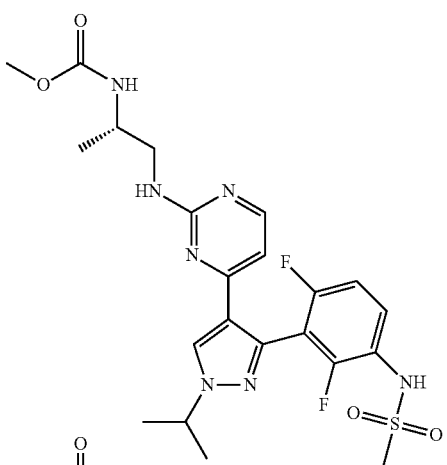 [SMILES: COC(=O)N[C@@H](C)CNc1nccc(-c2cn(C(C)C)nc2-c2c(F)ccc(NS(C)(=O)=O)c2F)n1] | 0.046 | 0.0039 | MS m/z 524.2 (M + 1) |
| 7 | 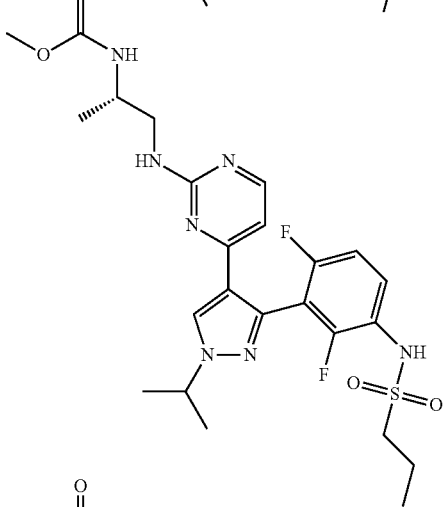 | 0.008 | 0.0007 | MS m/z 552.2 (M + 1) |
| 8 | 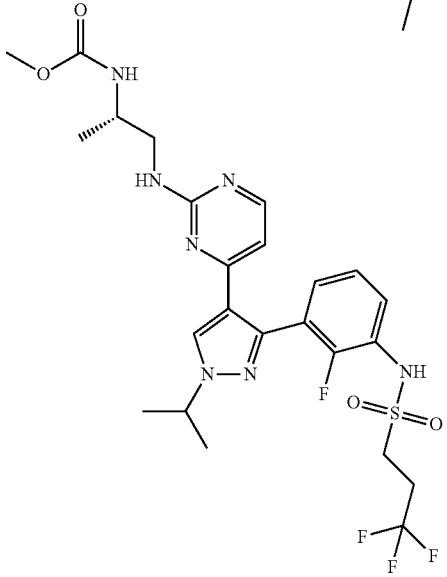 [SMILES: COC(=O)N[C@@H](C)CNc1nccc(-c2cn(C(C)C)nc2-c2cccc(NS(=O)(=O)CCC(F)(F)F)c2F)n1] | 0.027 | | MS m/z 588.2 (M + 1) |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 9 | 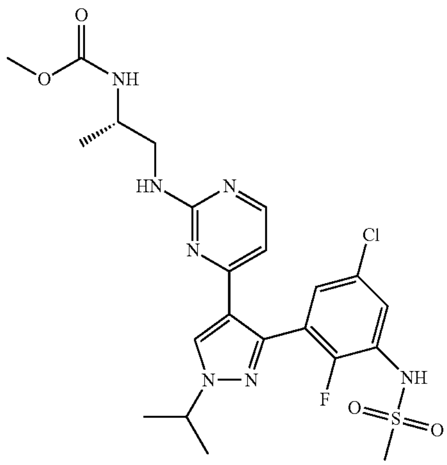 | 0.002 | 0.0003 | $^1$H NMR 400 MHz (CD$_3$OD) δ 8.41 (s, 1H), 8.08 (d, J = 5.6 Hz, 1H), 7.57 (dd, J = 6.4, 2.6 Hz, 1H), 7.34 (dd, J = 5.6, 2.6 Hz, 1H), 6.65 (brs, 1H), 4.63 (hept, J = 6.8 Hz, 1H), 3.62-3.68 (m, 1H), 3.57 (s, 3H), 3.40-3.44 (m; 1H), 3.32-3.36 (m, 1H), 3.00 (s, 3H), 1.58 (d, J = 6.8 Hz, 6H), 1.02 (d, J = 4.8 Hz, 3H).MS m/z 540.1 (M + 1) |
| 10 | 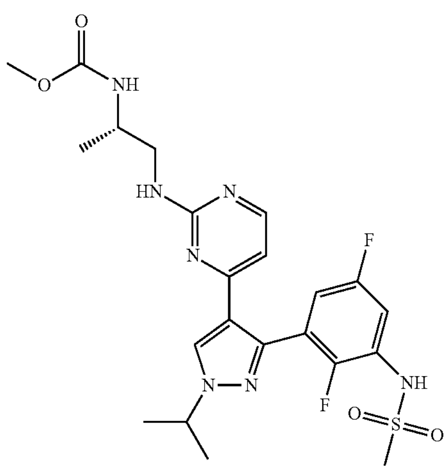 | 0.003 | 0.0006 | $^1$H NMR 400 MHz (CD$_3$OD) δ 8.41 (s, 1H), 8.08 (d, 1H), 7.37 (ddd, 1H), 7.08 (ddd, 1H), 6.62 (brs, 1H), 4.63 (hept, 1H), 3.63 (s, 3H), 3.54-3.58 (m, 1H), 3.34-3.40 (m, 2H), 3.00 (s, 3H), 1.58 (d, 6H), 1.12 (d, 3H); MS m/z 524.1 (M + 1). |
| 11 | 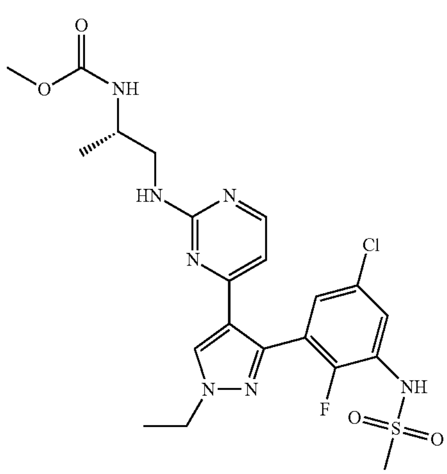 [SMILES: CCn1cc(-c2ccnc(NC[C@H](C)NC(=O)OC)n2)c(-c2cc(Cl)cc(NS(C)(=O)=O)c2F)n1] | 0.003 | 0.0005 | $^1$H NMR 400 MHz (CD$_3$OD) δ 8.34 (s, 1H), 8.09 (d, 1H), 7.57 (dd, 1H), 7.35 (dd, 1H), 6.65 (brs, 1H), 4.28 (q, 2H), 3.68-3.71 (m, 1H), 3.57 (s, 3H), 3.32-3.36 (m, 2H), 3.00 (s, 3H), 1.54 (t, 3H), 1.02 (d, 3H); MS m/z 526.0 (M + 1). |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 12 | 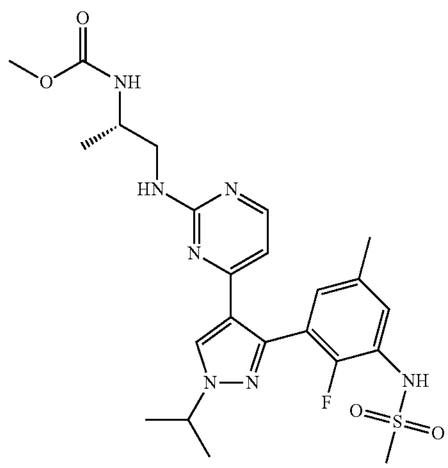 [SMILES: COC(=O)N[C@@H](C)CNc1nccc(-c2cn(C(C)C)nc2-c2cc(C)cc(NS(C)(=O)=O)c2F)n1] | 0.004 | 0.00095 | $^1$H (400 MHz, CDCl$_3$) δ 8.12 (s, 2H), 7.40 (d, 1H), 7.20 (d, 1H), 7.10 (m, 1H), 6.40 (s, 1H), 5.35 (s, 1H), 5.25 (d, 1H), 4.60 (m, 1H), 3.90(s, 1H), 3.65 (s, 3H), 3.30 (s, 1H), 3.00 (s, 3H), 2.40 (s, 3H), 1.60 (d, 6H), 1.10 (d, 3H). MS (ESI) m/z: 521 (M + H)$^+$. |
| 13 | 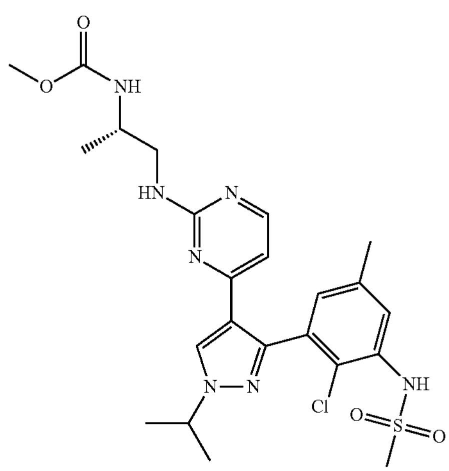 | 0.006 | 0.0010 | $^1$H (400 MHz, CDCl$_3$) δ 10.10 (s, 1H), 8.60 (s, 1H), 7.75 (s, 1H), 7.60 (d, 1H), 7.15 (d, 1H), 7.05 (s, 1H), 6.30 (s, 1H), 4.95 (s, 1H), 4.65 (m, 1H), 3.95 (s, 1H), 3.65 (s, 3H), 3.45 (s, 1H), 3.30 (s, 1H), 3.05 (s, 3H), 2.45 (s, 3H), 1.65 (d, 6H), 1.20 (d, 3H). MS (ESI) m/z: 537 (M + H)$^+$. |
| 14 | 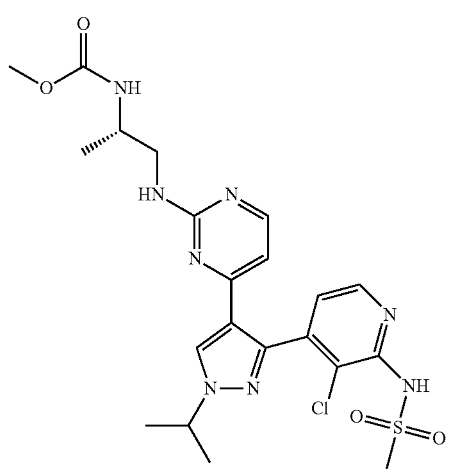 | 0.079 | | MS m/z 523.1 (M + 1)$^1$ |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 15 | 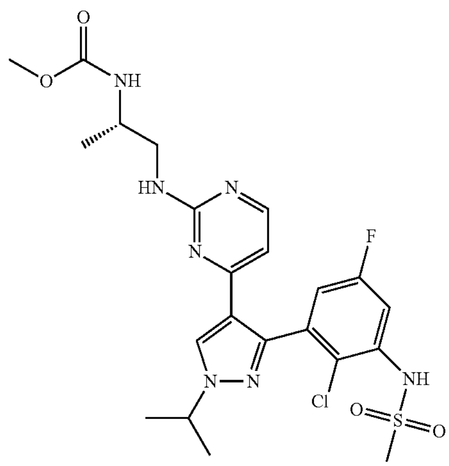 | 0.004 | 0.0011 | MS m/z 540.1 (M + 1) |
| 16 | 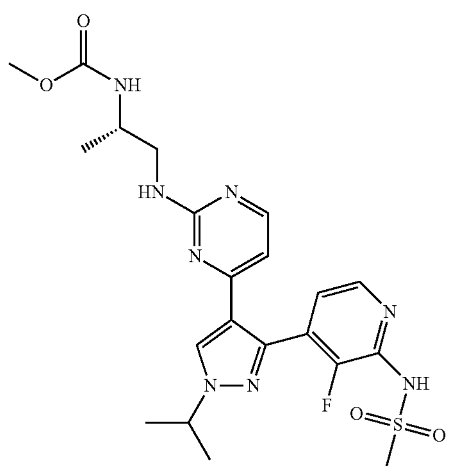 [SMILES: COC(=O)N[C@@H](C)CNc1nccc(-c2cn(C(C)C)nc2-c2ccnc(NS(C)(=O)=O)c2F)n1] | 1.4 | 0.024 | MS m/z 507.2 (M + 1) |
| 17 | 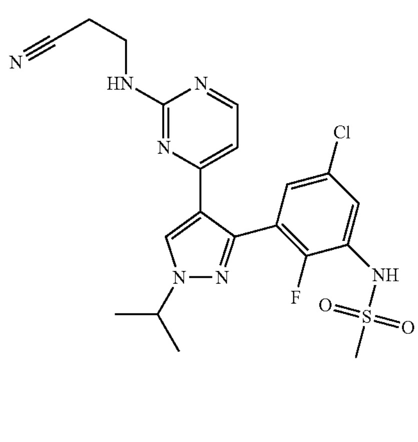 [SMILES: CC(C)n1cc(-c2ccnc(NCCC#N)n2)c(-c2cc(Cl)cc(NS(C)(=O)=O)c2F)n1] | 0.002 | | MS m/z 478.1 (M + 1) |

TABLE 1-continued
| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 18 | 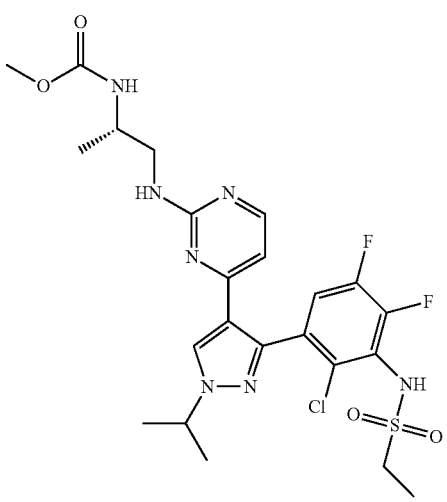 [SMILES: CCS(=O)(=O)Nc1c(F)c(F)cc(-c2nn(C(C)C)cc2-c2ccnc(NC[C@H](C)NC(=O)OC)n2)c1Cl] | 0.012 | | $^1$H NMR 400 MHz (CD$_3$OD) δ 8.45 (s, 1H), 8.04 (d, 1H), 7.41 (dd, 1H), 6.57 (d, 1H), 4.61 (hept, 1H), 3.70-3.74 (m, 1H). 3.58 (s, 3H), 3.34-3.40 (m, 2H), 3.23 (q, 2H), 1.58 (d, 6H), 1.43 (t, 3H), 1.02 (d, 3H); MS m/z 573.1 (M + 1). |
| 19 | 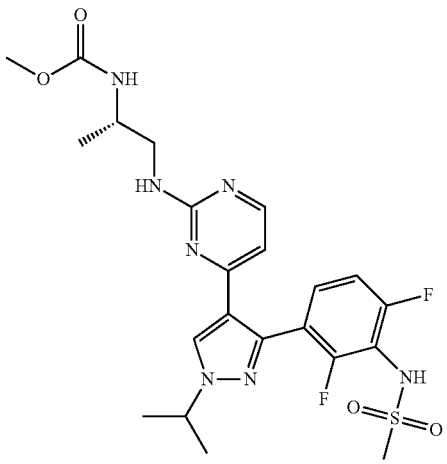 [SMILES: COC(=O)N[C@@H](C)CNc1nccc(-c2cn(C(C)C)nc2-c2ccc(F)c(NS(C)(=O)=O)c2F)n1] | 0.093 | 0.0061 | MS m/z 524.1 (M + 1) |
| 20 | 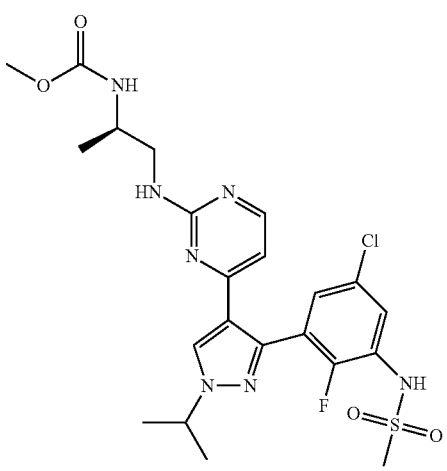 [SMILES: COC(=O)N[C@H](C)CNc1nccc(-c2cn(C(C)C)nc2-c2cc(Cl)cc(NS(C)(=O)=O)c2F)n1] | 0.007 | 0.0008 | MS m/z 540.2 (M +1) |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 21 | 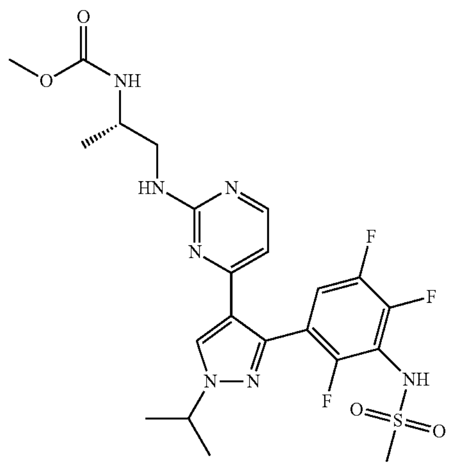 [SMILES: COC(=O)N[C@@H](C)CNc1nccc(-c2cn(C(C)C)nc2-c2cc(F)c(F)c(NS(C)(=O)=O)c2F)n1] | | 0.045 | $^1$H (400 MHz, CDCl$_3$) δ 7.95 (s, 2H), 7.30 (s, 1H), 6.40 (s, 1H), 5.15 (s, 1H), 4.50 (m, 1H), 3.70 (s, 1H), 3.52 (s, 3H), 3.20 (s, 1H), 3.05 (s, 3H), 1.50 (d, 6H), 1.05 (d, 3H). MS (ESI) m/z: 542 (M + H)$^+$. |
| 22 | 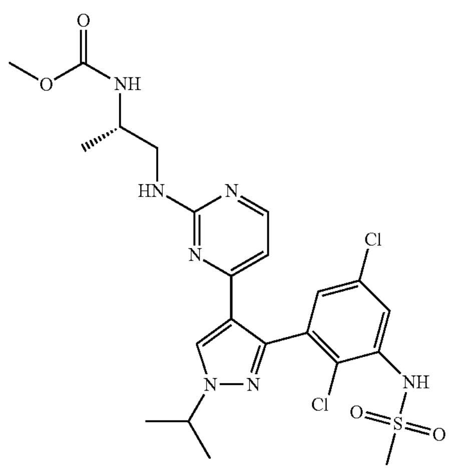 [SMILES: COC(=O)N[C@@H](C)CNc1nccc(-c2cn(C(C)C)nc2-c2cc(Cl)cc(NS(C)(=O)=O)c2Cl)n1] | | 0.006 | $^1$H (400 MHz, CDCl$_3$) δ 8.50 (s, 1H), 7.85 (s, 1H), 7.80 (s, 1H), 7.30 (s, 1H), 6.40 (s, 1H), 5.0 (s, 1H), 4.62 (m, 1H), 3.90 (s, 1H), 3.65 (s, 3H), 3.30 (s, 1H), 3.10 (s, 3H), 1.70 (d, 6H), 1.20 (d, 3H). MS (ESI) m/z: 557 (M + H)$^+$. |
| 23 | 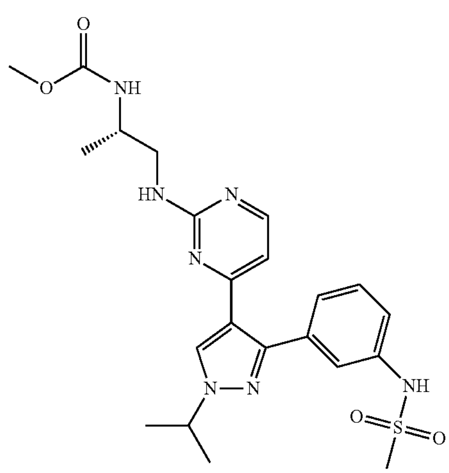 [SMILES: COC(=O)N[C@@H](C)CNc1nccc(-c2cn(C(C)C)nc2-c2cccc(NS(C)(=O)=O)c2)n1] | | 1.15 | MS m/z 488.2 (M + 1) |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 24 | 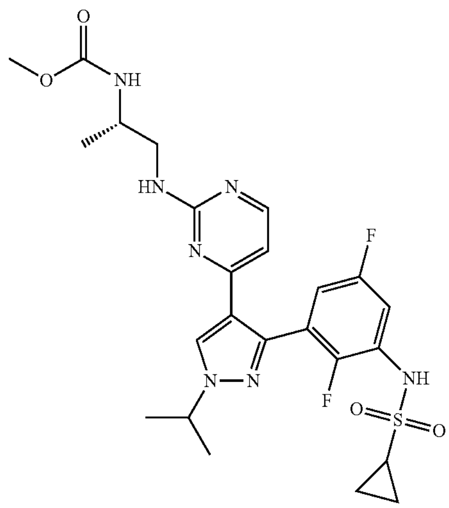 [SMILES: COC(=O)N[C@@H](C)CNc1nccc(-c2cn(C(C)C)nc2-c2cc(F)cc(NS(=O)(=O)C3CC3)c2F)n1] | | 0.023 | MS m/z 550.1 (M + 1) |
| 25 | 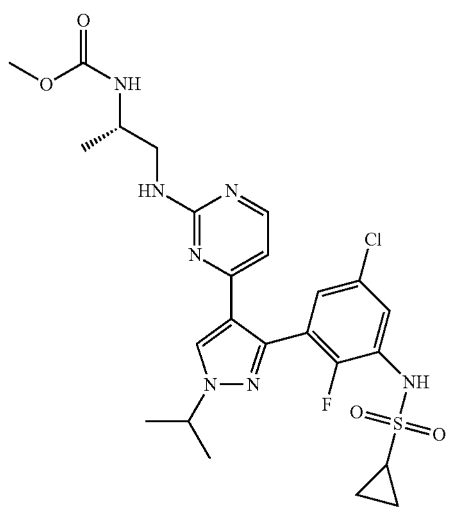 | | 0.002 | MS m/z 566.1 (M + 1) |
| 26 | 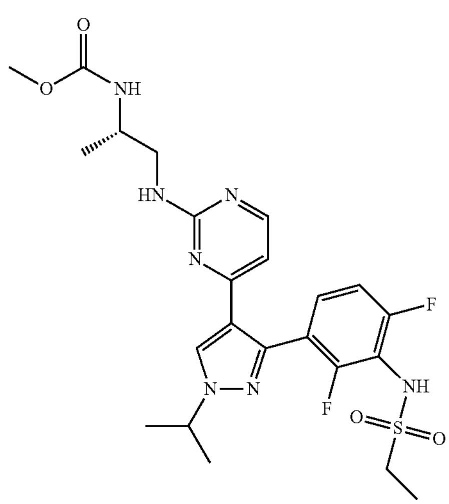 [SMILES: CCS(=O)(=O)Nc1c(F)ccc(-c2nn(C(C)C)cc2-c2ccnc(NC[C@H](C)NC(=O)OC)n2)c1F] | 0.014 | 0.0017 | MS m/z 538.2 (M + 1) |

TABLE 1-continued
| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 27 | 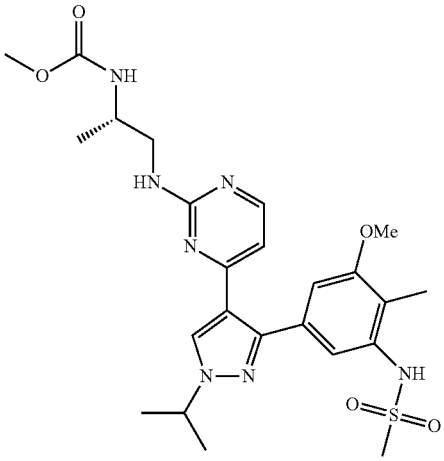 [SMILES: COC(=O)N[C@@H](C)CNc1nccc(-c2cn(C(C)C)nc2-c2cc(NS(C)(=O)=O)c(C)c(OC)c2)n1] | >20 | 0.39 | MS m/z 532.2 (M + 1) |
| 28 | 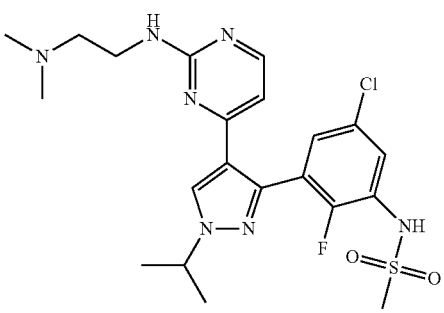 [SMILES: CC(C)n1cc(-c2ccnc(NCCN(C)C)n2)c(-c2cc(Cl)cc(NS(C)(=O)=O)c2F)n1] | 0.55 | 0.09 | MS m/z 496.1 (M + 1) |
| 29 | 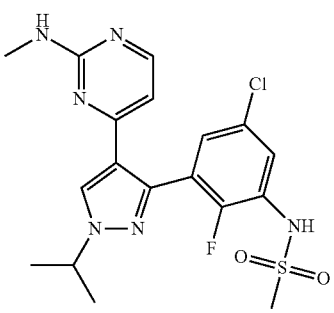 [SMILES: CNc1nccc(-c2cn(C(C)C)nc2-c2cc(Cl)cc(NS(C)(=O)=O)c2F)n1] | 0.076 | 0.008 | MS m/z 439.0 (M + 1) |
| 30 | 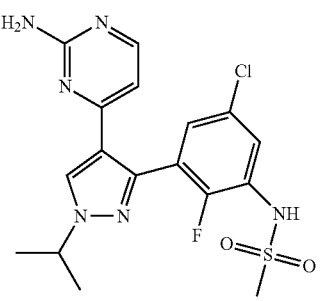 [SMILES: CC(C)n1cc(-c2ccnc(N)n2)c(-c2cc(Cl)cc(NS(C)(=O)=O)c2F)n1] | 0.069 | 0.0043 | MS m/z 425.1 (M + 1) |

TABLE 1-continued

| Cpd # | Structure | A375 CP IC$_{50}$ (μM) | BRAF V600E bio-chemical IC$_{50}$ (μM) | Physical Data $^1$H NMR 400 MHz and/or MS (m/z) |
|---|---|---|---|---|
| 31 | 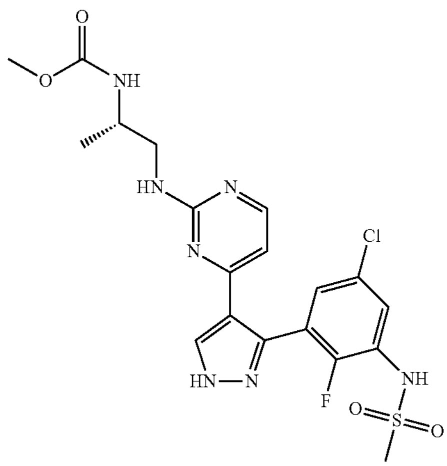 [SMILES: COC(=O)N[C@@H](C)CNc1nccc(-c2c[nH]nc2-c2cc(Cl)cc(NS(C)(=O)=O)c2F)n1] | 0.18 | 0.0008 | MS m/z 497.9 (M + 1) |
| 32 | 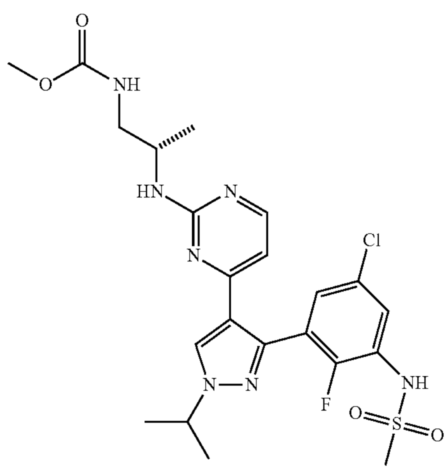 [SMILES: COC(=O)NC[C@H](C)Nc1nccc(-c2cn(C(C)C)nc2-c2cc(Cl)cc(NS(C)(=O)=O)c2F)n1] | 0.031 | 0.0029 | MS m/z 540.1 (M + 1) |
| 33 | 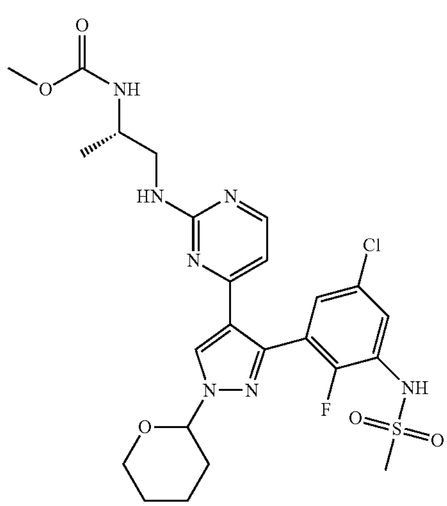 [SMILES: COC(=O)N[C@@H](C)CNc1nccc(-c2cn(C3CCCCO3)nc2-c2cc(Cl)cc(NS(C)(=O)=O)c2F)n1] | 0.007 | | MS m/z 582.1 (M + 1) |

TABLE 1-continued

| Cpd # | Structure | A375 CP IC$_{50}$ (μM) | BRAF V600E biochemical IC$_{50}$ (μM) | Physical Data $^1$H NMR 400 MHz and/or MS (m/z) |
|---|---|---|---|---|
| 34 | 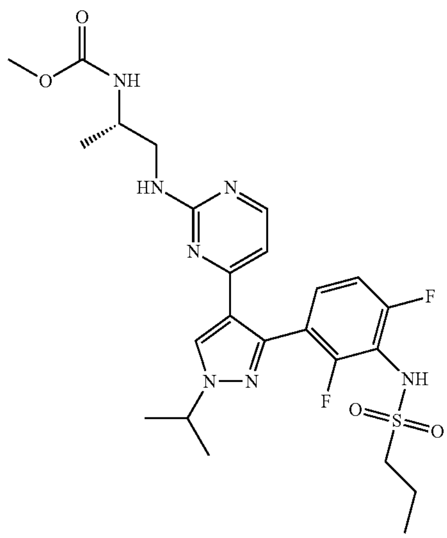 [SMILES: CCCS(=O)(=O)Nc1c(F)ccc(-c2nn(C(C)C)cc2-c2ccnc(NC[C@H](C)NC(=O)OC)n2)c1F] | 0.013 | 0.0027 | $^1$H NMR 400 MHz (CD$_3$OD) δ 8.41 (s, 1H), 8.06 (d, 1H), 7.47 (ddd, 1H), 7.17 (ddd, 1H), 6.59 (d, 1H), 4.62 (hept, 1H), 3.71-3.74 (m, 1H), 3.58 (s, 3H), 3.34-3.40 (m, 2H), 3.05 (q, 2H), 1.88 (q, 2H), 1.58 (d, 6H), 1.02 (d, 3H), 0.97 (t, 3H); MS m/z 552.1 (M + 1). |

Example 122

B-Raf V600E/Mek Amplified Luminescence Proximity Homogeneous Assay (B-Raf V600E Biochemical)

B-Raf (V600E; 4 μM) and biotinylated Mek (kinase dead; 10 nM) were combined at 2× final concentrations in assay buffer (50 mM Tris, pH 7.5, 15 mM MgCl$_2$, 0.01% BSA and 1 mM DTT) and dispensed 10 μl per well in assay plates (Greiner white 384 well assay plates #781207) containing 0.5 μl of 40× of a compound of the invention diluted in 100% DMSO. The plate was incubated for 60 minutes at room temperature.

The B-Raf kinase activity reaction was started by the addition of 10 μl per well of 2×ATP (10 μM) diluted in assay buffer. After 3 hours, the reactions were stopped with the addition of 10 μl of stop reagent (60 mM EDTA, 0.01% Tween20). Phosphorylated product was measured using a rabbit anti-p-MEK (Cell Signaling, #9121) antibody and the Alpha Screen IgG (ProteinA) detection Kit (PerkinElmer #6760617R), by the addition of 30 μl to the well of a mixture of the antibody (1:2000 dilution) and detection beads (1:1000 dilution of both beads) in bead buffer (50 mM Tris, pH 7.5, 0.01% Tween20). The additions were carried out under dark conditions to protect the detection beads from light. A lid was placed on top of the plate and the plate was incubated for 1 hour at room temperature. The luminescence was read on a PerkinElmer Envision instrument. The concentration of each compound for 50% inhibition (IC$_{50}$) was calculated by non-linear regression using XL Fit data analysis software.

Compounds of the invention, in free form or in pharmaceutically acceptable salt form, exhibit valuable pharmacological properties, for example, as indicated by the in vitro tests described in this application. For example, compounds of the invention preferably show an IC$_{50}$ in the range of $1\times10^{-10}$ to $1\times10^{-5}$ M, preferably less than 500 nM, 250 nM, 100 nM and 50 nM for V600E B-Raf.

For example, IC$_{50}$ data for some compounds of the invention in the Luminescence Proximity Homogeneous Assay are shown in the Table, supra.

Example 123

A375 Cellular Proliferation Assay (A375 CP)

A375 is a melanoma cell line that harbors the B-Raf V600E mutation. A375-luc cells engineered to express luciferase are plated to 384-well white clear bottom plates as 1,500 cells/50 μl/well in DMEM containing 10% FBS. Compounds of the invention dissolved in 100% DMSO at appropriate concentrations are transferred to the cells by a robotic Pin Tool (100 nl). The cells are incubated for 2 days at 25° C., then 25 μl of BrightGlo™ is added to each well and the plates are read by luminescence. The concentration of each compound for 50% inhibition (IC$_{50}$) was calculated by non-linear regression using XL Fit data analysis software.

Compounds of the invention, in free form or in pharmaceutically acceptable salt form, exhibit valuable pharmacological properties, for example, as indicated by the in vitro tests described in this application. For example, compounds of the invention preferably show an IC$_{50}$ in the range of less than 500 nM, 250 nM, 100 nM and 50 nM for wild type and V600E B-Raf.

For example, IC$_{50}$ data for some compounds of the invention in the A375 Cellular Proliferation Assay are shown in the Table, infra.

Example 124

Immunoassays

Cells were seeded in 1640 RPMI+10% FBS at a density of 30×10$^3$ cells per 96-well in tissue culture treated plates, then incubated at 37° C. and 5% $CO_2$ for 24 hours before compounds were added. Test compounds were serially diluted in DMSO then added to the cells (final DMSO concentration of 0.1%) and incubated at 37° C. and 5% $CO_2$ for 3 hours. pMEK and pERK levels were measured using a sandwich immunoassay kit (Meso Scale Discovery). Culture supernatants were removed and cells were lysed by the addition of cold lysis buffer (provided in kit) for 30 minutes with gentle shaking. For detection of pMEK1/2 (Ser217/221) and pERK1/2 (Thr/Tyr202/204,Thr/Tyr185/187), lysates were added to the blocked antibody coated plates provided with the kits and incubated overnight at 4° C. with shaking. Plates were washed and the phosphoproteins detected using the provided labelled antibodies and read on a Sector 6000 instrument.

Example 125

SW620 Cell Viability Assay

SW620 cells were seeded in 1640 RPMI+10% FBS at a density of 1500 cells per 96-well in black walled, clear bottom tissue culture treated plates. Test compounds were serially diluted in DMSO then added to the cells (final DMSO concentration of 0.1%) and incubated at 37° C. and 5% $CO_2$ for 4 days. To measure cell viability, cell plates were brought to room temperature, culture media was removed, and 200 µl of Cell Titer-Glo reagent (Promega, kit components mixed as per the manufacturer's protocol then diluted 1:2 with growth media) was added to each well. Plates were shaken for 5 minutes, then incubated at room temperature for 5 minutes, and the luminescence was measured (Trilux, Perkin Elmer).

Example 126

Rat1 Soft Agarose Assay

Rat1 cells were suspended in 1% agarose (Lonza) at a density of 1000 cells per 96-well. The agarose/cell mixture was allowed to solidify. Test compounds were serially diluted in DMSO then added on top of the agarose cell mixture (final DMSO concentration of 0.2%) and incubated at 37° C. and 5% $CO_2$. After 17 days, colony growth was determined by incubating cells with alamarBlue (TREK Diagnostics) and measuring the metabolic activity with a Spectramax plate reader (Molecular Devices, Inc; absorbance measured at 562 nm).

Example 127

Liver Microsomal Clearance Assay

The in vitro microsomal clearance assay is designed to assess potential risks associated with hepatic metabolic stability of compounds. The test compound (1 µM) was incubated with liver microsomes (0.5 mg/mL) from different species (mouse, rat, monkey, dog and human) and NADPH (1 mM) in 100 mM potassium phosphate buffer at 37° C. At specific reaction time points (0, 5, 10 and 30 minutes), reaction aliquots were removed and reactions were terminated by addition of ice cold acetonitrile containing mass spectrometry internal standard. The samples were centrifuged and the supernatants were analyzed by LC-MS/MS. In vitro metabolic half-life ($t_{1/2}$, min) and intrinsic clearance (CLint, µL/min/mg) are based on the rate and extent of metabolism of the test compound as determined by the disappearance of the parent compound from the reaction mixture. These values may be scaled to predict hepatic metabolic clearance rate (CLh, mL/min/kg) and extraction ratio (ER, expressed as a ratio of the predicted hepatic metabolic clearance to hepatic blood flow in that species). In general, compounds with high predicted CLint or ER in vitro are considered to be at high risk for exposure-limiting metabolism in vivo.

Measured extraction ratios for some compounds of the invention are given in the table below.

| Cpd | Structure | ER Human | ER Mouse |
|---|---|---|---|
| 9 | 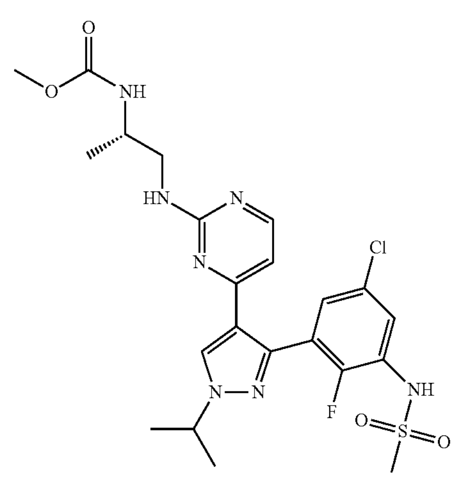 | <0.21 | 0.48 |

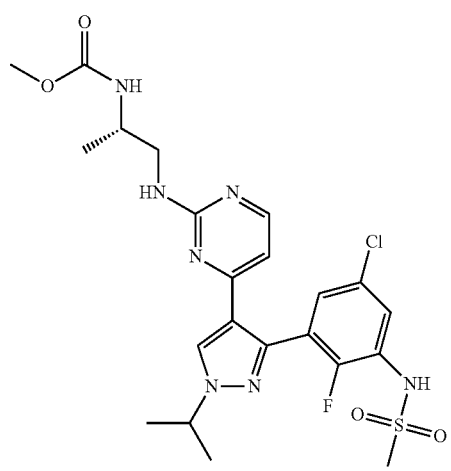 [SMILES: COC(=O)N[C@@H](C)CNc1nccc(-c2cn(C(C)C)nc2-c2cc(Cl)cc(NS(C)(=O)=O)c2F)n1]

-continued
| Cpd | Structure | ER Human | ER Mouse |
|---|---|---|---|
| 7 | 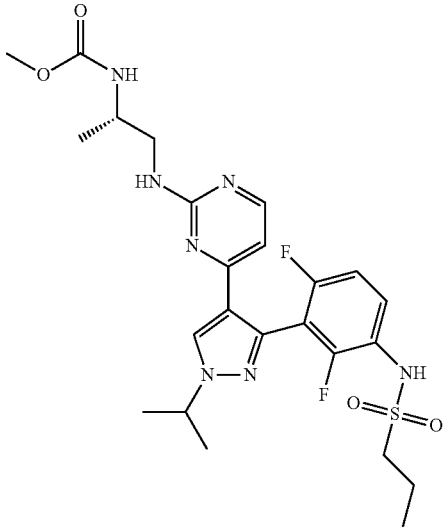 [SMILES: CCCS(=O)(=O)Nc1ccc(F)c(-c2nn(C(C)C)cc2-c2ccnc(NC[C@H](C)NC(=O)OC)n2)c1F] | 0.65 | 0.91 |
| 4 | 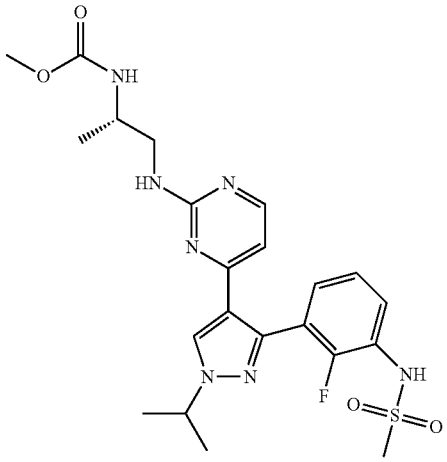 [SMILES: COC(=O)N[C@@H](C)CNc1nccc(-c2cn(C(C)C)nc2-c2cccc(NS(C)(=O)=O)c2F)n1] | <0.31 | 0.40 |
| 6 | 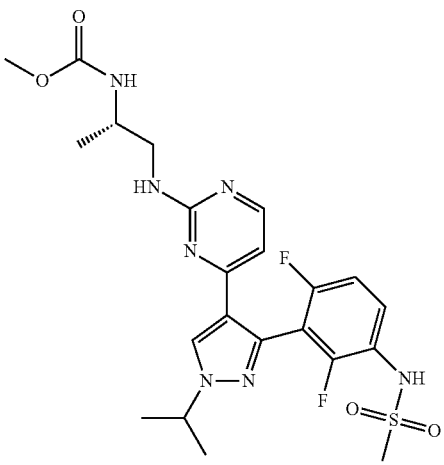 [SMILES: COC(=O)N[C@@H](C)CNc1nccc(-c2cn(C(C)C)nc2-c2c(F)ccc(NS(C)(=O)=O)c2F)n1] | 0.69 | |

-continued

| Cpd | Structure | ER Human | ER Mouse |
|---|---|---|---|
| 3 | 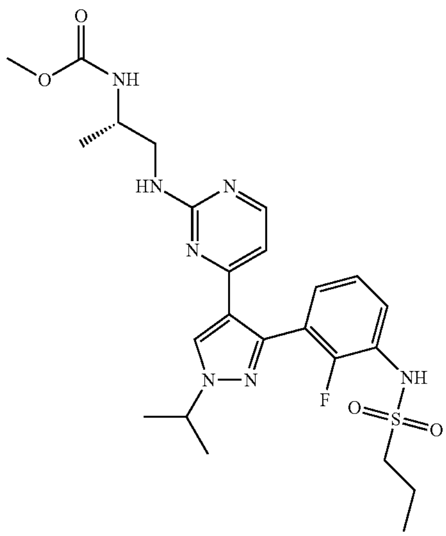 [SMILES: CCCS(=O)(=O)Nc1cccc(-c2nn(C(C)C)cc2-c2ccnc(NC[C@H](C)NC(=O)OC)n2)c1F] | 0.69 | 0.85 |
| 1 | 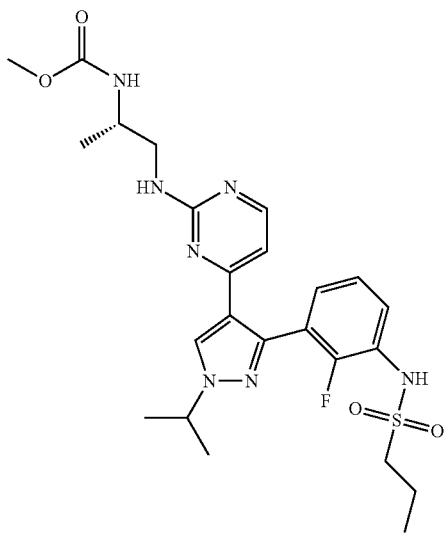 | 0.66 | 0.79 |
| | 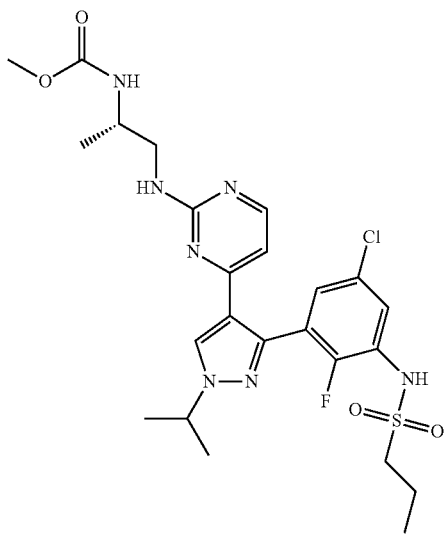 [SMILES: CCCS(=O)(=O)Nc1cc(Cl)cc(-c2nn(C(C)C)cc2-c2ccnc(NC[C@H](C)NC(=O)OC)n2)c1F] | | |

Example 128

A549 p38α MAP Kinase Bright-Glo Reporter Gene Assay

A549 cells were stably-transfected with the IL-8 promoter driven reporter, pGL3-IL8-Luc. The cells were plated at $4\times10^5$/ml into 384-well solid white plates (40 ul/well, 5% CD-FBS, 1×P/S, DMEM) and were incubated overnight (18-20 hours) at 37° C. Test compounds were serially diluted in DMSO, then 50 nl of test solution was added to the incubation (final DMSO concentration of 0.1%). After incubating with test compound for 30 min, cells were stimulated with 1 ng/ml IL-1 beta (10 ul of 5 ng/ml solution per well). Bright-Glo (25 ul/well) was added to measure luciferase expression after 7-8 hours of stimulation. $IC_{50}$ data for some compounds of the invention are given in the table below.

| Cpd | Structure | A549 p38 RGA IC$_{50}$ (µM) | A375 CP IC$_{50}$ (µM) | (p38 RGA)/ (A375) ratio |
|---|---|---|---|---|
| 9 | 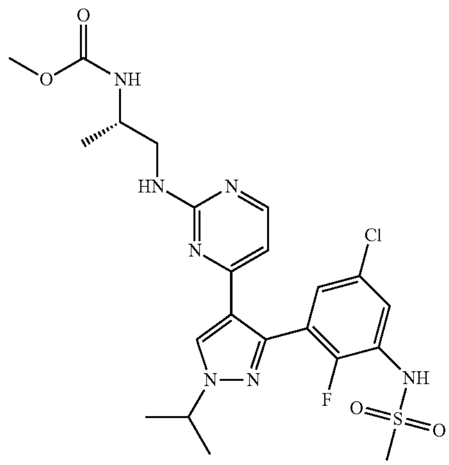 [SMILES: COC(=O)N[C@@H](C)CNc1nccc(-c2cn(C(C)C)nc2-c2cc(Cl)cc(NS(C)(=O)=O)c2F)n1] | 2.2 | 0.002 | 1100 |
| 32 | 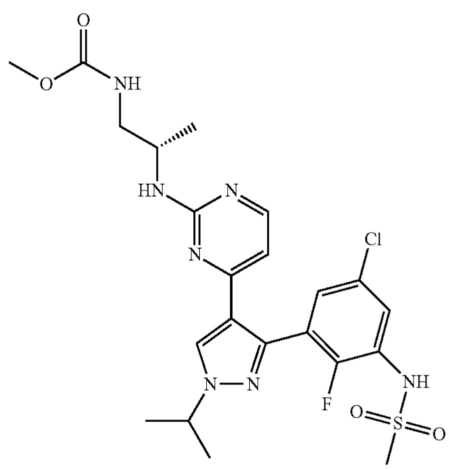 [SMILES: COC(=O)NC[C@H](C)Nc1nccc(-c2cn(C(C)C)nc2-c2cc(Cl)cc(NS(C)(=O)=O)c2F)n1] | 0.69 | 0.031 | 91 |
| 29 | 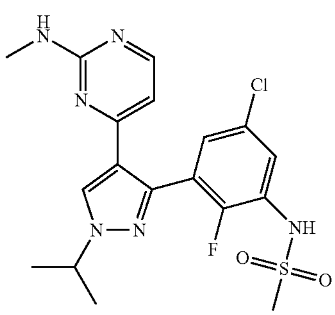 [SMILES: CNc1nccc(-c2cn(C(C)C)nc2-c2cc(Cl)cc(NS(C)(=O)=O)c2F)n1] | 17 | 0.076 | 220 |

Example 129

In Vivo Pharmacokinetics Assay

Full pharmacokinetics study: Male Balb/c mice (n=3, body weights 22-25 g) or male Wistar rats (n=3, body weights 250-300 g) were administered the test compound intravenously via the lateral tail vein or orally via gavage. The formulation was typically a 2.5 mg/mL solution of the compound in 75% PEG300 and 25% D5W. Six blood samples of 50 µL each were collected serially for 24 h after dosing. The blood samples were centrifuged to separate the plasma. Plasma samples were analyzed and quantified by LC-MS/MS.

Rapid pharmacokinetics study: Male Balb/c mice (n=3, body weights 22-25 g) or male Wistar rats (n=3, body weights 250-300 g) were administered the test compound intravenously (IV) via the lateral tail vein or orally (PO) via gavage. The formulation was typically a 2.5 mg/mL solution of the compound in 75% PEG300 and 25% D5W. Six blood samples of 50 µL each were collected serially for 24 h after dosing. Blood samples were centrifuged and plasma separated and pooled across the three animals at each time point per dose route. Plasma samples were analyzed and quantified by LC-MS/MS.

For both full and rapid pharmacokinetics studies, the following parameters were calculated by non-compartmental regression analysis using Winnonlin 5.0 software (Pharsight, Mountain View, Calif., USA): plasma clearance (Cl), plasma maximum concentration (Cmax), plasma area-under-the-concentration-time-curve ($AUC_{0\text{-}inf}$), and percent oral bioavailability (F %).

Pharmacokinetics parameters in mouse for some compounds of the invention are given in the table below.

| Compound # | Structure | Dose (mg/kg), PO/IV | Cl (mL/min/kg) | PO AUC (hrs* μM) | PO Cmax (μM) | F(%) |
|---|---|---|---|---|---|---|
| 9 | 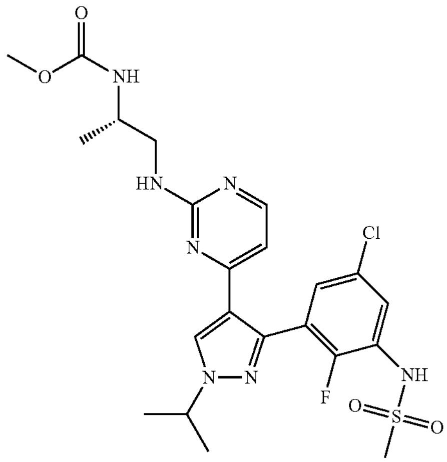 [SMILES: COC(=O)N[C@@H](C)CNc1nccc(-c2cn(C(C)C)nc2-c2cc(Cl)cc(NS(C)(=O)=O)c2F)n1] | 10/2 | 4.3 ± 0.4 | 30 ± 4 | 27 ± 4 | 43 ± 6 |
| 7 | 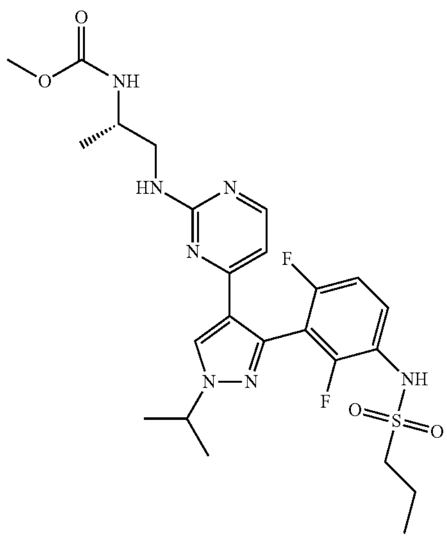 [SMILES: CCCS(=O)(=O)Nc1ccc(F)c(-c2nn(C(C)C)cc2-c2ccnc(NC[C@H](C)NC(=O)OC)n2)c1F] | 10/2 | 99 ± 13 | 0.24 ± 0.21 | 0.15 ± 0.07 | 8 ± 7 |
| 4 | 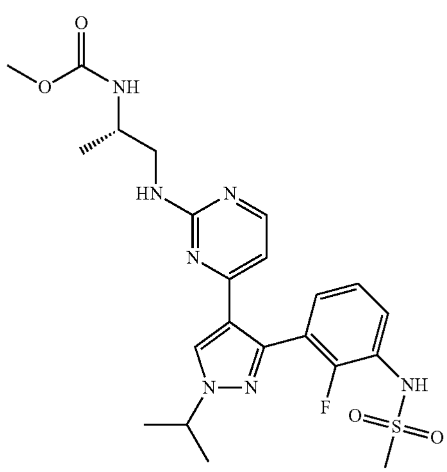 [SMILES: COC(=O)N[C@@H](C)CNc1nccc(-c2cn(C(C)C)nc2-c2cccc(NS(C)(=O)=O)c2F)n1] | 10/2 | 41 ± 9 | 3.0 ± 0.5 | 2.0 ± 0.5 | 36 ± 6 |

| Compound # | Structure | Dose (mg/kg), PO/IV | Cl (mL/min/kg) | PO AUC (hrs* μM) | PO Cmax (μM) | F(%) |
| --- | --- | --- | --- | --- | --- | --- |
| 6 | 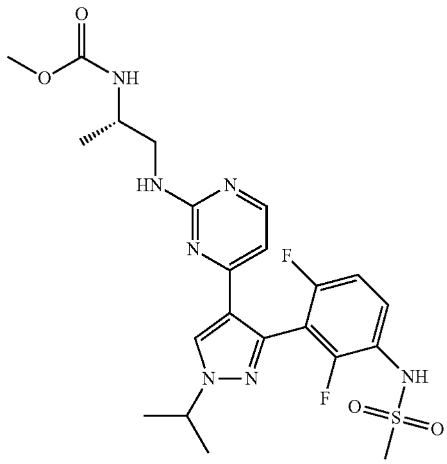 [SMILES: COC(=O)N[C@@H](C)CNc1nccc(-c2cn(C(C)C)nc2-c2c(F)ccc(NS(C)(=O)=O)c2F)n1] | 10/2 | 61 ± 6 | 1.1 ± 0.2 | 0.60 ± 0.02 | 15 ± 3 |
| 3 | 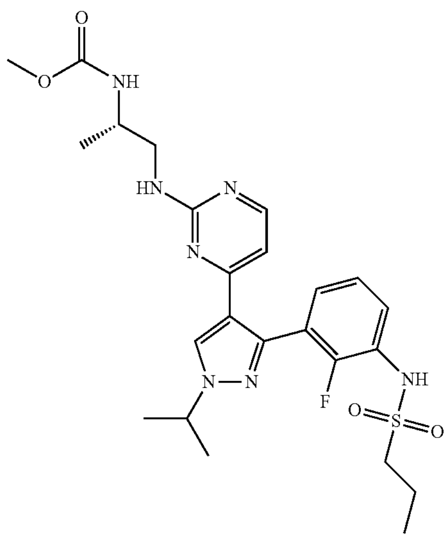 [SMILES: CCCS(=O)(=O)Nc1cccc(-c2nn(C(C)C)cc2-c2ccnc(NC[C@H](C)NC(=O)OC)n2)c1F] | 5/2 | 51 (n = 1) | 0.20 (n = 1) | 0.07 (n = 1) | 6 (n = 1) |
| 1 | 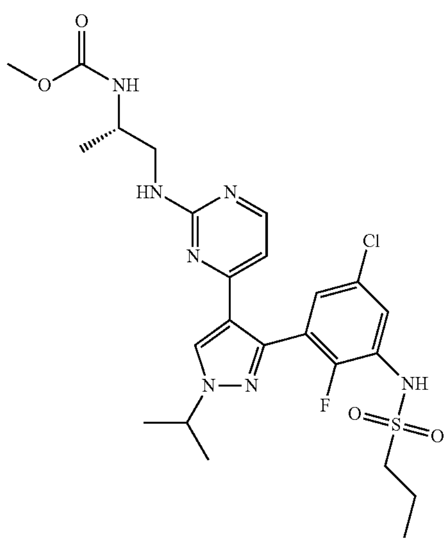 [SMILES: CCCS(=O)(=O)Nc1cc(Cl)cc(-c2nn(C(C)C)cc2-c2ccnc(NC[C@H](C)NC(=O)OC)n2)c1F] | 5/2 | 7.0 (n = 1) | 9.7 (n = 1) | 7.4 (n = 1) | 46 (n = 1) |

Compounds of Formula I, in free form or in pharmaceutically acceptable salt form, exhibit valuable pharmacological properties, for example, as indicated by the in vitro and in vivo tests described in this application. For example, compounds of Formula I preferably show an $IC_{50}$ in the A375 CP cell proliferation assay in the range of 250 nM or better, preferably less than 200 nM, 150 nM, 100 nM and 50 nM.

The 2-(methoxycarbonylamino)-1-propyl group at $R_1$ provides for a preferred level of activity and selectivity over other kinases including p38. For example, a greater than 30 fold increase in activity exists between compounds 9 and 29 where the A375 $IC_{50}$ is 2 nM and 76 nM, respectively.

The phenyl substitution pattern of compounds of Formula Ib is optimal for metabolic stability (ER in mouse and human) with fluoro or chloro at the $R_5$ position and fluoro, chloro, or methyl at the $R_3$ position. Compare, for example, the ER (human) in compounds 9 and 6 of <0.21 and 0.69, respectively.

The combination of the 2-(methoxycarbonylamino)-1-propyl group at $R_1$, the $R_3/R_5$ substitution pattern and the methyl group at $R_4$ has a surprising effect on the total drug exposure (AUC). See, for example, compound 9 (compared to compounds 1, 3, 4, 6 and 7) where the AUC, at an oral dose of 10 mg/kg, is 30±4 micromolar*hrs.

Example 130

In Vivo Efficacy—14 Day A375 Mouse Xenograft Model

A375 cells were grown in sterile conditions in a 37° C. incubator with 5% $CO_2$ for two to four weeks. The cells were cultured in RPMI-1640 media supplemented with 10% FBS. Cells were passaged twice weekly with 0.05% Trypsin/EDTA. On the day of implant, cells were harvested in HBSS (Hank's Balanced Salt Solution). Female Nu/Nu mice (Charles River, 10-11 weeks at start of study) were implanted with $5\times10^6$ A375 cells/mouse in 50% matrigel, 0.2 mL SQ right flank on day 1. At 19 days post-implant, mice were randomized into 6 groups (9 mice per group), with an average tumor volume of 215 mm³ and average body weight of 24 g. Test compound was dosed BID for 14 days commencing on day 19 using a dosing volume 0.2 mL per dose, with compound formulated at the appropriate concentration to attain the desired dose level. Clinical observations were made daily. Tumor volume and body weight were measured twice weekly. Endpoints: Any individual animal or group that exhibited body weight loss exceeding 25% of initial and/or tumor volume in excess of 3000 mm³.

Compound 9 (formulated in 20% PEG300/3% ETPGS/77% water) was dosed according to the above protocol using the following dosing regimen:
Group 1: Vehicle, qd×14
Group 2: 1 mg/kg Cpd 9, bid×14
Group 3: 3 mg/kg Cpd 9, bid×14
Group 4: 10 mg/kg Cpd 9, bid×14
Group 5: 20 mg/kg Cpd 9, bid×14

Tumor volume results were assessed at 14 days post-first dose. Partial response is defined as having tumor growth 20-50% of control tumor growth. Stable disease is defined as having final tumor volume within +/−20% of initial tumor size. Partial regression is defined as having final tumor volume<80% of initial tumor volume.
Group 2: partial response
Group 3: stable disease
Group 4: partial regression
Group 5: partial regression It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A method for treating a B-Raf protein kinase mediated cancer, wherein the cancer is selected from the group consisting of lung carcinoma, pancreatic carcinoma, bladder carcinoma, colon carcinoma, myeloid disorders, prostate cancer, thyroid cancer, melanoma, adenomas and carcinomas of the ovary, eye, liver, biliary tract, and nervous system, and wherein the method comprises administering to a subject in need of such treatment an effective amount of a compound of Formula (Ia), or a tautomer, stereoisomer or pharmaceutically acceptable salt thereof;
wherein the compound of Formula (Ia) is

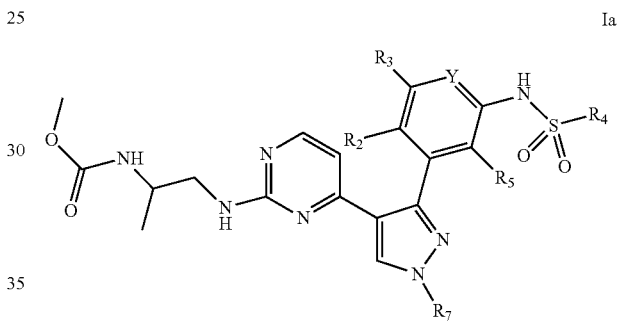

Ia in which:
Y is selected from N and $CR_6$;
$R_2$, $R_3$, $R_5$ and $R_6$ are independently selected from hydrogen, halo, cyano, $C_{1-4}$alkyl, halo-substituted-$C_{1-4}$alkyl, $C_{1-4}$alkoxy and halo-substituted-$C_{1-4}$alkoxy; with the proviso that when $R_5$ is fluoro, $R_3$ and $R_6$ are not both hydrogen;
$R_4$ is selected from —$R_9$ and —$NR_{10}R_{11}$; wherein $R_9$ is selected from $C_{1-6}$alkyl, $C_{3-8}$cycloalkyl, $C_{3-8}$heterocycloalkyl, aryl and heteroaryl; wherein
said alkyl, cycloalkyl, heterocycloalkyl, aryl or heteroaryl of $R_9$ is optionally substituted with 1 to 3 radicals independently selected from halo, cyano, $C_{1-4}$alkyl, halo-substituted-$C_{1-4}$alkyl, $C_{1-4}$alkoxy and halo-substituted-$C_{1-4}$alkoxy;
and $R_{10}$ and $R_{11}$ are independently selected from hydrogen and $R_9$;
$R_7$ is selected from hydrogen, $C_{1-4}$alkyl, $C_{3-5}$cycloalkyl and $C_{3-5}$heterocycloalkyl;
wherein said alkyl, cycloalkyl or heterocycloalkyl of $R_7$ is optionally substituted with 1 to 3 radicals independently selected from halo, cyano, hydroxyl, $C_{1-4}$alkyl, halo-substituted-$C_{1-4}$alkyl, $C_{1-4}$alkoxy and halo-substituted-$C_{1-4}$alkoxy.
2. The method of claim 1 in which $R_4$ is —$R_9$;
wherein $R_9$ is selected from $C_{1-3}$alkyl and $C_{3-8}$cycloalkyl;
wherein said alkyl or cycloalkyl of $R_9$ is optionally substituted with 1 to 3 radicals independently selected from halo and halo-substituted-$C_{1-4}$alkyl.

3. The method of claim 2 in which:

$R_2$ is selected from hydrogen and fluoro;

$R_3$ is selected from chloro, fluoro and methyl;

$R_5$ is selected from hydrogen, chloro and fluoro;

Y is selected from N and $CR_6$; and $R_6$ is selected from hydrogen and fluoro.

4. The method of claim 1, wherein the compound of Formula (Ia) is selected from:

methyl N-[(2S)-1-({4-[3-(3-chloro-5-methanesulfonamidophenyl)-1-(propan-2-yl)-1H-pyrazol-4-yl]pyrimidin-2-yl}amino)propan-2-yl]carbamate;

methyl N-[(2S)-1-[(4-{3-[3-chloro-5-(propane-1-sulfonamido)phenyl]-1-(propan-2-yl)-1H-pyrazol-4-yl}pyrimidin-2-yl)amino]propan-2-yl]carbamate;

methyl N-[(2S)-1-({4-[3-(3-chloro-2-methanesulfonamidopyridin-4-yl)-1-(propan-2-yl)-1H-pyrazol-4-yl]pyrimidin-2-yl}amino)propan-2-yl]carbamate;

methyl N-[(2S)-1-({4-[3-(3-fluoro-2-methanesulfonamidopyridin-4-yl)-1-(propan-2-yl)-1H-pyrazol-4-yl]pyrimidin-2-yl}amino)propan-2-yl]carbamate;

methyl N-[(2S)-1-({4-[3-(2-chloro-3-ethanesulfonamido-4,5-difluorophenyl)-1-(propan-2-yl)-1H-pyrazol-4-yl]pyrimidin-2-yl}amino)propan-2-yl]carbamate;

methyl N-[(2S)-1-({4-[3-(2,4-difluoro-3-methanesulfonamidophenyl)-1-(propan-2-yl)-1H-pyrazol-4-yl]pyrimidin-2-yl}amino)propan-2-yl]carbamate;

methyl N-[(2S)-1-({4-[1-(propan-2-yl)-3-(2,4,5-trifluoro-3-methanesulfonamidophenyl)-1H-pyrazol-4-yl]pyrimidin-2-yl}amino)propan-2-yl]carbamate;

methyl N-[(2S)-1-({4-[3-(3-methanesulfonamidophenyl)-1-(propan-2-yl)-1H-pyrazol-4-yl]pyrimidin-2-yl}amino)propan-2-yl]carbamate;

methyl N-[(2S)-1-({4-[3-(3-ethanesulfonamido-2,4-difluorophenyl)-1-(propan-2-yl)-1H-pyrazol-4-yl]pyrimidin-2-yl}amino)propan-2-yl]carbamate;

methyl N-[(2S)-2-({4-[3-(5-chloro-2-fluoro-3-methanesulfonamidophenyl)-1-(propan-2-yl)-1H-pyrazol-4-yl]pyrimidin-2-yl}amino)propyl]carbamate;

methyl N-[(2S)-1-({4-[3-(5-chloro-2-fluoro-3-methanesulfonamidophenyl)-1-(oxan-2-yl)-1H-pyrazol-4-yl]pyrimidin-2-yl}amino)propan-2-yl]carbamate;

methyl N-[(2S)-1-[(4-{3-[2,4-difluoro-3-(propane-1-sulfonamido)phenyl]-1-(propan-2-yl)-1H-pyrazol-4-yl}pyrimidin-2-yl)amino]propan-2-yl]carbamate;

methyl N-[(2S)-1-({4-[3-(3-cyclopropanesulfonamido-2,5-difluorophenyl)-1-(propan-2-yl)-1H-pyrazol-4-yl]pyrimidin-2-yl}amino)propan-2-yl]carbamate;

methyl N-[(2S)-1-({4-[3-(5-chloro-3-cyclopropanesulfonamido-2-fluorophenyl)-1-(propan-2-yl)-1H-pyrazol-4-yl]pyrimidin-2-yl}amino)propan-2-yl]carbamate;

methyl N-[(2S)-1-({4-[3-(5-chloro-2-fluoro-3-methanesulfonamidophenyl)-1H-pyrazol-4-yl]pyrimidin-2-yl}amino)propan-2-yl]carbamate; and methyl N-[(2S)-1-[(4-{3-[5-chloro-2-fluoro-3-(propane-1-sulfonamido)phenyl]-1-(propan-2-yl)-1H-pyrazol-4-yl}pyrimidin-2-yl)amino]propan-2-yl]carbamate.

5. The method of claim 1 wherein the compound of Formula (Ia) is a compound of Formula (Ib):

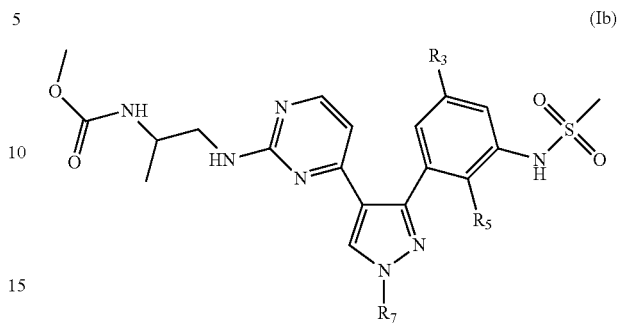

(Ib)

in which:

$R_3$ is selected from chloro, fluoro and methyl;

$R_5$ is selected from fluoro and chloro; and $R_7$ is selected from ethyl and isopropyl.

6. The method of claim 5 wherein the compound of Formula (Ib) is selected from:

methyl N-[(2S)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate;

methyl N-[(2S)-1-({4-[3-(2,5-difluoro-3-methanesulfonamidophenyl)-1-(propan-2-yl)-1H-pyrazol-4-yl]pyrimidin-2-yl}amino)propan-2-yl]carbamate;

methyl N-[(2S)-1-({4-[3-(5-chloro-2-fluoro-3-methanesulfonamidophenyl)-1-ethyl-1H-pyrazol-4-yl]pyrimidin-2-yl}amino)propan-2-yl]carbamate;

methyl N-[(2S)-1-({4-[3-(2-fluoro-3-methanesulfonamido-5-methylphenyl)-1-(propan-2-yl)-1H-pyrazol-4-yl]pyrimidin-2-yl}amino)propan-2-yl]carbamate;

methyl N-[(2S)-1-({4-[3-(2-chloro-3-methanesulfonamido-5-methylphenyl)-1-(propan-2-yl)-1H-pyrazol-4-yl]pyrimidin-2-yl}amino)propan-2-yl]carbamate;

methyl N-[(2S)-1-({4-[3-(2-chloro-5-fluoro-3-methanesulfonamidophenyl)-1-(propan-2-yl)-1H-pyrazol-4-yl]pyrimidin-2-yl}amino)propan-2-yl]carbamate;

methyl N-[(2R)-1-({4-[3-(5-chloro-2-fluoro-3-methanesulfonamidophenyl)-1-(propan-2-yl)-1H-pyrazol-4-yl]pyrimidin-2-yl}amino)propan-2-yl]carbamate; and methyl N-[(2S)-1-({4-[3-(2,5-dichloro-3-methanesulfonamidophenyl)-1-(propan-2-yl)-1H-pyrazol-4-yl]pyrimidin-2-yl}amino)propan-2-yl]carbamate.

7. The method of claim 1, further comprising administering to the subject an additional therapeutic agent selected from an anticancer drug, a pain medication, an antiemetic, an antidepressant or an anti-inflammatory agent.

8. The method of claim 7, wherein the additional therapeutic agent is administered to the subject simultaneously, concurrently or sequentially with the compound of Formula (Ia).

9. The method of claim 8, wherein the additional therapeutic agent is a Raf kinase inhibitor or an inhibitor of MEK, mTOR, HSP90, AKT, PI3K, CDK9, PAK, Protein Kinase C, a MAP kinase, a MAPK Kinase, or ERK.

10. The method of claim 9, wherein the additional therapeutic agent is an inhibitor of MEK or PI3K.

11. The method of claim 10, wherein the MEK inhibitor is selected from: AS703026; MSC1936369B; GSK1120212; AZD6244; PD-0325901; ARRY-438162; RDEA119; GDC0941; GDC0973; TAK-733; RO5126766; and XL-518.

12. The method of claim 11, wherein the MEK inhibitor is ARRY-438162.

13. The method of claim 11, wherein the MEK inhibitor is ARRY-438162 which is administered to the subject sequentially with the compound of Formula (Ia).

14. The method of claim 5, further comprising administering to the subject an additional therapeutic agent selected from an anticancer drug, a pain medication, an antiemetic, an antidepressant or an anti-inflammatory agent.

15. The method of claim 14, wherein the additional therapeutic agent is administered to the subject simultaneously, concurrently or sequentially with the compound of Formula (Ib).

16. The method of claim 15, wherein the additional therapeutic agent is a Raf kinase inhibitor or an inhibitor of MEK, mTOR, HSP90, AKT, PI3K, CDK9, PAK, Protein Kinase C, a MAP kinase, a MAPK Kinase, or ERK.

17. The method of claim 16, wherein the additional therapeutic agent is an inhibitor of MEK or PI3K.

18. The method of claim 17, wherein the MEK inhibitor is selected from: AS703026; MSC1936369B; GSK1120212; AZD6244; PD-0325901; ARRY-438162; RDEA119; GDC0941; GDC0973; TAK-733; RO5126766; and XL-518.

19. The method of claim 18 wherein the MEK inhibitor is ARRY-438162.

20. The method of claim 18, wherein the MEK inhibitor is ARRY-438162 which is administered to the subject sequentially with the compound of Formula (Ib).

21. The method of claim 6, further comprising administering to the subject an additional therapeutic agent selected from an anticancer drug, a pain medication, an antiemetic, an antidepressant or an anti-inflammatory agent.

22. The method of claim 21, wherein the additional therapeutic agent is administered to the subject simultaneously, concurrently or sequentially with the compound of Formula (Ib).

23. The method of claim 22, wherein the additional therapeutic agent is a Raf kinase inhibitor or an inhibitor of MEK, mTOR, HSP90, AKT, PI3K, CDK9, PAK, Protein Kinase C, a MAP kinase, a MAPK Kinase, or ERK.

24. The method of claim 23, wherein the additional therapeutic agent is an inhibitor of MEK or PI3K.

25. The method of claim 23, wherein the MEK inhibitor is selected from: AS703026; MSC1936369B; GSK1120212; AZD6244; PD-0325901; ARRY-438162; RDEA119; GDC0941; GDC0973; TAK-733; RO5126766; and XL-518.

26. The method of claim 25, wherein the MEK inhibitor is ARRY-438162.

27. The method of claim 25, wherein the MEK inhibitor is ARRY-438162 which is administered to the subject sequentially with the compound of Formula (Ib).

* * * * *